(12) United States Patent
Cai et al.

(10) Patent No.: US 7,932,251 B2
(45) Date of Patent: Apr. 26, 2011

(54) 6-PHENYL-1H-IMIDAZO[4,5-C]PYRIDINE-4-CARBONITRILE DERIVATIVES

(75) Inventors: Jiaqiang Cai, Newhouse (GB); Zoran Rankovic, Newhouse (GB); Philip Stephen Jones, Newhouse (GB); David Jonathan Bennett, Newhouse (GB); Xavier Fradera, Newhouse (GB)

(73) Assignee: N.V. Organon, Oss (NL)

( * ) Notice: Subject to any disclaimer, the term of this patent is extended or adjusted under 35 U.S.C. 154(b) by 35 days.

(21) Appl. No.: 12/173,623

(22) Filed: Jul. 15, 2008

(65) Prior Publication Data

US 2009/0099172 A1   Apr. 16, 2009

Related U.S. Application Data

(60) Provisional application No. 60/949,951, filed on Jul. 16, 2007.

(51) Int. Cl.
| A61K 31/437 | (2006.01) |
| A61K 31/438 | (2006.01) |
| A61K 31/5377 | (2006.01) |
| C07D 471/04 | (2006.01) |
| C07D 519/00 | (2006.01) |

(52) U.S. Cl. ........ 514/234.2; 514/253.04; 514/303; 544/127; 544/333; 544/362; 546/20; 546/118

(58) Field of Classification Search .......... None
See application file for complete search history.

(56) References Cited

U.S. PATENT DOCUMENTS

2007/0179138 A1* 8/2007 Cai et al. ............ 514/234.2

FOREIGN PATENT DOCUMENTS

| EP | 1724264 | 11/2006 |
| WO | WO 03/020278 | 3/2003 |
| WO | WO 03/020287 | 3/2003 |
| WO | WO 03/020721 | 3/2003 |
| WO | WO 2004/000819 | 12/2004 |
| WO | WO 2004/000843 | 12/2004 |
| WO | WO 2005/085210 | 9/2005 |
| WO | WO 2007/080191 A | 7/2007 |
| WO | WO 2009/010491 A | 1/2009 |

OTHER PUBLICATIONS

Yasuda et al. Advanced Drug Delivery Reviews vol. 57, p. 973-993 (2005).*
International Search Report (PCT/US 2007/050356) for mail date Mar. 16, 2007, 2 pages.
Written Opinion of the International Searching Authority for PCT/US2007/050356, 5 pages.
International Search Report (PCT/EP2010/050418) for mail date Mar. 1, 2010, 2 pages.
International Search Report (PCT/EP2008.059172) for mail date Oct. 17, 2008, 3 pages.
Written Opinion of the International Searching Authority for PCT/EP2008.059172), 5 pages.

* cited by examiner

*Primary Examiner* — Emily Bernhardt
(74) *Attorney, Agent, or Firm* — Susan L. Hess

(57) ABSTRACT

The present invention relates to 6-phenyl-1H-imidazo[4,5-c]pyridine-4-carbonitrile derivatives having the general Formula I

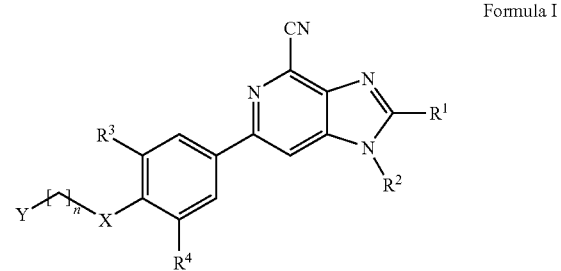

Formula I to pharmaceutical compositions comprising the same as well as to the use of these derivatives for the preparation of a medicament for the treatment of cathepsin S related diseases such as atherosclerosis, obesity, inflammation and immune disorders, such as rheumatoid arthritis, psoriasis, cancer, and chronic pain, such as neuropathic pain.

14 Claims, No Drawings

6-PHENYL-1H-IMIDAZO[4,5-C]PYRIDINE-4-CARBONITRILE DERIVATIVES

This application claims benefit from U.S. Provisional Patent Application No. 60/949,951 filed Jul. 16, 2007.

The invention relates to 6-phenyl-1H-imidazo[4,5-c]pyridine-4-carbonitrile derivatives, to pharmaceutical compositions comprising the same, as well as to the use of these derivatives for the preparation of a medicament for the treatment of cathepsin S and/or cathepsin K related diseases such as osteoporosis, atherosclerosis, obesity, inflammation and immune disorders, such as rheumatoid arthritis, psoriasis, lupus, asthma and chronic pain, such as neuropathic pain.

Cysteine proteases represent a class of peptidases characterised by the presence of a cysteine residue in the catalytic site of the enzyme and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, autoimmune diseases, e.g. rheumatoid arthritis, psoriasis, asthma, osteoarthritis, osteoporosis, tumors, coronary disease, atherosclerosis, and infectious diseases.

Cathepsin S is highly expressed in antigen presenting cells of lymphatic tissues, primarily in lysosomes (Bromme et al., Science, 5, 789, 1996; Riese, et al., Immunity, 4, 357, 1996). In the antigen presenting cells cathepsin S plays a major role in antigen presentation by degradation of invariant chain that is associated with the major histocompatibility class II complex. Cathepsin S deficient mice are healthy and normal in most respects but exhibit defects in immune functions and showed marked resistance to the development or collagen-induced arthritis (Nakagawa et al., Immunity, 10, 207, 1999; Shi et al, Immunity, 10, 197, 1999; Yang et al., 174, 1729, 2005). Cathepsin S inhibitors are effective in an asthma model (Riese et al., J. Clin. Invest. 101, 2351, 1998). Blocking invariant chain degradation should decrease antigen presentation to CD4 cells specifically and as such reduces unwanted side effects of other immunosuppressive drugs such as steroids. A recent patent publication (Johnson & Johnson, US 2007/0117785) has revealed that inhibitors of cathepsin S block the presentation of several crude allergen extracts in a human ex vivo assay, thereby supporting the use of cathpsin S inhibitors for the treatment of certain allergic conditions, such as rheumatoid arthritis, psoriasis. Different from most other lysosomal proteases that are only active under acidic conditions, the activity of cathepsin S exhibits a broad pH optimum that extents to alkaline pH. This feature enables that cathepsin S to function both inside and outside lysosomes (Broemme et al., Febs Lett., 286, 189, 1991). The broad pH feature and the high elastase activity of extracellular cathepsin S could also contribute to extensive remodeling of extracellular matrix architecture. As a result, cathepsin S has been shown to degrade all of the major components of the extracellular matrix and has been implicated in the pathogenic response that leads to atherosclerosis, obesity, emphysema and chronic obstructive pulmonary disease and cancer (Shi, et al., Atherosclerosis, 186, 411, 2006; Clement et al., Clin Chem Lab Med., 45(3), 328, 2007; Chang et al., J Cancer Mol., 3(1), 5, 2007; Shi et al., Immunity, 10, 197, 1999; Zheng et al., J. Clin. Invest., 106, 1081, 2000; Libby et al., J Clin Invest 102, 576, 1998; Sukhova et al, ibid, 111, 897, 2003). It was reported that serum cathepsin S level is significantly increased in both atherosclerosis and diabetes patients and modulating cathepsin S activity may have therapeutic application in the treatment of patients with these common illnesses (Shi, et al., Atherosclerosis, 186, 411, 2006; Clement et al., Clin Chem Lab Med., 45(3), 328, 2007). Cathepsin S has been indicated for pain (WO 2003020278; Clark et al., PNAS, 104, 10655, 2007), cancer process, e.g. angiogenesis, metastasis, growth and cell proliferation (Johnston et al., Am J Path., 163, 175, 2003; Kos et al., Brit J Cancer, 85, 1193, 2001).

Other cysteine cathepsins, e.g cathepsin K has strong collagenolytic, elastase and gelatinase activities (Bromme et al., J. Biol, Chem, 271, 2126-2132, 1996) and is predominantly expressed in osteoclasts (Bromme and Okamoto, Biol. Chem. Hopp-Seyler, 376, 379-384, 1995). It cleaves key bone matrix proteins, including collagen type I and II (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminuation of osteoclast mediated bone resorption. Cathepsin K inhibitors may therefore represent new therapeutic agents for the treatment of disease states in man such as osteoporosis, cancer, osteoarthritis. Sukhova et al (J. Clin. Invest. 102, 576-583, 1998) have demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and S at sites of plaques prone to rupture may thus represent an effective way of preventing such events.

4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO04/000819 (ASTRAZENECA AB) as cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB). Recently, carbonitrile substituted bicyclic nitrogen containing aromatic systems were disclosed in the International Patent Application WO 05/085210 (Ono Pharmaceutical Co.) as cysteine protease inhibitors useful in the treatment of osteoporosis.

There remains a need for further cathepsin inhibitors, especially for compounds having a preferential inhibitory activity for cathepsin S in comparison with cathepsin K.

To that aim the present invention provides 6-phenyl-1H-imidazo[4,5-c]pyridine-4-carbonitrile derivatives having the general Formula I

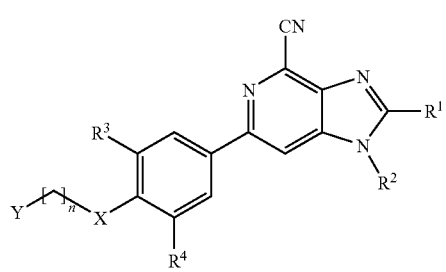

Formula I wherein
$R_1$ is H or $(C_{1-3})$alkyl;

$R_2$ is H or $(C_{1-3})$alkyl, $R_3$ is halogen or $(C_{1-4})$alkyl, optionally substituted with one or more halogens;

$R_4$ is H, halogen or CN;

X is $CH_2$, O or S;

n is 1-5;

Y is selected from OH, CN, $(C_{1-3})$alkylcarbonyl, $NR_5R_6$ and Z, wherein

Z is a saturated 5-or-6-membered heterocyclic ring containing 1-3 heteroatoms selected from O, S and $NR_7$, which ring may be substituted by OH, oxo, $(C_{1-3})$-alkyl, hydroxy$(C_{1-3})$alkyl or $(C_{1-3})$alkyloxy$(C_{1-3})$alkyl; or wherein Z is an aromatic 5-or-6-membered heterocyclic ring containing 1-3 heteroatoms selected from O, S and N, which ring may be substituted by OH, $(C_{1-3})$alkyl or hydroxy$(C_{1-3})$alkyl;

$R_5$ and $R_6$ are independently H, $(C_{3-8})$cycloalkyl or $(C_{1-6})$alkyl, optionally substituted with halogen, OH, $CF_3$, $(C_{3-8})$cycloalkyl, $(C_{1-6})$alkyloxy, $CONR_{14}R_{15}$, $NR_{14}R_{15}$, $SO_2R_{16}$, a 5- or 6-membered heteroaryl group containing 1-3 heteroatoms selected from O, S and N, or a 5-or-6-membered saturated heterocyclic group containing a heteroatom selected from O, S or $NR_8$; or $R_5$ and $R_6$ together with the nitrogen to which they are bound form a 4-10 membered saturated heterocyclic ring, optionally further comprising 1-3 heteroatoms selected from O, S and $NR_9$, the ring being optionallly substituted with OH, oxo, $(C_{1-4})$alkyl, hydroxy$(C_{1-3})$-alkyl, $(C_{3-8})$cycloalkyl, $CONR_{10}R_{11}$ or $NR_{10}R_{11}$;

$R_7$ is H, $(C_{1-3})$alkyl or hydroxy$(C_{1-3})$alkyl;

$R_8$ is H, $(C_{1-3})$alkyl or hydroxy$(C_{1-3})$alkyl;

$R_9$ is H, $(C_{1-3})$alkyl, $(C_{3-8})$cycloalkyl, hydroxy$(C_{1-3})$alkyl, $(C_{1-3})$alkoxy$(C_{1-3})$alkyl, $(C_{1-6})$-alkylcarbonyl, $(C_{1-6})$alkyloxycarbonyl, $CONR_{12}R_{13}$, $CH_2CONR_{12}R_{13}$ or a 5- or 6-membered heteroaryl group containing 1-3 heteroatoms selected from O, S and N;

$R_{10}$ and $R_{11}$ are independently H or $(C_{1-3})$alkyl, $R_{12}$ and $R_{13}$ are independently H or $(C_{1-3})$alkyl; or $R_{12}$ and $R_{13}$ together with the nitrogen to which they are bound form a 4-8 membered saturated heterocyclic ring, optionally further comprising a heteroatom selected from O and S;

$R_{14}$ and $R_{15}$ are independently H or $(C_{1-3})$alkyl; or $R_{14}$ and $R_{15}$ together with the nitrogen to which they are bound form a 4-8 membered saturated heterocyclic ring, optionally further comprising a heteroatom selected from O and S;

$R_{16}$ is $(C_{1-3})$alkyl; or a pharmaceutically acceptable salt thereof.

The 6-phenyl-1H-imidazo[4,5-c]pyridine-4-carbonitrile derivatives of the invention are inhibitors of cathepsin S and cathepsin K and can therefor be used for the preparation of a medicament for the treatment of osteoporosis, atherosclerosis, inflammation and immune disorders, such as rheumatoid arthritis, psoriasis, asthma, and chronic pain, such as neuropathic pain. The term $(C_{1-6})$alkyl, as used in the definition of formula I, means a branched or unbranched alkyl group having 1-6 carbon atoms, like hexyl, pentyl, 3-methyl-butyl, butyl, isobutyl, tertiary butyl, propyl, isopropyl, ethyl and methyl. The term $(C_{1-4})$alkyl means a branched or unbranched alkyl group having 1-4 carbon atoms, like butyl, isobutyl, tertiary butyl, propyl, isopropyl, ethyl and methyl.

The term $(C_{1-3})$alkyl means a branched or unbranched alkyl group having 1-3 carbon atoms, like propyl, isopropyl, ethyl and methyl.

In the terms $(C_{1-3})$alkylcarbonyl and $(C_{1-3})$alkyloxy$(C_{1-3})$alkyl each occurrence of $(C_{1-3})$alkyl has the meaning as previously given.

The term hydroxy$(C_{1-3})$alkyl means a $(C_{1-3})$alkyl group, as previously defined, substituted by a hydroxy group. A preferred hydroxy$(C_{1-3})$alkyl group is hydroxymethyl.

In the terms $(C_{1-6})$alkyloxy, $(C_{1-6})$alkylcarbonyl and $(C_{1-6})$alkyloxycarbonyl, $(C_{1-6})$alkyl has the meaning as previously defined.

The term $(C_{3-8})$cycloalkyl means a cycloalkyl group having 3-8 carbon atoms, such as cyclooctyl, cycloheptyl, cyclohexyl, cyclopentyl, cyclobutyl and cyclopropyl.

The term $(C_{6-10})$aryl means a radical derived from an aromatic group having 6-10 carbon atoms like for example phenyl and naphthyl.

In the definition of formula I Z can be a saturated 5-or-6-membered heterocyclic ring containing 1-3 heteroatoms selected from O, S and $NR_7$ Examples of such heterocyclic rings, which are attached through a carbon atom, are morpholinyl, piperazinyl, piperidinyl, pyrrolidinyl, thiomorpholinyl, 4-thiomorpholinyl, hexahydro-1,4-oxazepinyl, homopiperazinyl, imidazolidinyl, tetrahydrofuranyl and tetrahydrothiazolyl.

In the definition of formula I Z can be an aromatic 5- or 6-membered heterocyclic ring containing 1-3 heteroatoms selected from O, S and N. Examples of such aromatic heterocyclic rings, which are attached through a carbon or a nitrogen atom, are pyridyl, imidazolyl, pyrazolyl, pyrimidinyl, thiazolyl, isothiazolyl, oxazolyl, isoxazolyl, thienyl, oxadiazolyl, and the like. Preferred rings are 2-pyridyl, 3-pyridyl, 1,3-thiazol-2-yl, 1,2 oxazol-3-yl, imidazol-1-yl, tetrahydrobenzoimidazol-1-yl and 5-methyl-isoxazol-3-yl.

In the definition of formula I $R_5$ and $R_6$ can form together with the nitrogen to which they are bound a 4-10 membered saturated heterocyclic ring, such as an azetidine, a pyrrolidine, a piperidine, or a 1H-azepine ring. Such rings may contain 1-3 additional heteroatoms selected from O, S and $NR_9$ to form rings such as a morpholine, a thiomorpholine, a 4-dioxo-4-thiomorpholine, a hexahydro-1,4-oxazepine, a piperazine, a homopiperazine, an imidazolidine or a tetrahydrothiazole ring.

Also included in the definition of these rings are spiro-ring systems such as 1-oxo-2,8-diaza-spiro[4,5]dec-8-yl, 2,4-dioxo-1,3,8-triaza-spiro[4,5]dec-8-yl, 2,4-dioxo-1,3,8-triaza-spiro[4,5]dec-3-yl, 6,9-diaza-spiro[4,5]dec-9-yl and the like, as well as fused ring systems such as hexahydro-pyrrolo[1,2-a]pyrazin2-yl and the like.

The term 5- or 6-membered heteroaryl group as used in the definition of $R_5$ and $R_6$ and in the definition of $R_9$ means an aromatic 5- or 6-membered ring having 1-3 heteroatoms selected from nitrogen, oxygen and sulfur. Examples of such heteroaryl groups are pyridyl, imidazolyl, pyrazolyl, pyrimidinyl, thiazolyl, isothiazolyl, oxazolyl, isoxazolyl, thienyl, oxadiazolyl, and the like. Preferred heteroaryl groups are 2-pyridyl, 3-pyridyl, 1,3-thiazol-2-yl, 1,2 oxazol-3-yl and 5-methyl-isoxazol-3-yl.

In the definition of formula I $R_{12}$ and $R_{13}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

In the definition of formula I $R_{14}$ and $R_{15}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

The term halogen means F, Cl, Br, or I. When halogen is a substituent at an alkyl group, F is preferred. A preferred halogen substituted alkyl group is trifluoromethyl.

Preferred in the invention are those compounds according to Formula I wherein $R_1$ is H. Further preferred are compounds of formula I wherein $R_3$ is $CF_3$ and $R_4$ is H.

Also preferred are compounds of the invention wherein X is O and n is 1 or 2 or 3

Especially preferred are compounds of the invention wherein Y is $NR_5R_6$. Specifically preferred 6-phenyl-1H-imidazo[4,5-c]pyridine-4-carbonitrile derivatives of the invention are:

- 6-[4-(3-dimethylaminopropoxy)-3-(trifluoromethyl)-phenyl]-1-methyl-1H-imidazo[4,5-c]pyridine-4-carbonitrile;
- 1-methyl-6-[4-(3-pyrrolidin-1-ylpropoxy)-3-(trifluoromethyl)-phenyl]-1H-imidazo-[4,5-c]pyridine-4-carbonitrile;
- 6-[4-(3-N,N-diethylamino-propoxy)-3-(trifluoromethyl)-phenyl]-1-methyl-1H-imidazo[4,5-c]pyridine-4-carbonitrile;
- 1-methyl-6-[3-(trifluoromethyl)-4-(3-(3,3,4-trimethylpiperazin-1-yl)-propoxy)-phenyl]-1H-imidazo[4,5-c]pyridine-4-carbonitrile;
- 6-{4-[3-(3,3-dimethylpiperazin-1-yl)-propoxy]-3-(trifluoromethyl)-phenyl}-1-methyl-1H-imidazo[4,5-c]pyridine-4-carbonitrile;
- 6-{4-[3-(cis-3,5-dimethylpiperazin-1-yl)-propoxy]-3-(trifluoromethyl)-phenyl}-1-methyl-1H-imidazo[4,5-c]pyridine-4-carbonitrile;
- 1-methyl-6{4-[3-(4-methylpiperazin-1-yl)-propoxy]-3-(trifluoromethyl)-phenyl}-1H-imidazo[4,5-c]pyridine-4-carbonitrile;
- 6-{4-[3-(4-ethylpiperazin-1-yl)-propoxy]-3-(trifluoromethyl)-phenyl}-1-methyl-1H-imidazo[4,5-c]pyridine-4-carbonitrile;
- 1-methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile;
- 6-{4-[3-(2-ethyl-imidazol-1-yl)-propoxy]-3-(trifluoromethyl)-phenyl}-1-methyl-1H-imidazo[4,5-c]pyridine-4-carbonitrile;
- 6-{4-[2-(cis-3,5-dimethyl-piperazin-1-yl)-ethoxy]-3-(trifluoromethyl)-phenyl}-1-methyl-1H-imidazo[4,5-c]pyridine-4-carbonitrile;
- 1-methyl-6-{4-[2-(8-methyl-2,4-dioxo-1,3,8-triaza-spiro[4,5]dec-3-yl)-ethoxy]-3-(trifluoromethyl)-phenyl}-1H-imidazo[4,5-c]pyridine-4-carbonitrile;
- 1-methyl-6-[4-(pyridin-2-yl-methoxy)-3-(trifluoromethyl)-phenyl]-1H-imidazo-[4,5-c]pyridine-4-carbonitrile;
- 6-{4-[3-(4-ethyl-piperazin-1-yl)-propoxy]-3-(trifluoromethyl)-phenyl}-1H-imidazo-[4,5-c]pyridine-4-carbonitrile;
- 1-methyl-6-{3-(trifluoromethyl)-4-[(3-(S)-isopropylpiperazin-1-yl)-propoxy]-phenyl}-1H-imidazo[4,5-c]pyridine-4-carbonitrile hydrochloride;
- 6-(4-(2-(1-ethylpiperidin-4-yl)ethoxy)-3-(trifluoromethyl)phenyl)-1-methyl-1H-imidazo[4,5-c]pyridine-4-carbonitrile 2,2,2-trifluoroacetate; and
- 1-methyl-6-[4-(6-methyl-pyridin-2-ylmethoxy)-3-trifluoromethyl-phenyl]-1H-imidazo[4,5-c]pyridine-4-carbonitrile; or a pharmaceutically acceptable salt thereof.

The invention provides in a further aspect pharmaceutical compositions comprising a 6-phenyl-1H-imidazo[4,5-c]pyridine-4-carbonitrile derivative having general formula I, or a pharmaceutically acceptable salt thereof, in admixture with pharmaceutically acceptable auxilliaries.

The 6-phenyl-1H-imidazo[4,5-c]pyridine-4-carbonitrile derivatives of general Formula I where $R_2$ is H, may be prepared by the methods as depicted in Schemes 1, 2 and 3. Selective cyanation of 4-amino-2,6-dichloro-3-nitropyridine (II) (see Scheme 1) with copper cyanide produces 4-amino-6-chloro-2-cyano-3-nitropyridine (III), from which 6-chloro-3,4-diamino-pyridine-2-carbonitrile (VI) is generated following reduction of the nitro group by either hydrogenation (using Pd/C—$H_2$) or by the use of $SnCl_2$ or Fe based reducing agents.

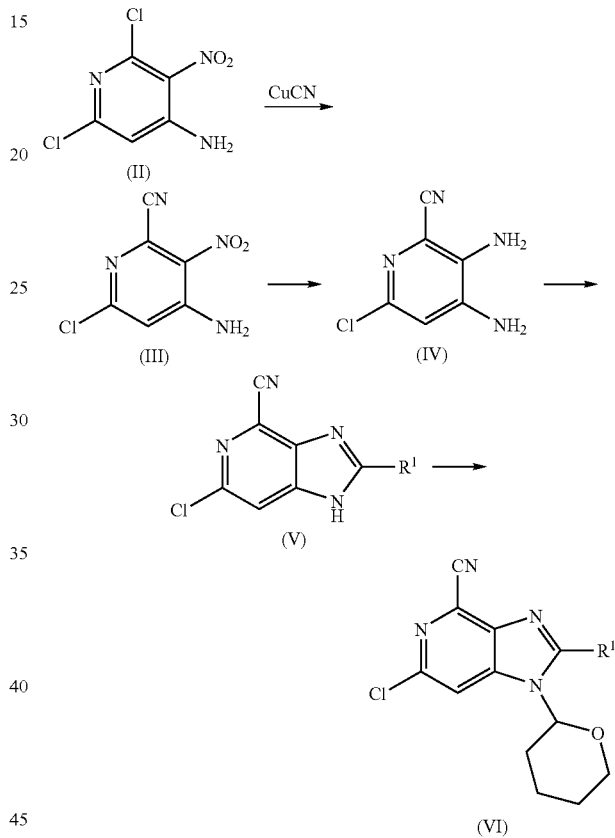

Cyclisation of the 3,4-diaminopyridine derivative (IV) with an orthoester catalysed by a Lewis acid, such as ytterbium triflate or a protonic acid, such as acetic acid provides the required imidazopyridine intermediate (V), wherein $R_1$ has the meaning as defined before. The imidazopyridine NH of compound (V) is then protected by a tetrahydropyranyl (THP) group to give compound (VI) in admixture with the $N^3$ substituted product. This mixture of regioisomers can be used without separation since on final removal of the THP protecting group both isomers will yield the same compound.

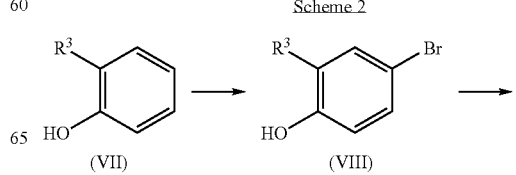

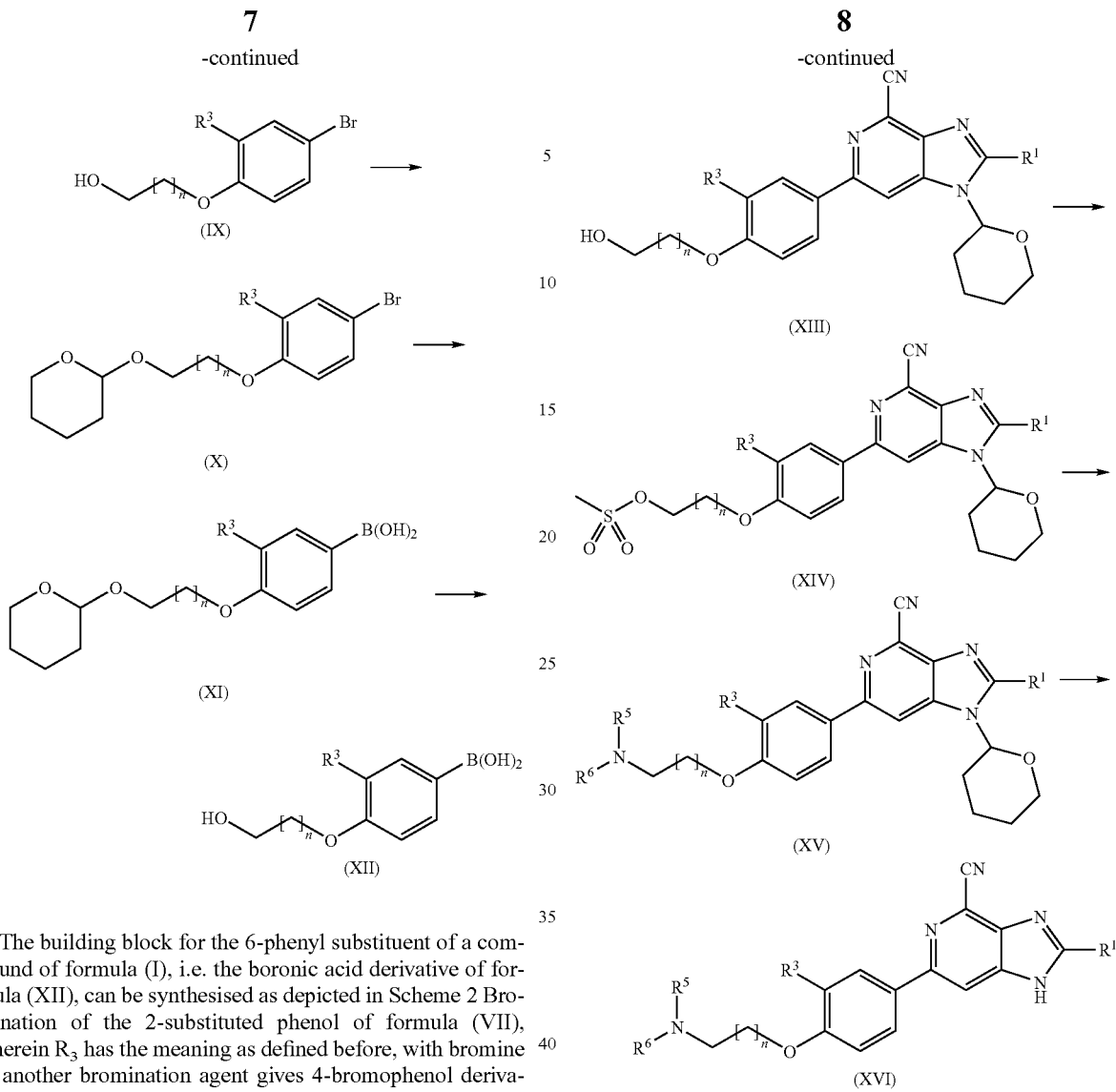

The building block for the 6-phenyl substituent of a compound of formula (I), i.e. the boronic acid derivative of formula (XII), can be synthesised as depicted in Scheme 2 Bromination of the 2-substituted phenol of formula (VII), wherein $R_3$ has the meaning as defined before, with bromine or another bromination agent gives 4-bromophenol derivatives (VIII) as product. Hydroxyalkylation of (VII) with hydroxyalkylhalides and potassium carbonate as base provides the compound of formula (IX), the hydroxy group of which is subsequently protected by a THP group under standard conditions to give a compound of formula (X). Lithiation of the latter with butyl lithium, followed by reaction with triisopropyl borate and work-up with diluted acetic acid in water gives the boronic acid derivatie of formula (XI) in high yield. The THP protecting group is then removed by heating a compound of formula (XI) in 1M hydrochloric acid in methanol to give the boronic acid derivative of formula (XII) in high yield.

Scheme 3

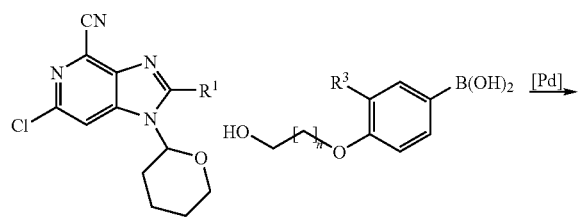

By using a palladium catalysed Suzuki coupling reaction between the key intermediates of formula VI (Scheme 1) and of formula (XII; see Scheme 2), as depicted in Scheme 3, a 6-phenyl-1H-imidazo[4,5-c]pyridine-4-carbonitrile derivative of formula (XIII) is obtained. Reaction of the alcohol function in these compounds with methanesulphonyl chloride in dichloromethane or tetrahydrofuran or NMP with triisopropylethylamine as base provides the methanesulphonate derivative of formula (XIV), from which on reaction with a secondary or primary amine or other neucleophiles a compound of formula (XV) is obtained. Removal of the tetrahydropyranyl protecting group affords a compound of formula (XVI), which is a compound of the invention according to formula I wherein Y is $NR_5R_6$ and X is O.

The 6-phenyl-1H-imidazo[4,5-c]pyridine-4-carbonitrile derivatives of general Formula I where $R_2$ is $(C_{1-3})$alkyl, can be prepared by the synthesis route depicted in Scheme 4. N-alkylation of 4-amino-6-chloro-2-cyano-3-nitropyridine (II) with the appropriate alkyl halide and a base, such as potassium carbonate, in a suitable solvent, such as acetonitrile or dimethyl formamide, gives a compound of formula (XVII) as product. Subsequent reduction of the nitro group by hydrogenation aided by palladium on charcoal or by using $SnCl_2$ or $Fe/H^+$, provides the compound of formula (XVIII) in high yield. Compound (XIX) was then prepared from compound (XVIII) by condensation with an orthoester catalysed by an acid such as acetic acid or ytterbium triflate at heated temperature. Suzuki coupling of a compound of formula (XIX) with a boronic acid derivative of formula (XII) gives a compound of formula (XX). From compound (XX), the methanesulphonate of formula (XXI) was then prepared and substitution of the sulphonate with an amine or other nitrogen neucleophiles provides a compound of formula (XXII), which is a compound according to formula (I) of the invention wherein Y is $NR_5R_6$ and X is O.

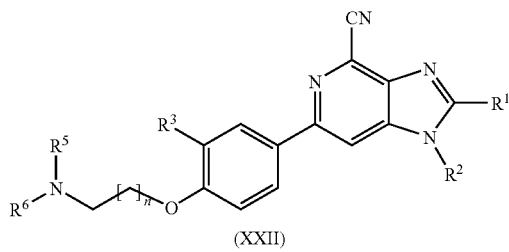

(XXII)

The 6-phenyl-1H-imidazo[4,5-c]pyridine-4-carbonitrile derivatives of general Formula I where X is a methylene ($CH_2$) can be prepared as depicted in Scheme 5.

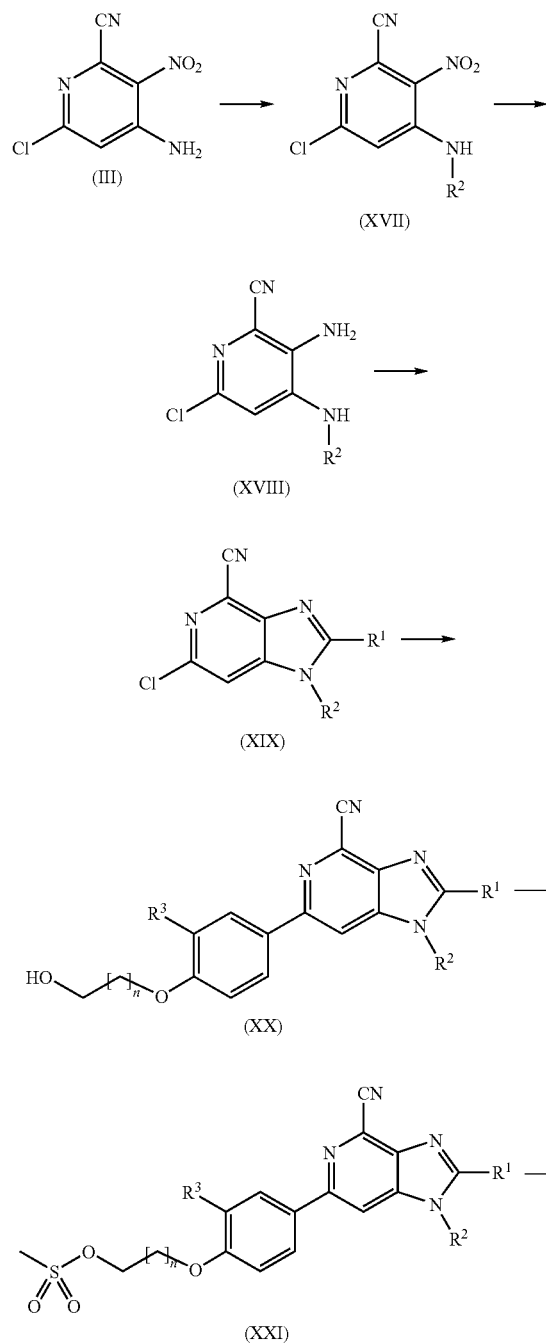

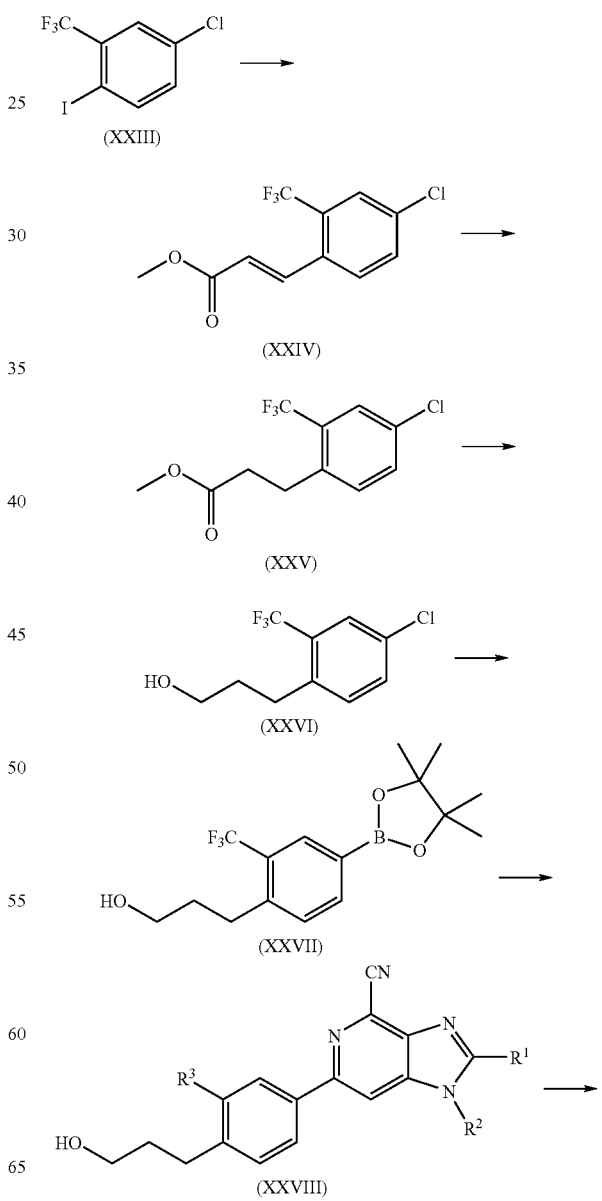

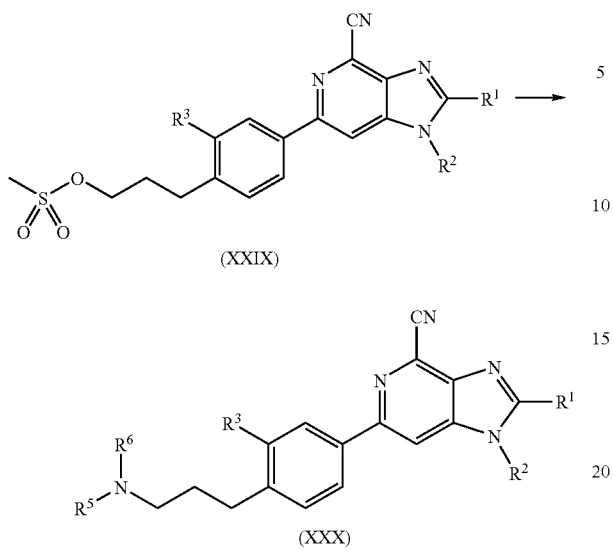

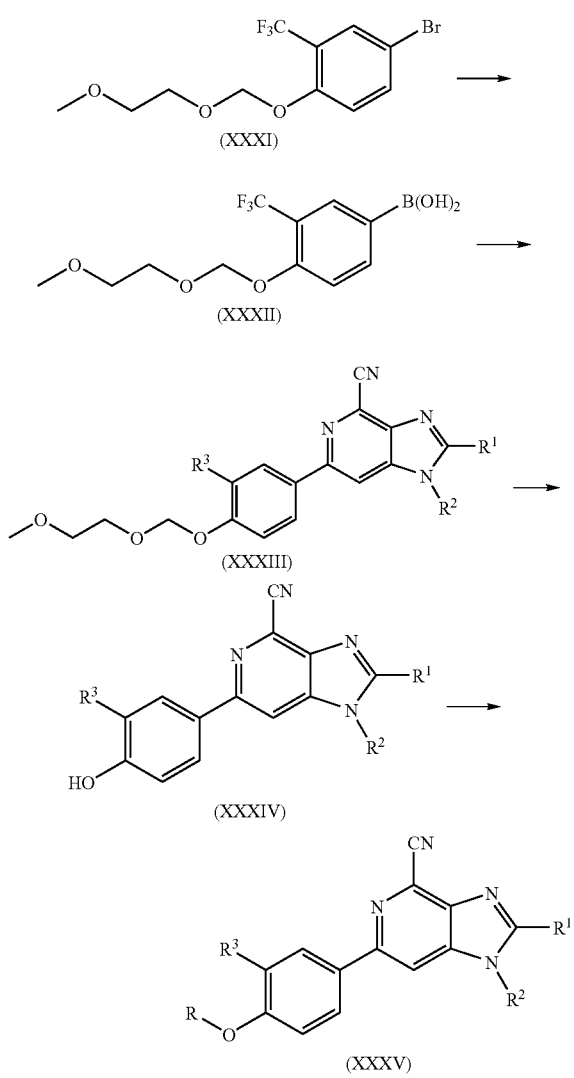

Heck reaction of 4-chloro-2-trifluoromethyl phenyl iodide with methyl acrylate using a palladium catalyst gives the substituted methyl cinnamate of formula (XXIV), which on hydrogenation with palladium on charcoal as the catalyst gives methyl 3-(4-chloro-2-trifluoromethylphenyl)propionate (XXV) in high yield, and which is then reduced by using diisobutylaluminium hydride to give the corresponding alcohol of formula (XXVI) which is subsequently converted to the corresponding boronic ester derivative of formula (XXVII). Suzuki coupling between (XXVII) and a compound of formula (XIX) gives a compound of formula (XXVIII) which can be converted to a methanesulphonate of formula (XXIX) and subsequently to a compound of the invention according to formula (XXX) using methods as previously described.

6-Phenyl-1H-imidazo[4,5-c]pyridine-4-carbonitrile derivatives of general Formula I of the invention can also be prepared via the intermediate phenol derivative of formula (XIV) as shown in Scheme 6. This intermediate is prepared starting from 4-bromo-2-trifluoromethylphenol (VIII): following protection of the phenolic hydroxy group as a methoxyethoxymethoxy (MEMO) ether (I) the compound is converted to the boronic acid derivative (formula (XXXII)) by the method as described above (Scheme 2). Subsequent Suzuki coupling with the compound of formula (XIX) gives the compound of formula (XXXIII), from which the MEMO group is then removed using dilute aqueous hydrochloric acid. The resulting intermediate compound of formula (XXXIV) can be derivatised by either alkylation, a Mitsunobu reaction or using further methods known in the art, to prepare additional compounds of formula (XXXV), wherein R represents Y—[CH$_2$]$_n$— or a precursor therefor.

For compound of formula (XXXV), wherein R contains a primary or secondary amine, an alcohol or a carboxylic acid, these functionalities may need to be temporarily protected. Suitable protecting groups are known in the art, for example from Wuts, P. G. M. and Greene, T. W.: *Protective Groups in Organic Synthesis*, Third Edition, Wiley, New York, 1999.

The resulting primary or secondary amine, alcohol or carboxylic acid can be then used for further derivatisation as shown by Scheme 7, such as alkylation or reductive alkylation.

Scheme 6

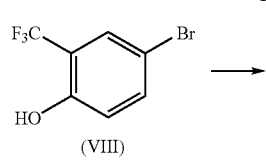

Scheme 7

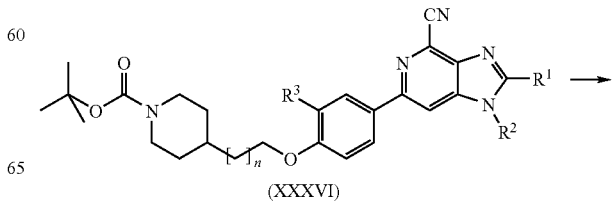

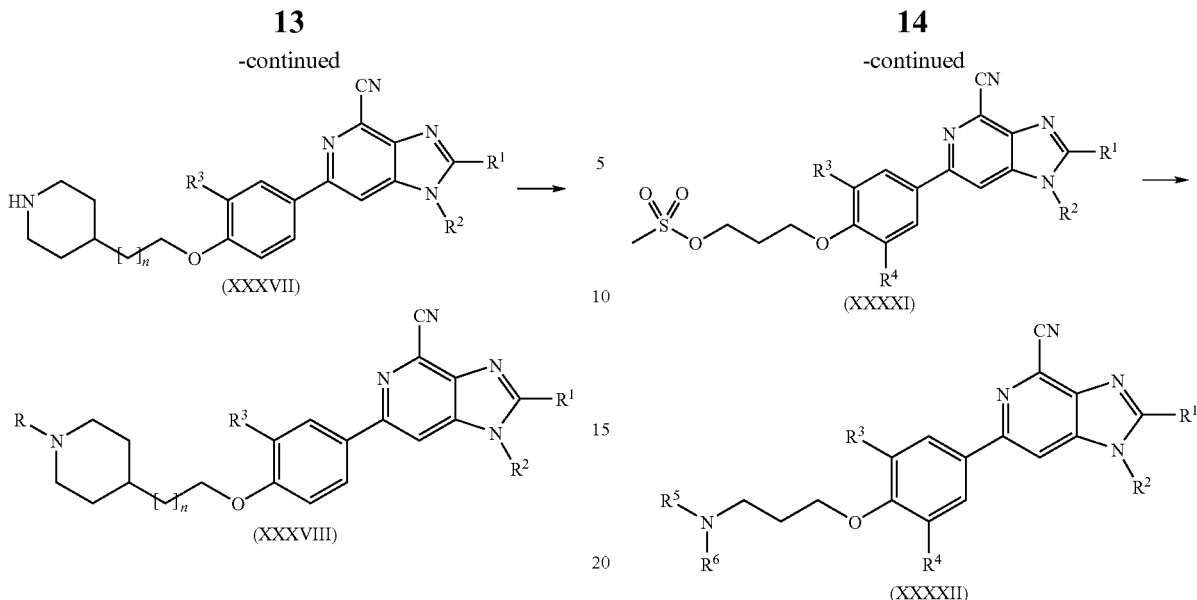

The 6-phenyl-1H-imidazo[4,5-c]pyridine-4-carbonitrile derivatives of general Formula I wherein $R_4$ is not a proton, may be prepared via an intermediate of formula (XXXIV) as shown in Scheme 8. Halogenation and cyanation of a compound of formula (XXXIV) at the $R_4$ position with corresponding reagents can be achieved using standard conditions from the literature to provide a compound of formula (XXXIX). Further derivatisation of (XXXIX) as shown in Scheme 8, and as detailed as above, leads to the required final product of formula (XXXII) via the intermediates of formula (XXXX) and (XXXXI).

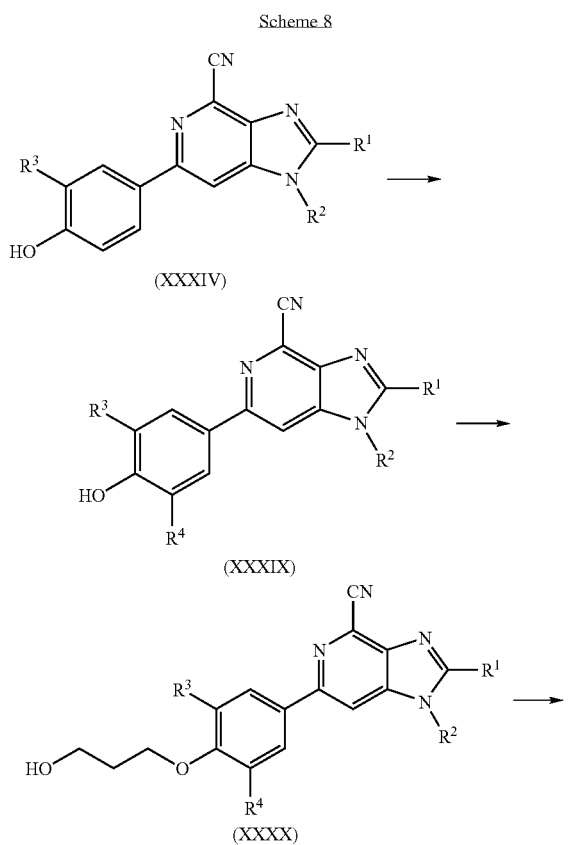

In the preparation of a 6-phenyl-1H-imidazo[4,5-c]pyridine-4-carbonitrile derivative of general Formula I in which the $R^1$ or the $R^2$ or the $R^4$ or the $R^5$ or the $R^6$ group contains a basic amino nitrogen atom, such a nitrogen is to be temporarily protected, such as for example by the acid labile t-butyloxycarbonyl (Boc) protecting group. Other suitable protecting groups for functional groups which are to be temporarily protected during syntheses, are known in the art, for example from Wuts, P. G. M. and Greene, T. W.: *Protective Groups in Organic Synthesis*, Third Edition, Wiley, New York, 1999.

The 6-phenyl-1H-imidazo[4,5-c]pyridine-4-carbonitrile derivatives of the invention, which can be in the form of a free base, may be isolated from the reaction mixture in the form of a pharmaceutically acceptable salt. The pharmaceutically acceptable salts, such as acid addition salts, may further be obtained by treating the free base of Formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid.

Suitable salts of 6-phenyl-1H-imidazo[4,5-c]pyridine-4-carbonitrile derivatives of Formula I in which a carboxylate group is present can be an alkali metal salts, such as sodium, potassium or lithium salt, or may be a salt obtained from the combination with an organic base, such as trimethylamine, triethylamine and the like.

Compounds of the invention may exist in solvated as well as in unsolvated forms, including hydrated forms. In general, the solvated forms are equivalent to unsolvated forms and are intended to be encompassed within the scope of the present invention.

Compounds of the present invention may exist as amorphous forms, but also multiple crystalline forms may be possible. In general, all physical forms are equivalent for the uses contemplated by the present invention and are intended to be within the scope of this invention.

The 6-phenyl-1H-imidazo[4,5-c]pyridine-4-carbonitrile derivatives of the invention and their salts may contain a centre of chirality in one or more of the side chains and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The compounds of the invention were found to be inhibitors of human Cathepsin S and of Cathepsin K and can therefore in a further aspect of the invention be used in therapy, and especially for the preparation of a medicament for the treatment of autoimmune disease, chronic obstructive pulmonary disease, pain, cancer, obesity, osteoporosis, atherosclerosis and related Cathepsin S and K dependent disorders, such as rheumatoid arthritis, psoriasis, asthma and IBD.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.
Methods
General Chemical Procedures.

All reagents were either purchased from common commercial sources or synthesised according to literature procedures using commercial sources. Proton NMR ($^1$H NMR) were obtained on a Bruker DPX 400 spectrometer and are referenced to internal tetramethylsilane (TMS). Mass spectra were recorded on a Shimadzu LC-8A (HPLC) PE Sciex API 150EX LCMS. Analytical reversed-phase LCMS analysis was carried out on LUNA C18 column (5 µm; 30×4.6 mm) under gradient conditions (90% water/0.1% formic acid to 90% acetonitrile/0.1% formic acid) at a flow rate of 4 ml/min,
Abbreviations Dimethylformamide (DMF), N-methylpyrrolidinone (NMP), dichloromethane (DCM), dimethylsulfoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), methanesulphonate (MsO), trifluoromethanesulphonate (TfO), methoxyethoxymethoxy (MEMO), tetrahydropyran (THP), N-chlorosuccinimide (NCS), strong cation exchange resin (SCX), strong anion exchange resin (SAX), deuteriated DMSO (DMSO), deuteriated methanol (CD3OD), deuteriated chloroform (CDCl3), methyl (Me), ethyl (Et), isopropyl (iPr).

EXAMPLE 1

6-[4-(3-Hydroxypropoxy)-3-(trifluoromethyl-phenyl]-1-methyl-1H-imidazo[4,5-c]pyridine-4-carbonitrile

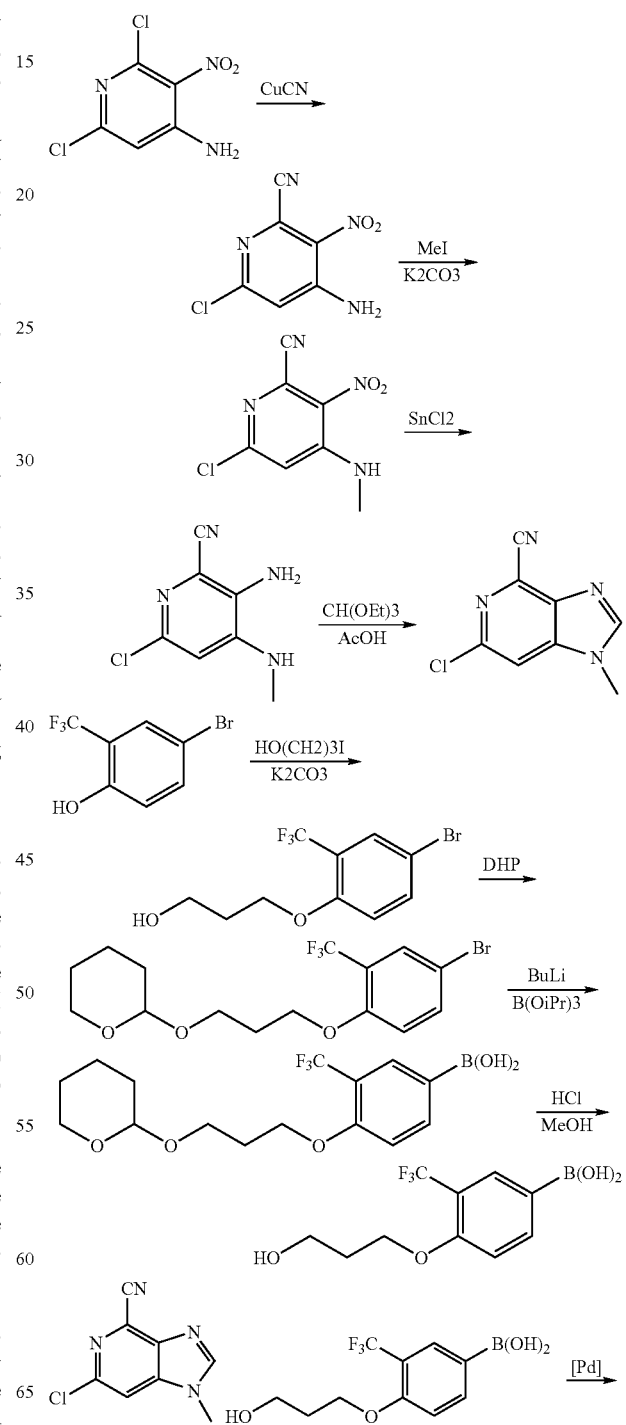

-continued

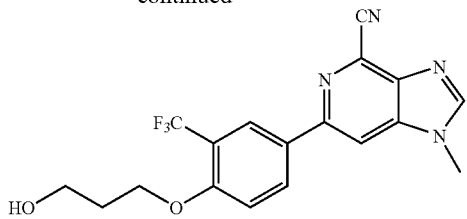

A: 4-Amino-6-chloro-3-nitro-pyridine-2-carbonitrile

A stirred suspension of 4-amino-2,6-dichloro-3-nitro-pyridine (17.5 g, 841 mmol) and copper (i) cyanide (15.1 g, 168.3 mmol) in 170 ml of 1-methyl-2-pyrrolidinone was lowered into an oil bath preheated to 180° C. and stirring continued for 12 minutes. The mixture was allowed to cool and diluted with ethyl acetate (700 ml) and water (700 ml) and the resultant suspension filtered. The organic layer was separated and further washed with water (500 ml) and 0.1N HCl (500 ml). The organic layer was then dried over sodium sulfate, filtered and concentrated under reduced pressure to give a brown solid which was washed with diethylether and dichloromethane to afford 4-amino-6-chloro-3-nitro-pyridine-2-carbonitrile (8 g).
$^1$H NMR (DMSO) δ: 8.8-7.7 (bs, 2H), 7.18 (s, 1H).

B: 6-Chloro-4-methylamino-3-nitro-pyridine-2-carbonitrile

A stirred mixture of 4-amino-6-chloro-3-nitro-pyridine-2-carbonitrile (12.5 g), potassium carbonate (17.4 g) and iodomethane (22.5 g) in acetonitrile (150 ml) was heated at 80° C. for 3 hours. At this point, another portion of iodomethane (22.5 g) was added; the mixture was heated with stirring for another 2 hours. The mixture was then diluted with ethyl acetate (500 ml) and washed with water (150 ml). The organic layer was then dried over sodium sulphate, solvent removed under reduced pressure to give expected product 4-methylamino-6-chloro-3-nitro-pyridine-2-carbonitrile (13 g).
$^1$H NMR (CD3OD) δ: 7.2 (s, 1H), 3.02 (s, 3H). MS m/z 213 (M+H).

C: 3-Amino-6-chloro-4-methylamino-pyridine-2-carbonitrile

Tin(II) chloride dihydrate (21 g) was added to a suspension of 6-chloro-4-methylamino-3-nitro-pyridine-2-carbonitrile (6.6 g) in ethanol (150 ml). The mixture was stirred at room temperature for 3 hours. To above red-brown coloured solution was then added ethyl acetate (1000 ml) and followed by 10% aqueous ammonium hydroxide (200 ml). The organic layer were separated, the sticky solid pad was washed with ethyl acetate (5×200 ml). Combined organic layer was then washed with saturated sodium chloride aqueous solution (2×200 ml), dried over sodium sulphate, solvent removed to give a brown solid as expected product (5.7 g).
$^1$H NMR (CD3OD) δ: 6.45 (s, 1H), 2.89 (s, 3H).

D: 6-Chloro-1-methyl-1H-imidazo[4,5-c]pyridine-4-carbonitrile

The suspension of 3-amino-6-chloro-4-methylamino-pyridine-2-carbonitrile (1.8 g) in DCM (5 ml), acetic acid (1.5 ml) and triethyl orthoformate (10 ml) was heated in microwave at 150° C. for 30 minutes. The mixture was then diluted with ethyl acetate (200 ml), washed with 10% sodium carbonate (100 ml), dried over sodium sulphate, solvent removed under reduced pressure, DCM (5 ml) was then added to the residue, some product crashed out and collected by filtration (0.5 g), the rest was then columned on silica gel using ethyl acetate-heptane (55:45) as eluant to give another 0.8 g expected product (a total of 1.3 g product).
$^1$H NMR (CDCl3) δ: 8.1 (s, 1H), 7.6 (s, 1H), 3.93 (s, 3H). MS m/z 193 (M+H).

E: 3-(4-Bromo-2-(trifluoromethyl)-phenoxy)propan-1-ol

3-Iodopropanol (11.23 g) was added to a mixture of 4-bromo-2-(trifluoromethyl)-phenol (15 g) and potassium carbonate (17.2 g) in acetonitrile (150 ml). The above mixture was refluxed for 4 hours then diluted with ethyl acetate (500 ml) and water (300 ml). Organic layer was separated, dried over magnesium sulphate, solvent removed under reduced pressure to give expected product clean enough for use at the next step (18.6 g).
$^1$H NMR (CDCl3) δ: 7.67 (d, 1H), 7.58 (dd, 1H), 6.90 (dd, 1H), 4.18 (t, 2H), 3.87 (q, 2H), 2.07 (tt, 2H).

F: 2-[3-(4-Bromo-2-(trifluoromethyl)-phenoxy)-propoxy]-tetrahydro-2H-pyran

A mixture of 3-(4-bromo-2-(trifluoromethyl)-phenoxy) propan-1-ol (12 g), 3,4-dihydro-2H-puran (6.75 g) and p-toluenesulfonic acid hydrate (0.76 g) in THF (100 ml) was stirred at room temperature for 1 hour then diluted with 10% sodium carbonate (50 ml) and extrated with ethyl acetate (2×150 ml). Organic layer was then dried over sodium sulphate, solvent removed under reduced pressure to give expected product (15 g).
$^1$H NMR(CDCl3) δ: 7.67 (d, 1H), 7.56 (dd, 1H), 6.90 (dd, 1H), 4.56 (dd, 1H), 4.15 (t, 2H), 3.75-4.0 (m, 2H), 3.4-3.65 (m, 2H), 2.10 (m, 2H), 1.4-2.0 (m, 6H).

G: 4-(3-(Tetrahydro-2H-pyran-2-yloxy)-propoxy)-3-(trifluoromethyl)-phenylboronic Acid BuLi (2.5M, 19.1 ml) was added dropwise to a solution of 2-(3-(4-bromo-2-(trifluoromethyl)phenoxy)propoxy)tetrahydro-2H-pyran (16.6 g) in THF at −78° C. under N2 during 3 minutes. After stirring at −78° C. for another 10 minutes, triisopropyl borate (11 ml) was then added dropwise during 3 minutes at −78° C. The mixture was stirred at −78° C. for further 20 minutes, then warmed up to room temperature slowly and stirred at room temperature for 30 minutes. The mixture was then quenched with acetic acid (10% in water, 20 ml), extracted with EtOAc (200 ml), washed with brine (100 ml×5), dried over sodium sulphate, solvent removed under reduced pressure, the residue was taken in to toluene and then solvent removed under vacuum to take out trace of acetic acid (repeat 3 times, until no acetic acid smell). The product shown by NMR contains 3 sets of product peaks assumed to be monomer, dimer and trimer.
$^1$H NMR (CDCl3) δ: 7.8-8.4 (3×s and 3×d, 2H), 6.9-7.2 (3×d, 1H), 4.6 (m, 1H), 3.4-4.3 (m, 6H), 2.1-2.3 (m, 2H), 1.4-1.9 (m, 6H).

H: 4-(3-Hydroxypropoxy)-3-(trifluoromethyl)-phenylboronic Acid 4-(3-(Tetrahydro-2H-pyran-2-yloxy)propoxy)-3-(trifluoromethyl)phenylboronic acid (30.6 g) was added to hydrochloric acid (1M in MeOH) and the mixture was heated at 50° C. for 40 minutes. Solvent and HCl were then removed under reduced pressure and residue (20.3 g) was used for next step without further purification. Proton NMR indicates 2 sets of product peaks assumed to be monomer and dimer or trimer.
$^1$H NMR (CDCl3 (0.7 ml)+CD3OD (0.2 ml)) δ: 7.7-8.0 (2×d and 2×s, 2H), 7.0 (2×d, 1H), 4.22 (t, 2H), 3.86 (t, 2H), 3.48 (tt, 2H).

I: 6-[4-(3-Hydroxypropoxy)-3-(trifluoromethyl)-phenyl]-1-methyl-1H-imidazo[4,5-c]pyridine-4-carbonitrile A mixture of 6-chloro-1-methyl-1H-imidazo[4,5-c]pyridine-4-carbonitrile (6 g), 4-(3-hydroxypropoxy)-3-(trifluoromethyl)phenylboronic acid (12.3 g), tris(dibenzylideneacetone)dipalladium (1.42 g), tricyclohexylphosphoine (1.05) and tribasic potassium phosphate (13.2 g) in dioxane (60 ml) and water (24 ml) was heated at 100° C. under N2 for 4 hours. The mixture was then diluted with ethyl acetate (400 ml) organic layer separated and solvent removed under reduced pressure, to the residue was then added methanol (50 ml), product crystalised out and collected by filtration (7.7 g).
$^1$H NMR (DMSO) δ: 8.67 (s, 1H), 8.60 (s, 1H), 8.43 (d, 1H), 8.37 (s, 1H, 7.41 (d, 1H), 4.55 (t, 1H), 4.25 (t, 2H), 3.99 (s, 3H), 3.58 (q, 2H), 1.92 (tt, 2H). MS m/z 377 (M+H).

EXAMPLE 2a

6-[4-(3-Dimethylaminopropoxy)-3-(trifluoromethyl)-phenyl]-1-methyl-1H-imidazo[4,5-g]pyridine-4-carbonitrile HCl salt

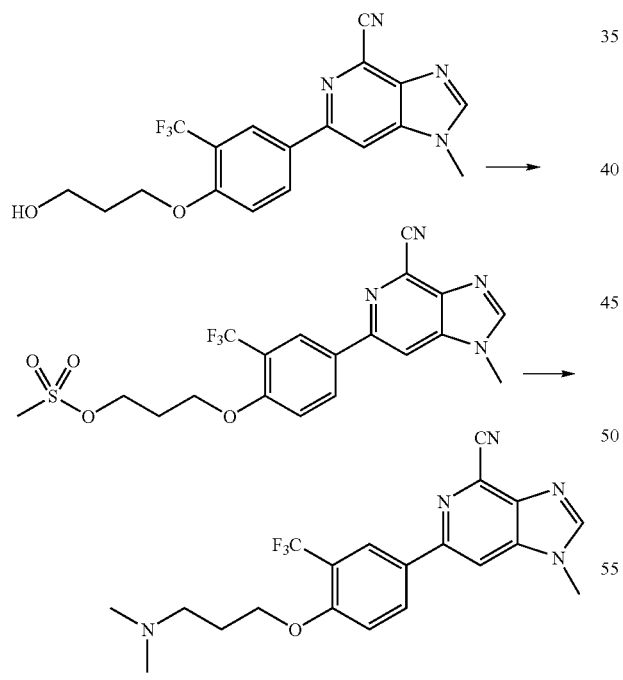

A: 3-[4-(4-Cyano-1-methyl-1H-imidazo[4,5-c]pyridin-6-yl)-2-(trifluoromethyl)phenoxy]propyl Methanesulfonate Methanesulphonyl chloride (2.65 g) was added dropwise to a solution of 6-[4-(3-hydroxypropoxy)-3-(trifluoromethyl)-phenyl]-1-methyl-1H-imidazo[4,5-c]pyridine-4-carbonitrile (6.7 g) and diisopropylethylamine (9.7 ml) in NMP (40 ml). The mixture was stirred at room temperature for 3 hours. After adding ice (100 g), solid product was collected by filtration, washed with cold ethanol (20 ml) to give 3-[4-(4-cyano-1-methyl-1H-imidazo[4,5-c]pyridin-6-yl)-2-(trifluoromethyl)phenoxy]propyl methanesulfonate (7.4 g).
$^1$H NMR (DMSO) δ: 8.69 (s, 1H), 8-62 (s, 1H), 8.45 (d, 1H), 8.41 (s, 1H), 7.47 (d, 1H), 4.40 (t, 1H), 4.32 (t, 2H), 3.99 (s, 3H), 3.18 (s, 3H), 2.21 (tt, 2H).

B: 6-[4-(3-Dimethylaminopropoxy)-3-(trifluoromethyl)-phenyl]-1-methyl-1H-imidazo[4,5-c]pyridine-4-carbonitrile HCl salt A mixture of 3-[4-(4-cyano-1-methyl-1H-imidazo[4,5-c]pyridin-6-yl)-2-(trifluoromethyl)phenoxy]propyl methanesulfonate (300 mg), and dimethylamine (2M in THF, 1.65 ml) in NMP (3 ml) was heated at 100° C. under microwave conditions for 20 minutes. The product was then purified by HPLC to give 6-[4-(3-dimethylaminopropoxy)-3-(trifluoromethyl)-phenyl]-1-methyl-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-[4-(3-dimethylaminopropoxy)-3-(trifluoromethyl)-phenyl]-1-methyl-1H-imidazo[4,5-c]pyridine-4-carbonitrile was then obtained. This free base was then dissolved in THF-MeOH (5:1, 4 ml) and 2M HCl in diethyl ether (1 ml) was then added. After removing of all solvent under reduced pressure, 6-[4-(3-dimethylaminopropoxy)-3-(trifluoromethyl)-phenyl]-1-methyl-1H-imidazo[4,5-c]pyridine-4-carbonitrile HCl salt (110 mg) was obtained as a white solid.
$^1$H NMR (CD3OD) δ: 8.52 (s, 1H), 8.62 (s, 1H), 8.35-8.45 (m, 3H), 7.36 (d, 1H), 4.35 (t, 2H), 4.04 (s, 3H), 3.39 (t, 2H), 2.97 (s, 6H), 2.33 (it, 2H). MS m/z 404 (M+H).

The procedure described in Example 2a was further applied, using the appropriate secondary amine derivatives, to prepare the following compounds as either TFA salt, free base or HCl salt:

2b; 1-Methyl-6-[4-(3-morpholin-4-ylpropoxy)-3-(trifluoromethyl)-phenyl]-1H-imidazo[4,5-c]pyridine-4-carbonitrile TFA salt

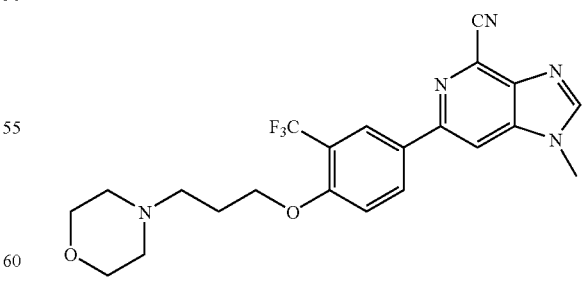

TFA $^1$H NMR (CD3OD) δ: 8.44 (s, 1H), 8.28-8.4 (m, 3H), 7.31 (d, 1H), 4.33 (t, 2H), 4.1 (br, 2H), 4.02 (s, 3H), 3.8 (br, 2H), 3.55 (br, 2H), 3.42 (t, 2H), 3.22 (br, 2H), 2.35 (tt, 2H). MS m/z 446 (M+1).

2c: 1-Methyl-6-[4-(3-pyrrolidin-1-ylpropoxy)-3-(trifluoromethyl)-phenyl]-1H-imidazo[4,5-c]pyridine-4-carbonitrile TFA salt ¹H NMR (CD3OD) δ: 8.44 (s, 1H), 8.3-8.4 (m, 3H), 7.32 (d, 1H), 4.32 (t, 2H), 4.02 (s, 3H), 3.7 (br, 2H), 3.45 (t, 2H), 3.15 (br, 2H), 2.32 (it, 2H), 2.2 (br, 2H), 2.1 (br, 2H). MS m/z 430 (M+H).

2d: 6-{4-[3-((S)-2-Hydroxymethyl-pyrrolidin-1-yl)-propoxy]-3-(trifluoromethyl)-phenyl}-1-methyl-1H-imidazo[4,5-c]pyridine-4-carbonitrile TFA salt ¹H NMR(CD3OD) δ: 8.44 (s, 1H), 8.3-8.4 (m, 3H), 7.30 (d, 1H), 4.30 (m, 2H), 4.02 (s, 3H), 3.91 (dd, 1H), 3.6-3.8 (m, 4H), 3.3 (m, 2H), 2.35 (m, 2H), 2.25 (m, 1H), 2.17 (m, 1H), 2.06 (m, 1H), 1.95 (m, 1H). MS m/z 460 (M+H).

2e: 6-{4-[3-((R)-2-Hydroxymethyl-pyrrolidin-1-yl)-propoxy]-3-(trifluoromethyl)-phenyl}-1-methyl-1H-imidazo[4,5-c]pyridine-4-carbonitrile TFA salt ¹H NMR (CD3OD) δ: 8.44 (s, 1H), 8.3-8.4 (m, 3H), 7.30 (d, 1H), 4.30 (m, 2H), 4.02 (s, 3H), 3.91 (dd, 1H), 3.6-3.8 (m, 4H), 3.3 (m, 2H), 2.35 (m, 2H), 2.25 (m, 1H), 2.17 (m, 1H), 2.06 (m, 1H), 1.95 (m, 1H). MS m/z 460 (M+H).

2f: 1-Methyl-6-{4-[3-(4-methylpiperidin-1-yl-propoxy]-3-(trifluoro methyl)-phenyl}-1H-imidazo[4,5-c]pyridine-4-carbonitrile TFA salt ¹H NMR (CD3OD) δ: 8.44 (s, 1H), 8.3-8.4 (m, 3H), 7.30 (d, 1H), 4.31 (t, 2H), 4.02 (s, 3H), 3.61 (brd, 2H), 3.32 (t, 2H), 3.02 (tbr, 2H), 2.3 (tt, 2H), 1.95 (dbr, 2H), 1.74 (m, 1H), 1.47 (m, 2H), 1.0 (d, 3H). MS m/z 458 (M+H).

2g: 6-{4-[3-(N-ethyl-N-methylamino)-propoxy]-3-(trifluoromethyl)-phenyl}-1-methyl-1H-imidazo[4,5-c]pyridine-4-carbonitrile TFA salt ¹H NMR (CD3OD) δ: 8.44 (s, 1H), 8.3-8.4 (m, 3H), 7.32 (d, 1H), 4.32 (t, 2H), 4.02 (s, 3H), 3.47 (m, 1H), 3.2-3.4 (m, 3H), 2.94 (s, 3H), 2.33 (m, 2H), 1.38 (t, 3H). MS m/z 418 (M+H).

2h: 6-{4-[3-(N-isopropyl-N-methylamino)-propoxy]-3-(trifluoromethyl)-phenyl}-1-methyl-1H-imidazo[4,5-c]pyridine-4-carbonitrile TFA salt ¹H NMR (CD3OD) δ: 8.45 (s, 1H), 8.3-8.4 (m, 3H), 7.31 (d, 1H), 4.32 (t, 2H), 4.02 (s, 3H), 3.69 (m, 1H), 3.5 (m, 1H), 3.3 (m, 1H), 2.87 (s, 3H), 2.3 (m, 2H), 1.40 (d, 3H), 1.38 (d, 3H). MS m/z 432 (M+H).

2i: 6-{4-[3-(N-cyclohexyl-N-methylamino)propoxy]-3-(trifluoromethyl)-phenyl}-1-methyl-1H-imidazo[4,5-c]pyridine-4-carbonitrile TFA salt ¹H NMR (CD3OD) δ: 8.45 (s 1H), 8.3-8.4 (m, 3H), 7.31 (d, 1H), 4.32 (t, 2H), 4.02 (s, 3H), 3.5 (m, 1H), 3.3 (m, 2H), 2.9 (s, 3H), 2.3 (m, 2H), 2.1 (m, 2H), 1.95 (m, 2H), 1.75 (m, 1H), 1.2-1.65 (m, 5H). MS m/z 472 (M+H).

2j: 6-{4-[3-(4-Hydroxypiperidin-1-yl)-propoxy]-3-(trifluoromethyl)-phenyl}-1-methyl-1H-imidazo[4,5-c]pyridine-4-carbonitrile TFA salt ¹H NMR (CD3OD) δ: 8.45 (s, 1H), 8.3-8.4 (m, 3H), 7.32 (d, 1H), 4.32 (t, 2H), 4.1 (t 0.5H), 4.02 (s, 3H), 3.85 (m, 0.5H), 3.66 (m, 1H), 3.45 (m, 1H), 3.35 (m, 3H), 3.12 (tbr, 1H), 2.35 (m, 2H), 2.2 (m, 1H), 2.0 (m, 2H), 1.75 (m, 1H). MS m/z 460 (M+H).

2k: 6-{4-[3-(N-isopropyl-N-2-methoxyethylamino)-propoxy]-3-(trifluoromethyl)-phenyl}-1-methyl-1H-imidazo[4,5-c]pyridine-4-carbonitrile TFA salt ¹H NMR (CD3OD) δ: 8.45 (s, 1H), 8.35-8.45 (m, 3H), 7.34 (d, 1 h), 4.33 (t, 2H), 4.03 (s, 3H), 3.65-3.9 (m, 3H), 3.25-3.55 (m, 4H), 3.46 (overlaps with m Hs, s, 3H), 2.35 (m, 2H), 1.40 (d, 6H). MS m/z 476 (M+H).

2l: 6-{4-[3-(N,N-bis(2-methoxyethyl)amino)-propoxy]-3-(trifluoromethyl)-phenyl}-1-methyl-1H-imidazo[4,5-c]pyridine-4-carbonitrile TFA salt ¹H NMR (CD3OD) δ: 8.44 (s, 1H), 8.3-8.4 (m, 3H), 7.31 (d, 1H), 4.32 (t, 2H), 4.02 (s, 3H), 3.77 (t, 4H), 3.5-3.65 (m, 6H), 3.42 (s, 6H), 2.33 (m, 2H). MS m/z 492 (M+H).

2m: 6-{-4-[3-(N-2-hydroxyethyl-N-isopropylamino)-propoxy]-3-(trifluoromethyl)-phenyl}-1-methyl-1H-imidazo[4,5-c]pyridine-4-carbon trite TFA salt ¹H NMR (CD3OD) δ: 8.45 (s, 1H), 8.35-8.45 (m, 3H), 7.33 (d, 1H), 4.33 (t, 2H), 4.02 (s, 3H), 3.75-3.95 (m, 3H), 3.35-3.5 (m, 3H), 3.25 (m, 1H), 2.35 (m, 2H), 1.41 (d, 6H). MS m/z 462 (M+H).

2n: 6-{4-[3-(Cis-2,6-dimethylmorpholin-4-yl)-propoxy]-3-(trifluoromethyl)-phenyl}-1-methyl-1H-imidazo[4,5-c]pyridine-4-carbonitrile TFA Sail ¹H NMR (CD3OD) δ: 8.44 (s, 1H), 8.28-8.4 (m, 3H), 7.31 (d, 1H), 4.32 (t, 2H), 4.02 (s, 3H), 3.9 (m, 2H), 3.56 (d, 2H), 3.4 (t, 2H), 2.78 (t, 2H), 2.36 (m, 2H), 1.27 (d, 6H). MS m/z 474 (M+1).

2o: 6-{4-[3-(4-oxo-imidazolidin-1-yl)-propoxy]-3-trifluoromethyl)-phenyl}-1-methyl-1H-imidazo[4,5-c]pyridine-4-carbonitrile TFA salt ¹H NMR (CD3OD) δ: 8.44 (s, 1H), 8.28-8.4 (m, 3H), 7.31 (d, 1H), 4.32 (t, 2H) 4.02 (s, 3H), 3.97 (s, 2H), 3.55 (t, 2H), 2.32 (m, 2H). MS m/z 445 (M+1).

2p: 6-{4-[3-(1-oxo-2,8-diaza-spiro[4,5]dec-8-yl)-propoxy]-3-(trifluoromethyl)-phenyl}-1-methyl-1H-imidazo[4,5-c]pyridine-4-carbonitrile TFA salt

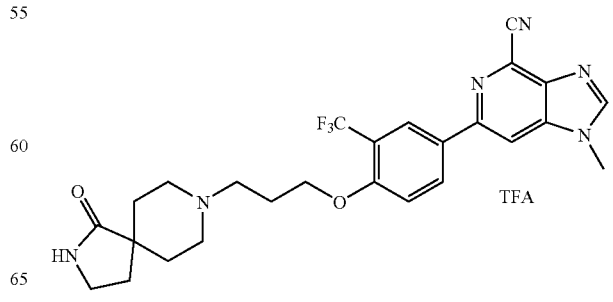

¹H NMR (CD3OD) δ: 8.45 (s, 1H), 8.3-8.4 (m, 3H), 7.33 (d, 1H), 4.33 (t, 2H), 4.02 (s, 3H), 3.7 (m, 2H), 3.55 (m, 1H), 3.4 (m, 3H), 3.15 (m, 1H), 2.37 (m, 2H), 1.8-2.3 (m, 6H). MS m/z 513 (M+H).

2q: 6-{4-[3-(2,4-Dioxo-1,3,8-triaza-spiro[4,5]dec-8-yl)-propoxy]-3-trifluoromethyl)-phenyl}-methyl-1H-imidazo[4,5-c]pyridine-4-carbonitrile TFA salt

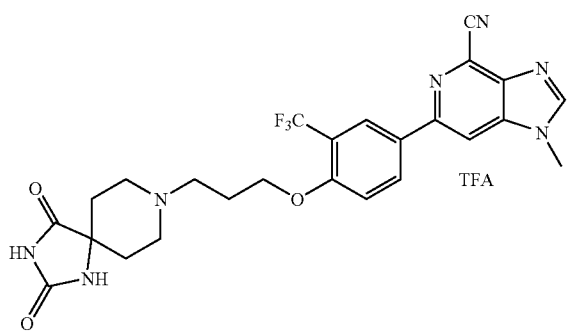

¹H NMR (CD3OD) δ: 8.46 (s, 1H), 8.35-8.45 (m, 3H), 7.36 (d, 1H), 4.34 (t, 2H), 4.03 (s, 3H), 3.6-3.85 (m, 2H), 3.45 (m, 1H), 3.2 (m, 1H), 2.35 (m, 3H), 2.1 (m, 1H). MS m/z 528 (M+H).

2r: 1-Methyl-6-{4-[3-(5-oxo-[1,4]diazepan-1-yl)-propoxy]-3-(trifluoromethyl)-phenyl}-1H-imidazo[4,5-c]pyridine-4-carbonitrile TFA salt ¹H NMR (CD3OD) δ: 2.36 (m, 2H), 2.86 (m, 2H), 3.38-3.62 (bm, 4H), 3.44 (t, 2H), 3.58 (m, 2H), 4.02 (s, 3H), 4.33 (t, 2H), 7.35 (d, 1H), 8.39 (m, 1H), 8.40 (s, 2H), 8.45 (s, 1H). MS m/z 473 (M+1).

2s: 1-Methyl-6-{4-[3-(2-methyl-1-oxo-2,8-diaza-spiro[4.5]dec-8-yl)-propoxy]-3-(trifluoromethyl)-phenyl}-1H-imidazo[4,5-c]pyridine-4-carbonitrile TFA salt

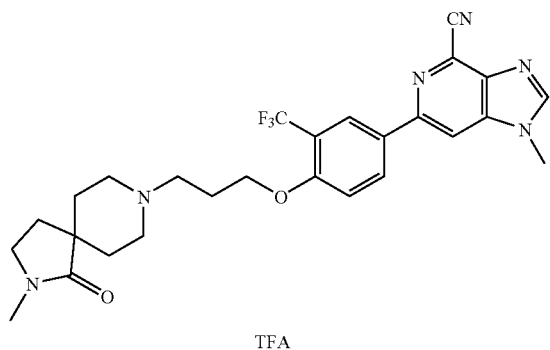

¹H NMR (CD3OD) δ: 1.74-2.22 (bm, 6H), 2.35 (m, 2H), 2.86 (s, 3H), 3.15 (m, 1H), 3.34-3.56 (bm, 5H), 3.62-3.78 (bm, 2H), 4.02 (s, 3H), 4.33 (t, 2H), 7.35 (d, 1H), 8.37 (m, 1H), 8.40 (s, 2H), 8.45 (s, 1H). MS m/z 527 (M+1).

2t: 1-Methyl-6-{4-[3-((R)-2-methyl piperidin-1-yl)-propoxy]-3-(trifluoromethyl)-1-phenyl}-1H-imidazo[4,5-c]pyridine-4-carbonitrile TFA salt

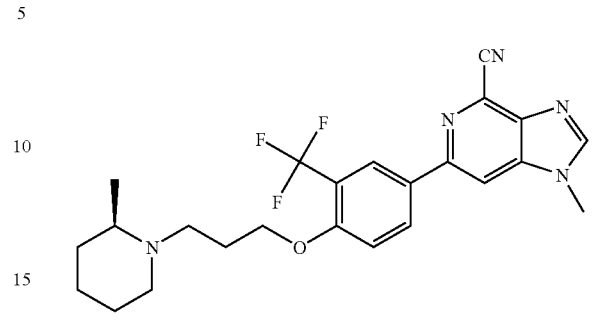

¹H NMR (CD3OD) δ: 8.43 (s, 1H), 8.34 (broad s, 3H), 7.30 (d, 1H), 4.32 (m, 2H), 4.01 (s, 3H), 3.75 (m, 0.5H), 3.60 (m, 2H), 3.35 (m, 1H), 3.30 (m, 0.5H), 3.12 (m, 1H), 2.35 (m, 1H), 2.25 (m, 1H), 2.02 (m, 2H), 1.80 (m, 2H), 1.65 (m, 2H), 1.44 (d, 2H), 1.40 (d, 1H). MS m/z 458 (M+1).

2u: 6-[4-(3-N,N-Diethylamino-propoxy)-3-(trifluoromethyl)-phenyl]-1-methyl-1H-imidazo[4,5-d]pyridine-4-carbonitrile HCl salt

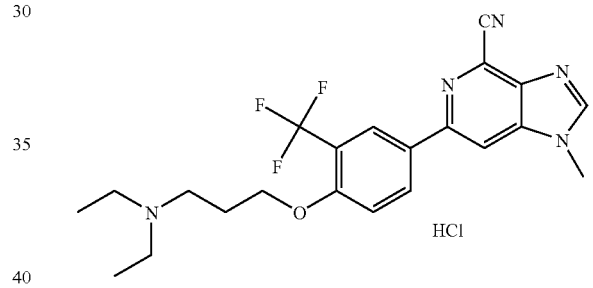

¹H NMR (CD3OD) δ: 8.76 (s, 1H), 8.51 (s, 1H), 8.43 (s, 1H), 8.41 (d, 1H), 7.37 (d, 1H), 4.34 (t, 2H), 4.08 (s, 3H), 3.41 (t, 2H), 3.31 (q, 4H), 2.30 (m, 2H), 1.38 (t, 6H). MS m/z 432 (M+1).

The procedure described in Example 2a was further applied, using the appropriate primary amine derivatives, to prepare the following compounds as either TFA salt, neutral compound or HCl salt:

EXAMPLE 3a

3a: 6-[4-(3-N-methylamino-propoxy)-3-(trifluoromethyl)-phenyl]-1-methyl-1H-imidazo[4,5-c]pyridine-4-carbonitrile TFA salt ¹H NMR (CD3OD) δ: 8.44 (s, 1H), 8.28-8.4 (m, 3H), 7.31 (d, 1H), 4.32 (t, 2H), 4.02 (s, 3H), 3.25 (t, 2H), 2.78 (s, 3H), 2.28 (m, 2H). MS m/z 390 (M+1).

3b: 6-[4-(3-N-cylobutylamino-propoxy)-3-(trifluoromethyl)-phenyl-]1-methyl-1H-imidazo[4,5-c]pyridine-4-carbonitrile TFA salt ¹H NMR (CD3OD) δ: 8.44 (s, 1H), 8.28-8.4 (m, 3H), 7.31 (d, 1H), 4.32 (t, 2H), 4.02 (s, 3H), 3.85 (m, 1H), 3.17 (t, 2H), 2.47 (m, 2H), 2.15-2.31 (m, 4H), 1.95 (m, 2H). MS m/z 430 (M+1).

3c: 6-{4-[3-(2,2-Difluoro-ethylamino)-propoxy]-3-(trifluoromethyl)-phenyl}1-methyl-1H-imidazo[4,5-c]pyridine-4-carbonitrile TFA salt $^1$H NMR (CD3OD) δ: 2.32 (m, 2H), 3.38 (m, 2H), 3.49 (q, 2H), 3.64 (t, 2H), 4.00 (s, 3H), 4.38 (t, 2H), 6.30 (m, 3H), 7.35 (d, 1H), 8.39 (dd, 1H), 8.40 (s, 2H), 8.45 (s, 1H). MS m/z 440 (M+1).

3d: 1-Methyl-6-(4-{3-[(pyridin-2-ylmethyl)-amino]-propoxy}-3-(trifluoromethyl)-phenyl)-1H-imidazo[4,5-c]pyridine-4-carbonitrile TFA salt $^1$H NMR (CD3OD) δ: 2.35 (m, 2H), 3.38 (m, 2H), 4.02 (s, 3H), 4.35 (t, 2H), 4.45 (s, 2H), 7.34 (d, 1H), 7.42 (m, 1H), 7.48 (d, 1H), 7.87 (m, 1H), 8.37 (dd, 1H), 8.38 (s, 2H), 8.44 (s, 1H), 8.62 (d, 1H) MS m/z 467 (M+1).

3e: 6-{4-[3-((R)-sec-Butylamino)-propoxy]-3-(trifluoro methyl)-phenyl}-1-methyl-1H-imidazo[4,5-c]pyridine-4-carbonitrile TFA salt $^1$H NMR (CD3OD) δ: 1.04 (t, 3H), 1.35 (d, 3H), 1.60 (m, 1H), 1.70 (m, 1H), 2.27 (m, 2H), 3.26 (m, 3H), 4.02 (s, 3H), 4.34 (t, 2H), 7.34 (d, 1H), 8.38 (dd, 1H), 8.39 (s, 2H), 8.45 (s, 1H). MS m/z 432 (M+1).

3f: 6-{4-[3-((R)-2-Hydroxy-propylamino)-propoxy]-3-(trifluoromethyl)-phenyl}-1-methyl-1H-imidazo[4,5-c]pyridine-4-carbonitrile TEA salt $^1$H NMR (CD3OD) δ: 1.25 (d, 3H), 2.30 (m, 2H), 3.05 (dd, 2H), 3.31 (m, 2H), 4.02 (s, 3H), 4.05 (m, 1H), 4.33 (t, 2H), 7.33 (d, 1H), 8.37 (dd, 1H), 8.38 (s, 2H), 8.45 (s, 1H). MS m/z 434.5 (M+1).

3g: 6-{4-[3-((S)-2-Methoxy-1-methyl-ethylamino)-propoxy]-3-(trifluoromethyl)-phenyl}-1-methyl-1H-imidazo[4,5-c]pyridine-4-carbonitrile TFA salt $^1$H NMR (CD3OD) δ: 1.37 (d, 3H), 2.28 (m, 2H), 3.31 (m, 2H), 3.43 (s, 3H), 3.46-3.56 (m, 2H), 3.67 (dd, 1H), 4.02 (s, 3H), 4.33 (t, 2H), 7.33 (d, 1H), 8.37 (dd, 1H), 8.38 (s, 2H), 8.45 (s, 1H). MS m/z 448 (M+1).

3h: 1-Methyl-6-{4-[3-(1-methyl-piperidin-4-ylamino)-propoxy]-3-(trifluoromethyl)-phenyl}-1H-imidazo[4,5-c]pyridine-4-carbonitrile TFA salt

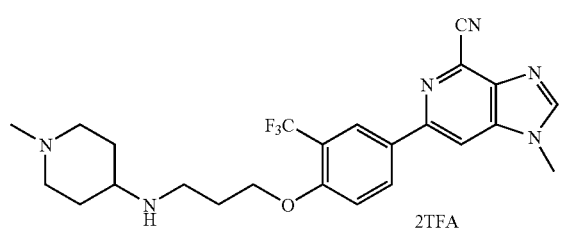

$^1$H NMR (CD3OD) δ: 2.00 (m, 2H), 2.30 (m, 2H), 2.41 (m, 2H), 2.91 (s, 3H), 3.07-3.22 (m, 2H), 3.35 (m, 2H), 3.53 (m, 1H), 3.68 (m, 2H), 4.02 (s, 3H), 4.34 (t, 2H), 7.33 (d, 1H), 8.37 (dd, 1H), 8.39 (s, 2H), 8.45 (s, 1H). MS m/z 473 (M+1).

3i: 1-Methyl-6-[4-(3-{[(S)-1-(tetrahydro-furan-2-yl)methyl]-amino}-propoxy)-3-(trifluoromethyl)-phenyl-1H-imidazo[4,5-c]pyridine-4-carbonitrile TFA salt $^1$H NMR (CD3OD) δ: 1.65 (m, 1H), 1.98 (m, 2H), 2.15 (m, 1H), 2.29 (m, 2H), 3.00-3.26 (m, 2H), 3.31 (m, 2H), 3.83 (m, 1H), 3.94 (m, 1H), 4.02 (s, 3H), 4.17 (m, 1H), 4.33 (t, 2H), 7.33 (d, 1H), 8.37 (dd, 1H), 8.38 (s, 2H), 8.44 (s, 1H). MS m/z 460 (M+1).

3j: 6-(4-{3-[(1-Hydroxy-cyclopropylmethyl)-amino]-propoxy}-3-(trifluoromethyl)-phenyl)-1-methyl-1H-imidazo[4,5-c]pyridine-4-carbonitrile TFA salt $^1$H NMR (CD3OD) δ: 0.74 (t, 1H), 0.91 (t, 1H), 2.32 (m, 2H), 2.97 (s, 2H), 3.35 (m, 2H), 4.02 (s, 3H), 4.34 (m, 2H), 7.35 (d, 1H), 8.39 (dd, 1H), 8.40 (s, 2H), 8.45 (s, 1H). MS m/446 (M+1).

3k: 6-{4-[3-(4-Hydroxy-cyclohexylamino)-propoxy]-3-(trifluoromethyl)-phenyl}-1-methyl-1H-imidazo[4,5-c]pyridine-4-carbonitrile TFA salt $^1$H NMR (CD3OD) δ: 1.32-1.52 (m, 4H), 2.07 (m, 2H), 2.16 (m, 2H), 2.26 (m, 2H), 3.13 (m, 1H), 3.30 (m, 2H), 3.57 (m, 1H), 4.02 (s, 3H), 4.36 (t, 2H), 7.35 (d, 1H), 8.39 (dd, 1H), 8.41 (s, 2H), 8.45 (s, 1H). MS m/z 474 (M+1).

EXAMPLE 4a

1-Methyl-6-{3-(trifluoromethyl)-4-[3-(3,3,4-trimethylpiperazin-1-yl)-propoxy]-phenyl}-1H-imidazo[4,5-c]pyridine-4-carbonitrile Hydrochloride

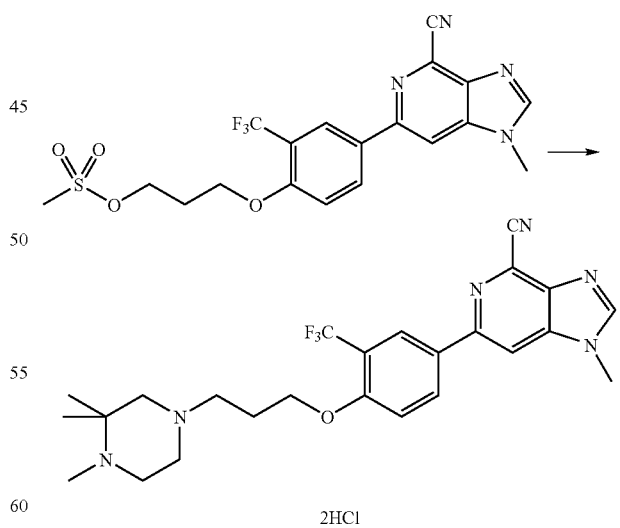

A mixture of 3-(4-(4-cyano-1-methyl-1H-imidazo[4,5-c]pyridin-6-yl)-2-(trifluoromethyl)phenoxy)propyl methanesulfonate (200 mg), and 1,2,2-trimethyl-piperazine (226 mg) in NMP (2 ml) was heated at 120° C. under microwave conditions for 20 minutes. The product was then purified by HPLC to give 1-methyl-6-{3-(trifluoromethyl)-4-[3-(3,3,4-trimethylpiperazin-1-yl)-propoxy]-phenyl}-1H-imidazo[4,5-c]pyridine-4-carbonitrile as a TFA salt. The above TFA salt was then dissolved in MeOH (3 ml) and passed through a strong cation exchange column. After washing with methanol to remove TFA residue, product was washed out with 2M ammonia in methanol. After removal of solvent, the free base of 1-methyl-6-{3-(trifluoromethyl)-4-[3-(3,3,4-trimethylpiperazin-1-yl)-propoxy]-phenyl}-1H-imidazo[4,5-c]pyridine-4-carbonitrile was then obtained. This free base was then dissolved in THF-MeOH (5:1, 4 ml) and 2M HCl in diethyl ether (1 ml) was added. After removing all solvent under reduced pressure, 1-methyl-6-{3-(trifluoromethyl)-4-[3-(3,3,4-trimethylpiperazin-1-yl)-propoxy]-phenyl}-1H-imidazo[4,5-c]pyridine-4-carbonitrile hydrochloride (125 mg) was obtained as a white solid.

$^1$H NMR (CD3OD) δ: 8.73 (s, 1H), 8.50 (s, 1H), 8.42 (s, 1H), 8.40 (d, 1H), 7.38 (d, 1H), 4.35 (t, 2H), 4.08 (s, 3H), 3.2-4.0 (br, 4H, piperazine ring Hs), 3.7 (sbr, 2H), 3.45 (t, 2H), 2.93 (s, 3H), 2.4 (m, 2H), 1.62 (s, 6H). MS m/z 487 (M+H).

The procedure described in Example 4a was further applied, using the appropriate piperazine derivatives, to prepare the following compounds as either TFA salt, free base or HCl salt:

4b: 6-{4-[3-(3,3-Dimethylpiperazin-1-yl)-propoxy]-3-(trifluoromethyl)-phenyl}-1-methyl-1H-imidazo[4,5-c]pyridine-4-carbonitrile Hydrochloride This reaction was carried out at room temperature for 72 hours.

$^1$H NMR (CD3OD) δ: 8.64 (s, 1H), 8.46 (s, 1H), 8.42 (s, 1H), 8.40 (d, 1H), 7.38 (d, 1H), 4.36 (t, 2H), 4.06 (s, 3H), 3.66 (sbr, 2H), 3.45 (t, 2H), 3.3-3.7 (br, 4H, piperazine ring Hs), 2.45 (m, 2H), 1.62 (s, 6H). MS m/z 473 (M+H).

4c: 6-{4-[3-(Cis-3,5-dimethylpiperazin-1-yl)-3-propoxy]-3-(trifluoromethyl)-phenyl}-1-methyl-1H-imidazo[4,5-c]pyridine-4-carbonitrile Hydrochloride This reaction was carried out at room temperature for 72 hours.

$^1$H NMR (CD3OD) δ: 8.64 (s, 1H), 8.47 (s, 1H), 8.44 (s, 1H), 8.42 (d, 1H), 7.40 (d, 1H), 4.40 (t, 2H), 4.08 (s, 3H), 3.95 (d, 2H), 3.90 (m, 2H), 3.56 (t, 2H), 3.27 (m, 2H), 2.48 (m, 2H), 1.51 (d, 6H). MS m/z 473 (M+H).

4d: 1-Methyl-6-{4-[3-(piperazin-1-yl)-propoxy]-3-(trifluoromethyl)-phenyl}-1H-imidazo[4,5-c]pyridine-4-carbonitrile Hydrochloride This reaction was carried out at room temperature for 72 hours.

$^1$H NMR (CD3OD) δ: 8.85 (s, 1H), 8.53 (s, 1H), 8.42 (s, 1H), 8.40 (d, 1H), 7.39 (d, 1H), 4.38 (t, 2H), 4.10 (s, 3H), 3.7 (br, 2H), 3.55 (t, 2H), 3.2-4.0 (br, 8H, piperazine Hs), 2.45 (m, 2H). MS m/z 445 (M+H).

4e: 1-Methyl-6-{4-[3-(4-methylpiperazin-1-yl)-propoxy]-3-(trifluoromethyl)-phenyl}-1H-imidazo[4,5-c]pyridine-4-carbonitrile Hydrochloride $^1$H NMR (CD3OD) δ: 8.59 (s, 1H), 8.45 (s, 1H), 8.42 (s, 1H), 8.40 (d, 1H), 7.39 (d, 1H), 4.37 (t, 2H), 4.05 (s, 3H), 3.2-4.1 (br, 8H, piperazine Hs), 3.5 (m, 2H), 3.05 (s, 3H), 2.45 (m, 2H). MS m/z 459 (M+H).

4f: 6-{4-[3-(4-Ethylpiperazin-1-yl)-proxy]-3-(trifluoromethyl)-phenyl}-1-methyl-1H-imidazo[4,5-c]pyridine-4-carbonitrile Hydrochloride $^1$H NMR (CD3OD) δ: 8.84 (s, 1H), 8.52 (s, 1H), 8.41 (s, 1H), 8.40 (d, 1H), 7.39 (d, 1H), 4.38 (t, 2H), 4.10 (s, 3H), 3.2-4.1 (br, 8H, piperazine Hs), 3.55 (t, 2H), 3.40 (q, 2H), 2.45 (m, 2H), 1.44 (t, 3H). MS m/z 473 (M+H).

4g: 6-(4-{3-[4-(2-hydroxyethyl)-piperazin-1-yl]-propoxy}-3-(trifluoromethyl)-phenyl)-1-methyl-1H-imidazo[4,5-c]pyridine-4-carbonitrile Hydrochloride $^1$H NMR (CD3OD) δ: 8.71 (s, 1H), 8.49 (s, 1H), 8.42 (s, 1H), 8.40 (d, 1H), 7.39 (d, 1H), 4.38 (t, 2H), 4.07 (s, 3H), 3.96 (m, 2H), 3.2-4.1 (br, 8H, piperazine Hs), 3.54 (t, 2H), 3.47 (m, 2H), 2.45 (m, 2H). MS m/z 489 (M+H).

4h: 1-Methyl-6-(4-{3-[4-(2-methoxyethyl)-piperazin-1-yl]-propoxy}-3-(trifluoromethyl)-phenyl)-1H-imidazo[4,5-c]pyridine-4-carbonitrile TFA salt $^1$H NMR (CD3OD) δ: 8.44 (s, 1H), 8.3-8.4 (m, 3H), 7.32 (d, 1H), 4.30 (t, 2H), 4.02 (s, 3H), 3.71 (t, 2H), 3.45 (m, 2H), 3.40 (s, 3H), 3.2-3.5 (br, 8H), 3.17 (t, 2H), 2.25 (m, 2H). MS m/z 503 (M+H).

4i: 6-{4-[3-(4-Isopropylpiperazin-1-yl)-propoxy]-3-(trifluoromethyl)-phenyl}-1-methyl-1H-imidazo[4,5-c]pyridine-4-carbonitrile TFA salt $^1$H NMR (CD3OD) δ: 8.44 (s, 1H), 8.3-8.4 (m, 3H), 7.30 (d, 1H), 4.31 (t, 2H), 4.02 (s, 3H), 3.3-3.7 (br, 9H, piperazine Hs+i-PrCH), 3.23 (t, 2H), 2.30 (m, 2H), 1.40 (d, 6H). MS m/z 487 (M+H).

4j: 1-Methyl-6-(4-{3-[4-(2-methoxyethyl)-piperazin-1-yl]-propoxy}-3-(trifluoromethyl)-phenyl)-1H-imidazo[4,5-c]pyridine-4-carbonitrile TFA salt $^1$H NMR (CD3OD) δ: 8.44 (s, 1H), 8.3-8.4 (m, 3H), 7.32 (d, 1H), 4.30 (t, 2H), 4.02 (s, 3H), 3.71 (t, 2H), 3.45 (m, 2H), 3.40 (s, 3H), 3.2-3.5 (br, 8H), 3.17 (t, 2H), 2.25 (m, 2H). MS m/z 503 (M+H).

4k: 1-Methyl-6-(4-{3-[4-(2-oxo-2-pyrrolidin-1-yl-ethyl)-piperazin-1-yl]-propoxy}-3-(trifluoromethyl)-phenyl)-1H-imidazo[4,5-c]pyridine-4-carbonitrile TFA salt $^1$H NMR (CD3OD) δ: 8.45 (s, 1H), 8.3-8.4 (m, 3H), 7.30 (d, 1H), 4.32 (m, 2H), 4.02 (s, 3H), 3.76 (s, 2H), 3.45 (q, 4H), 3.40 (m, 5H), 3.31 (m, 5H), 2.3 (m, 2H), 2.0 (m, 2H), 1.9 (m, 2H). MS m/z 556 (M+H).

4l: 1-Methyl-6-{4-[3-(4-pyrimidin-2-yl-piperazin-1-yl)-propoxy]-3-(trifluoromethyl)-phenyl}-1H-imidazo[4,5-c]pyridine-4-carbonitrile TFA salt $^1$H NMR (CD3OD) δ: 8.44 (s, 1H), 8.42 (d, 2H), 8.3-8.4 (m, 3H), 7.33 (d, 1H), 6.74 (t, 1H), 4.34 (t, 2H), 4.02 (s, 3H), 3.0-3.7 (br, 8H, piperazine Hs), 3.45 (t, 2H), 2.37 (m, 2H). MS m/z 523 (M+H).

4m: 1-Methyl-6-{4-[3-(4-pyridin-2-yl-piperazin-1-yl)-propoxy]-3-(trifluoromethyl)-phenyl}-1H-imidazo[4,5-c]pyridine-4-carbonitrile TFA salt $^1$H NMR (CD3OD) δ: 8.46 (s, 1H), 8.35-8.45 (m, 3H), 8.17 (dd, 1H), 7.80 (t, 1H), 7.37 (d, 1H), 7.10 (d, 1H), 6.91 (t, 1H), 4.36 (t, 2H), 4.03 (s, 3H), 3.7-4.1 (br, 8H, piperazine Hs), 3.45 (t, 2H), 2.40 (m, 2H). MS m/z 522 (M+H).

4n: 1-Methyl-6-{4-[3-(3-oxo-piperazin-1-yl)-propoxy]-3-(trifluoromethyl)-phenyl}-1H-imidazo[4,5-c]pyridine-4-carbonitrile ¹H NMR (DMSO) δ: 8.46 (s, 1H), 8.69 (s, 1H), 8.62 (s, 1H), 8.35-8.5 (m, 2H), 7.52 (d, 1H), 4.25 (t, 2H), 3.99 (s, 3H), 3.2 (br, 2H), 2.98 (br, 2H), 2.6 (br, 4H), 2.0 (br, 2H). MS m/z 459 (M+H).

4o: 6-{4-[3-(4-acetylpiperazin-1-yl)-propoxy]-3-(trifluoromethyl)-phenyl}-1-methyl-1H-imidazo[4,5-c]pyridine-4-carbonitrile TFA salt ¹H NMR (CD3OD) δ: 8.43 (s, 1H) δ: 8.43 (s, 1H), 8.3-8.4 (m, 3H), 7.28 (d, 1H), 4.32 (t, 2H), 4.01 (s, 3H), 3.1-3.7 (br, 8H, piperazine Hs), 3.45 (t, 2H), 2.38 (m, 2H), 2.17 (s, 3H). MS m/z 487 (M+H).

4p: 6-(4-{3-[4-(ethoxycarbonyl)piperazin-1-yl]-propoxy}-3-(trifluoromethyl)-phenyl)-1-methyl-1H-imidazo[4,5-c]pyridine-4-carbonitrile TFA salt ¹H NMR (CD3OD) δ: 8.44 (s, 1H), 8.3-8.4 (m, 3H), 7.30 (d, 1H), 4.32 (t, 2H), 4.19 (q, 2H), 4.02 (s, 3H), 3.1-3.7 (br, 8H, piperazine Hs), 3.43 (t, 2H), 2.38 (m, 2H), 1.29 (t, 3H). MS m/z 517 (M+H).

4q: 6-(4-{3-[4-(Dimethylaminocarbonyl)-piperazin-1-yl]propoxy}-3-(trifluoromethyl)-phenyl)-1-methyl-1H-imidazo[4,5-c]pyridine-4-carbonitrile TFA salt ¹H NMR (CD3OD) δ: 2.36 (m, 2H), 2.91 (s, 6H), 3.29-3.32 (m, 7H), 3.43 (m, 3H), 4.02 (s, 3H), 4.33 (t, 2H), 7.33 (d, 1H), 8.37 (m, 1H), 8.38 (s, 2H), 8.45 (s, 1H). MS m/z 516 (M+1).

4r: 1-Methyl-6-{4-[3-(4-pyridin-4-yl-piperazin-1-yl)-propoxy-3-(trifluoromethyl)-phenyl}-1H-imidazo[4,5-c]pyridine-4-carbonitrile TFA salt ¹H NMR (CD3OD) δ: 2.39 (m, 2H), 3.44 (m, 2H), 3.54 (bs, 4H), 4.02 (s, 3H), 4.07 (bs, 4H), 4.36 (t, 2H), 7.31 (d, 2H), 7.35 (d, 1H), 8.27 (d, 2H), 8.39 (dd, 1H), 8.41 (s, 2H), 8.45 (s, 1H). MS m/z 522 (M+1).

4s: 1-Methyl-6-{4-[3-(6-methyl-6,9-diaza-spiro[4.5]dec-9-yl)-propoxy]-3-(trifluoromethyl)-phenyl}-1H-imidazo[4,5-c]pyridine-4-carbonitrile TFA salt

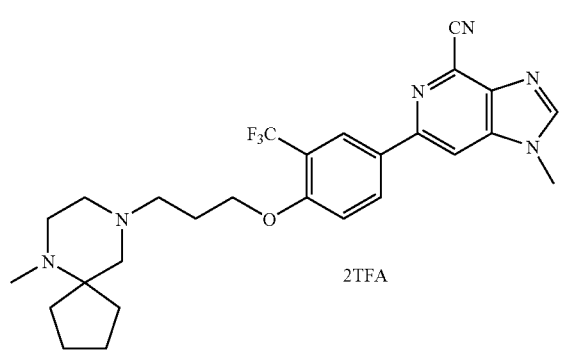

2TFA

¹H NMR (CD3OD) δ: 1.62-1.84 (bm, 4H), 1.84-2.02 (bm, 4H), 2.08 (m, 2H), 2.58-3.00 (bm, 6H), 2.73 (t, 2H), 2.82 (s, 3H), 4.02 (s, 3H), 4.28 (t, 2H), 7.33 (d, 1H), 8.36 (dd, 1H), 8.39 (s, 2H), 8.45 (s, 1H). MS m/z 513 (M+1).

4t: 6-{4-[(R)-3-(Hexahydro-pyrrolo[1,2-a]pyrazin-2-yl)-propoxy]-3-(trifluoromethyl)-phenyl}-1-methyl-1H-imidazo[4,5-c]pyridine-4-carbonitrile TFA salt

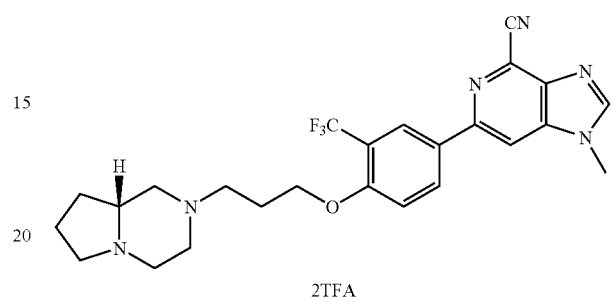

2TFA

¹H NMR (CD3OD) δ: 1.88 (m, 1H), 2.08-2.30 (bm, 5H), 2.80 (t, 1H), 2.95 (t, 1H), 3.06 (m, 2H), 3.18 (m, 1H), 3.30 (m, 2H), 3.40-3.65 (bm, 4H), 4.02 (s, 3H), 4.30 (t, 2H), 7.32 (d, 1H), 8.35 (m, 1H), 8.38 (s, 2H), 8.45 (s, 1H). MS m/z 485 (M+1).

EXAMPLE 5a

1-Methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile Hydrochloride A mixture of 3-[4-(4-cyano-1-methyl-1H-imidazo[4,5-c]pyridin-6-yl)-2-(trifluoromethyl)phenoxy)propyl methanesulfonate (83 mg), and N-methyl piperidine-4-carboxamide (78 mg) in NMP (1 ml) was heated at 120° C. under microwave conditions for 20 minutes. The product was then purified by HPLC to give expected product, 1-methyl-6-(4-{3-[4-(N-methylaminocarbonyl)-piperidin-1-yl]-propoxy}-3-

(trifluoromethyl)-phenyl)-1H-imidazo[4,5-c]pyridine-4-carbonitrile as a TFA salt. The above TFA salt was then dissolved in MeOH (3 ml) and passed through a strong cation exchange column. After washing with methanol to remove TFA residue, product was washed out with 2M ammonia in methanol. After removal of solvent, the free base of 1-methyl-6-(4-{3-[4-(N-methylaminocarbonyl)-piperidin-1-yl-propoxy}-3-(trifluoromethyl)-phenyl)-1H-imidazo[4,5-c]pyridine-4-carbonitrile was then obtained. This free base was dissolved in THF-MeOH (5:1, 4 ml) and 2M HCl in diethyl ether (1 ml) was then added. After removing all solvent under reduced pressure, 1-methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile hydrochloride (64 mg) was obtained as a white solid. $^1$H NMR (CD3OD) δ: 8.66 (s, 1H), 8.48 (s, 1H), 8.42 (s, 1H), 8.40 (d, 1H), 7.33 (d, 1H), 4.33 (t, 2H), 4.06 (s, 3H), 3.70 (dbr, 2H), 3.49 (br, 1H), 3.37 (t, 2H), 3.08 (t, 2H), 2.74 (s, 3H), 2.55 (m, 1H), 2.35 (m, 2H), 2.1 (m, 2H), 2.0 (m, 2H). MS m/z 501 (M+H).

The procedure described in Example 5a was further applied, using the appropriate amine derivatives, to prepare the following compounds as either TFA salt, free base or HCl salt:

5b: 6-(4-{3-[(R)-2-(Aminocarbonyl)-pyrrolidin-1-yl]-propoxy}-3-(trifluoromethyl)-phenyl)-1-methyl-1H-imidazo[4,5-c]pyridine-4-carbonitrile TFA salt $^1$H NMR (DMSO) δ: 8.71 (s, 1H), 8.64 (s, 1H), 8.48 (d, 1H), 8.42 (s, 1H), 8.12 (s, 1H), 7.88 (s, 1H), 7.42 (d, 1H), 4.35 (m, 2H), 4.12 (m, 1H), 3.99 (s, 3H), 3.69 (broad m, 1H), 3.38 (broad m, 2H), 3.25 (broad m, 1H), 2.49 (m, 1H), 2.18 (m, 2H), 2.08 (m, 1H), 1.88 (m, 2H). MS m/z 473 (M+1).

EXAMPLE 6a 6-(4-{3-[N-(2-Dimethylaminoethyl)-N-methylamino]-propoxy}-3-(trifluoromethyl)-phenyl)-1-methyl-1H-imidazo[4,5-c]pyridine-4-carbonitrile TFA salt

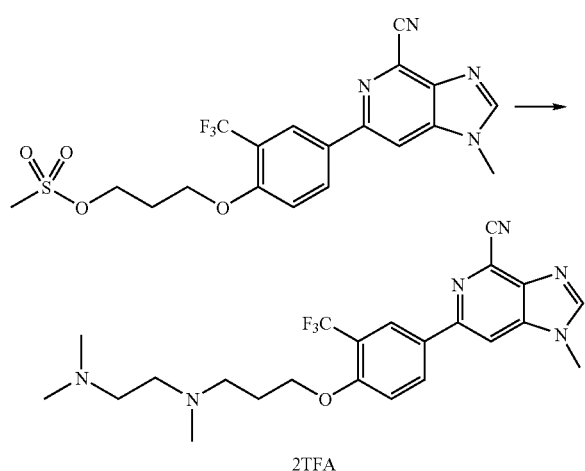

A mixture of 3-(4-(4-cyano-1-methyl-1H-imidazo[4,5-c]pyridin-6-yl)-2-(trifluoromethyl)phenoxy)propyl methanesulfonate (20 mg), and N,N',N'-trimethylethylenediamine (22 mg) in NMP (1 ml) was heated at 100° C. under microwave conditions for 20 minutes. The product was then purified by HPLC to give 6-(4-{3-[N-(2-dimethylaminoethyl)-N-methylamino]-propoxy}-3-(trifluoromethyl)-phenyl)-1-methyl-1H-imidazo[4,5-c]pyridine-4-carbonitrile as a TFA salt.

$^1$H NMR (CD3OD) δ: 8.45 (s, 1H), 8.28-8.38 (m, 3H), 7.30 (d, 1H), 4.32 (t, 2H), 4.02 (s, 3H), 3.70 (m, 4H), 3.48 (t, 2H), 3.03 (s, 3H), 2.98 (s, 6H), 2.39 (m, 2H). MS m/z 461 (M+H).

The procedure described in Example 6a was further applied, using the appropriate bisamine derivatives, to prepare the following compounds as either TFA salt, free base or HCl salt:

6b: 1-Methyl-6-(4-{3-[N-(2-morpholin-4-yl-ethyl)-amino]-propoxy}-3-(trifluoromethyl)-phenyl)-1H-imidazo[4,5-c]pyridine-4-carbonitrile TFA salt

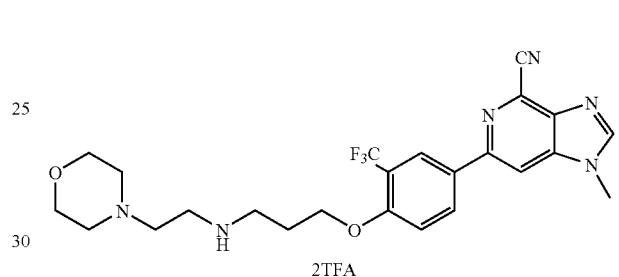

$^1$H NMR (CD3OD) δ: 8.44 (s, 1H), 8.25-8.38 (m, 3H), 7.29 (d, 1H), 4.33 (t, 2H), 4.01 (s, 3H), 3.94 (t, 4H), 3.58 (t, 2H), 3.51 (t, 2H), 3.3-3.45 (m, 6H), 2.32 (m, 2H). MS m/z 489 (M+H).

6c: 1-Methyl-6-(4-{3-[4-(pyrrolidin-1-yl)-piperadin-1-yl]-propoxy}-3-(trifluoromethyl)-phenyl)-1H-imidazo[4,5-c]pyridine-4-carbonitrile TFA salt $^1$H NMR (CD3OD) δ: 8.45 (s, 1H), 8.35-8.43 (m, 3H), 7.32 (d, 1H), 4.33 (t, 2H), 4.03 (s, 3H), 3.7 (m, 2H), 3.48 (m, 1H), 3.38 (t, 2H), 3.7 (br, 2H), 3.15 (br, 4H), 2.5 (m, 2H), 2.35 (m, 2H), 2.0-2.3 (m, 6H). MS m/z 513 (M+H).

6d: 6-[4-(3-[1,4]Diazepan-1-yl-propoxy)-3-(trifluoromethyl)-phenyl]-1-methyl-1H-imidazo[4,5-c]pyridine-4-carbonitrile TFA salt $^1$H NMR (CD3OD) δ: 8.33-8.45 (m, 4H), 7.32 (d, 1H), 4.34 (t, 2H), 4.02 (s, 3H). 3.76 (m, 2H), 3.68 (m, 2H), 3.57 (m, 2H), 3.47 (4H), 2.35 (m, 4H). MS m/z 459 (M+H).

6e: 1-Methyl-6-{4-[3-(4-methyl-[1,4]diazepan-1-yl)-propoxy]-3-(trifluoromethyl)-phenyl}-1H-imidazo[4,5-c]pyridine-4-carbonitrile TFA salt $^1$H NMR (CD3OD) δ: 2.33 (m, 4H), 2.99 (s, 3H), 3.40 (t, 2H), 3.51 (bs, 4H), 3.75 (s, 4H), 4.02 (s, 3H), 4.33 (t, 2H), 7.34 (d, 1H), 8.37 (dd, 1H), 8.39 (s, 2H), 8.45 (s, 1H).

MS m/z 473 (M+1).

6f: 6-{4-[(1R,5S)-3-(3,8-Diaza-bicyclo[3.2.1]oct-3-yl)-propoxy]-3-(trifluoromethyl)-phenyl}-1-methyl-1H-imidazo[4,5-c]pyridine-4-carbonitrile TFA salt

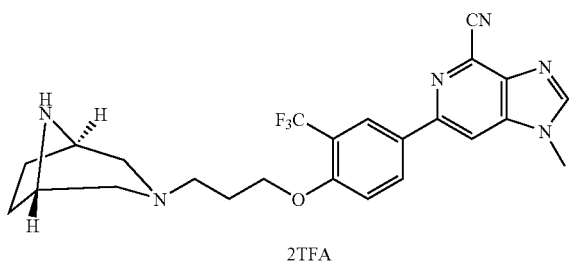

¹H NMR (CD3OD) δ: 2.01 (m, 4H), 2.10 (m, 2H), 2.48 (d, 2H), 2.68 (t, 2H), 2.93 (d, 2H), 3.99 (bs, 2H), 4.03 (s, 3H), 4.28 (t, 2H), 7.34 (d, 1H), 8.37 (m, 1H), 8.39 (s, 2H), 8.44 (s, 1H). MS m/z 471 (M+1).

6g: 6-{4-[3-((S)-3-Dimethylamino-pyrrolidin-1-yl)-propoxy]-3-(trifluoromethyl)-phenyl}1-methyl-1H-imidazo[4,5-c]pyridine-4-carbonitrile TFA salt ¹H NMR (CD3OD) δ: 2.35 (m, 3H), 2.66 (m, 1H), 2.98 (s, 6H), 3.30 (m, 2H), 3.50 (m, 2H), 3.70-4.00 (bm, 2H), 4.02 (s, 3H), 4.18 (m, 1H), 4.33 (t, 2H), 7.33 (d, 1H), 8.36 (m, 1H), 8.38 (s, 2H), 8.45 (s, 1H). MS m/z 473 (M+1).

6h: 6-{4-[3-((R)-3-Dimethylamino-pyrrolidin-1-yl)-propoxy]-3-(trifluoromethyl)-phenyl}-1-methyl-1H-imidazo[4,5-c]pyridine-4-carbonitrile TFA salt ¹H NMR (CD3OD) δ: 2.35 (m, 3H), 2.66 (m, 1H), 2.96 (s, 6H), 3.30 (m, 2H), 3.50 (m, 2H), 3.70-4.00 (bm, 2H), 4.02 (s, 3H), 4.18 (m, 1H), 4.33 (t, 2H), 7.33 (d, 1H), 8.36 (dd, 1H), 8.38 (s, 2H), 8.45 (s, 1H). MS m/z 473 (M+1).

EXAMPLE 7a

1-Methyl-6-{4-[3-(2-methyl-imidazol-1-yl)-propoxy]-3-(trifluoromethyl)-phenyl}-1H-imidazo[4,5-c]pyridine-4-carbonitrile TFA salt

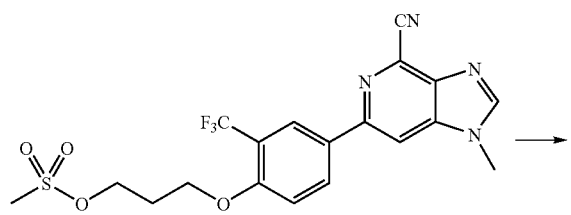

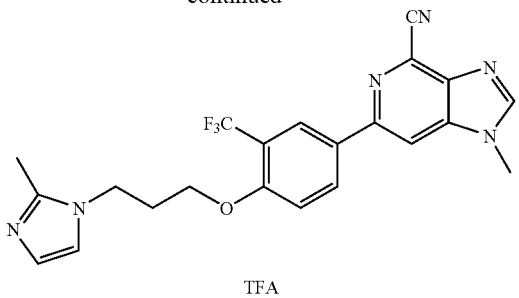

A mixture of 3-(4-(4-cyano-1-methyl-1H-imidazo[4,5-c]pyridin-6-yl)-2-(trifluoromethyl)phenoxy)propyl methanesulfonate (20 mg), and 2-methylimidazole (22 mg) in NMP (1 ml) was heated at 120° C. under microwave conditions for 50 minutes. The product was then purified by HPLC to give expected product, 1-methyl-6-{4-[3-(2-methyl-imidazol-1-yl)-propoxy]-3-(trifluoromethyl)-phenyl}-1H-imidazo[4,5-c]pyridine-4-carbonitrile as a TFA salt. ¹H NMR (CD3OD) δ: 8.48 (s, 1H), 8.35-8.45 (m, 3H), 7.54 (d, 1H), 7.48 (d, 1H), 7.35 (d, 1H), 4.43 (t, 2H), 4.31 (t, 2H), 4.06 (s, 3H), 2.68 (s, 3H), 2.48 (m, 2H). MS m/z 441 (M+H).

The procedure described in Example 7a was further applied, using the appropriate starting materials, to prepare the following compounds as TFA salt:

7b: 6-{4-[3-(2-Ethyl-imidazol-1-yl)-propoxy]-3-(trifluoromethyl)-phenyl}-1-methyl-1H-imidazo[4,5-c]pyridine-4-carbonitrile TFA salt ¹H NMR (CD3OD) δ: 8.45 (s, 1H), 8.35-8.44 (m, 3H), 7.54 (d, 1H), 7.48 (d, 1H), 7.35 (d, 1H), 4.42 (t, 2H), 4.29 (t, 2H), 4.03 (s, 3H), 3.04 (q, 2H), 2.68 (s, 3H), 2.43 (m, 2H), 1.39 (t, 3H). MS m/z 455 (M+H).

7c: 1-Methyl-6-{4-[3-(4,5,6,7-tetrahydro-benzoimidazol-1-yl)-propoxy]-3-(trifluoromethyl)-phenyl}-1H-imidazo[4,5-c]Pyridine-4-carbonitrile TFA salt ¹H NMR (CD3OD) δ: 8.56 (s, 1H), 8.45 (s, 1H), 8.35-8.43 (m, 3H), 7.32 (d, 1H), 4.35 (t, 2H), 4.28 (t, 2H), 4.03 (s, 3H), 2.65 (m, 4H), 2.37 (m, 2H), 1.90 (m, 4H). MS m/z 481 (M+H).

EXAMPLE 8

6-[4-(2-Hydroxyethoxy)-3-(trifluoromethyl)-phenyl]-1-methyl-1H-imidazo[4,5-c]pyridine-4-carbonitrile

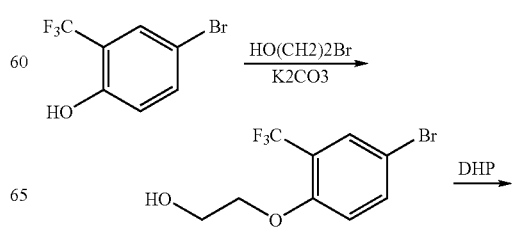

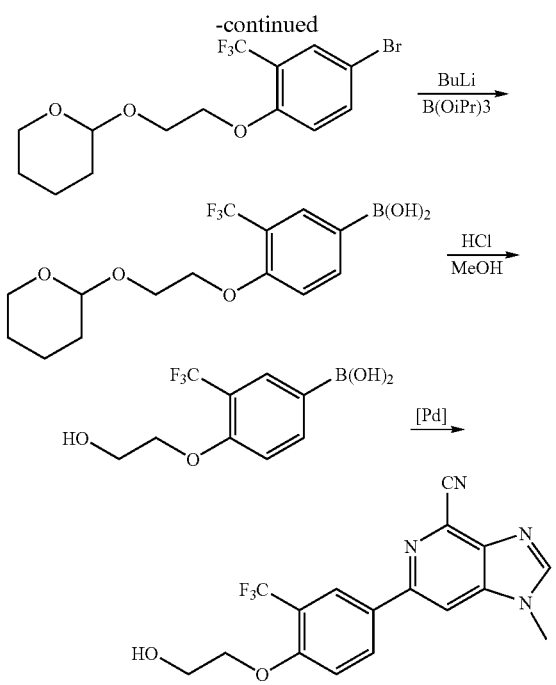

A: 2-(4-Bromo-2-(trifluoromethyl)phenoxy)-ethanol

2-Bromoethanol (23.3 g) was added to a mixture of 4-bromo-2-(trifluoromethyl)-phenol (30 g) and potassium carbonate (34.4 g) in acetonitrile (200 ml). The above mixture was refluxed for 8 hours then another portion of 2-bromoethanol (8 g) was added and the reflux continued for another 6 hours. After diluting with ethyl acetate (500 ml), the mixture was washed with water (300 ml) then 0.1 M sodium hydroxide (200 ml). Organic layer was dried over magnesium sulphate, solvent removed under reduced pressure, the residue was taken into heptane by heat, 2-(4-bromo-2-(trifluoromethyl)-phenoxy)-ethanol crystalised and collected by filtration (17 g).

$^1$H NMR (CDCl3) δ: 7.69 (d, 1H), 7.59 (dd, 1H), 6.90 (d, 1H), 4.15 (t, 2H), 3.97 (t, 2H).

B: 2-(2-(4-Bromo-2-(trifluoromethyl)-phenoxy)-ethoxy)-tetrahydro-2H-pyran

A mixture of 2-(4-bromo-2-(trifluoromethyl)phenoxy) ethanol (16 g), 3,4-dihydro-2H-puran (9.5 g) and p-toluenesulfonic acid hydrate (0.5 g) in THF (100 ml) was stirred at room temperature for 1 hour then diluted with 5% sodium bicarbonate (300 ml) and extracted with ethyl acetate (500 ml). Organic layer was then dried over sodium sulphate, solvent removed under vacuum to give expected product (21 g).

$^1$H NMR (CDCl3) δ: 7.67 (d, 1H), 7.58 (dd, 1H), 6.93 (d, 1H), 4.71 (m, 1H), 4.23 (t, 2H), 4.08 (m, 1H), 3.75-3.95 (m, 2H), 3.53 (m, 1H), 1.5-1.9 (m, 6H).

C: 4-(2-(tetrahydro-2H-pyran-2-yloxy)-ethoxy)-3-(trifluoromethyl)-phenylboronic Acid BuLi (2.5M, 6 ml) was added dropwise to a solution of 2-(2-(4-bromo-2-(trifluoromethyl)phenoxy)ethoxy)tetrahydro-2H-pyran (5 g) in THF (50 ml) at −78° C. under N2 during 3 minutes. After stirring at −78° C. for another 10 minutes, triisopropyl borate (3.8 ml) was then added dropwise during 2 minutes at −78° C. The mixture was stirred at −78° C. for further 30 minutes, then slowly warmed up to room temperature and stirred at room temperature for 30 minutes. The mixture was then quenched with acetic acid (10% in water, 20 ml), extracted with EtOAc (300 ml), washed with water (200 ml×3), dried over sodium sulphate, solvent removed under reduced pressure, the residue was taken in to toluene and then solvent removed under reduced pressure to take out trace of acetic acid (repeat 3 times, until no acetic acid smell) (4.5 g).

$^1$H NMR (CDCl3) δ: 8.38 (m, 1H), 8.33 (m, 1H), 7.16 (m, 1H), 4.74 (m, 1H), 4.22 (m, 2H), 4.08 (m, 1H), 3.92-3.80 (m, 2H), 3.56-3.50 (m, 1H), 1.90-1.68 (m, 2H), 1.65-1.48 (m, 4H).

D: 4-(2-Hydroxyethoxy)-3-(trifluoromethyl)-phenylboronic Acid 4-(2-(Tetrahydro-2H-pyran-2-yloxy)ethoxy)-3-(trifluoromethyl)phenylboronic acid (8 g) was added to hydrochloric acid (1M in MeOH) and the mixture was heated at 60° C. for 60 minutes. Solvent and HCl was then removed under reduced pressure and residue (5.52 g) was used for next step without further purification.

$^1$H NMR (CDCl3 (0.7 ml)+CD3OD (0.2 ml)) δ: 7.97 (s, 1H), 7.88 (d, 1H), 7.0 (d, 1H), 4.19 (t, 2H), 3.98 (t, 2H).

E: 6-[4-(2-Hydroxyethoxy)-3-(trifluoromethyl)-phenyl]-1-methyl-1H-imidazo[4,5-c]pyridine-4-carbonitrile A mixture of 6-chloro-1-methyl-1H-imidazo[4,5-c]pyridine-4-carbonitrile (0.75 g), 4-(2-hydroxyethoxy)-3-(trifluoromethyl)phenylboronic acid (1.46 g), tris(dibenzylideneacetone)dipalladium (0.18 g), tricyclohexylphosphine (0.13 g) and tribasic potassium phosphate (1.65 g) in dioxane (7.5 ml) and water (3 ml) was heated at 100° C. under N2 for 3 hours. The mixture was then diluted with ethyl acetate (100 ml), organic layer separated and solvent removed under reduced pressure, the residue was then columned on silica gel using DCM-MeOH (3%) as eluant to give 6-[4-(2-hydroxyethoxy)-3-(trifluoromethyl)phenyl]-1-methyl-1H-imidazo[4,5-c]pyridine-4-carbonitrile (1.07 g).

$^1$H NMR (DMSO) δ: 8.65 (s, 1H), 8.60 (s, 1H), 8.40 (d, 1H), 8.39 (s, 1H), 7.43 (d, 1H), 4.9 (t, 1H), 4.25 (t, 1H), 3.97 (s, 3H), 3.30 (m, 1H). MS m/z 363 (M+H).

EXAMPLE 9a

6-{4-[2-(6,9-Diaza-spiro-[4,5]dec-9-yl)-ethoxy]-3-(trifluoromethyl)-phenyl}-1-methyl-1H-imidazo[4,5-c]pyridine-4-carbonitrile TFA salt

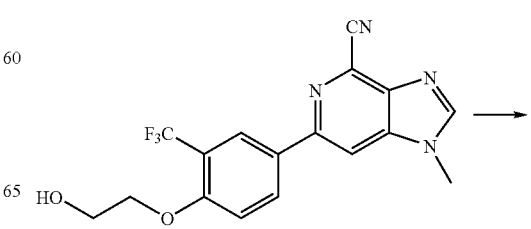

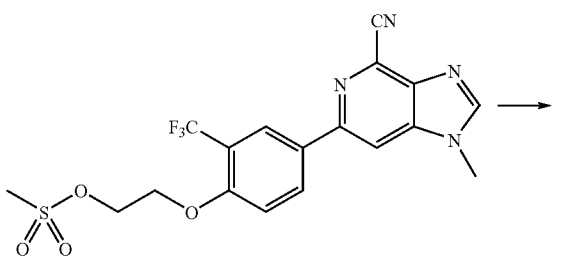

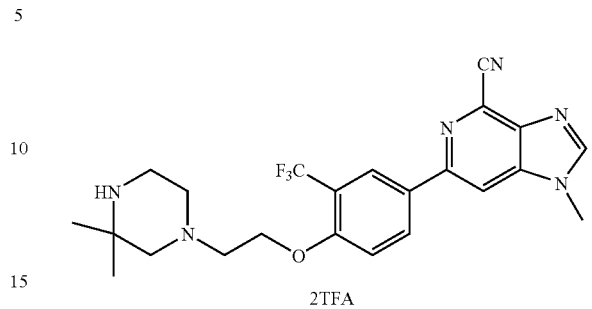

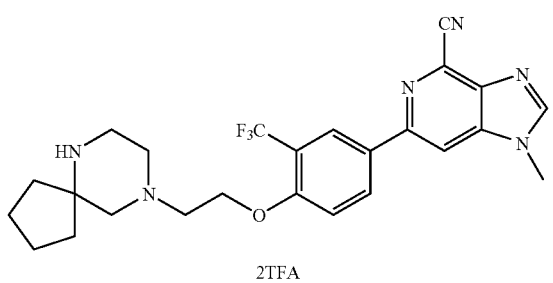

A: 2-(4-(4-Cyano-1-methyl-1H-imidazo[4,5-c]pyridin-6-yl)-2-(trifluoromethyl)phenoxy)ethyl Methanesulfonate Methanesulphonyl chloride (0.23 ml) was added dropwise to a solution of 6-(4-(2-hydroxyethoxy)-3-(trifluoromethyl)-phenyl)-1-methyl-1H-imidazo[4,5-c]pyridine-4-carbonitrile (0.77 g) and diisopropylethylamine (1.2 ml) in NMP (6 ml). The mixture was stirred at room temperature for 3 hours. After adding cold water (20 ml), solid product was collected by filtration, washed with cold ethanol (20 ml) to give 2-(4-(4-cyano-1-methyl-1H-imidazo[4,5-c]pyridin-6-yl)-2-(trifluoromethyl)phenoxy)ethyl methanesulfonate (0.89 g). $^1$H NMR (DMSO) δ: 8.72 (s, 1H), 8.64 (s, 1H), 8.47 (d, 1H), 8.43 (s, 1H), 7.48 (d, 1H), 4.58 (t, 2H), 4.51 (t, 2H), 3.99 (s, 3H), 3.23 (s, 3H). MS m/z 441 (M+1).

B: 6-{4-[2-(6,9-Diaza-spiro-[4.5]dec-9-yl)-ethoxy]-3-(trifluoromethyl)-phenyl}-1-methyl-1H-imidazo[4,5-c]pyridine-4-carbonitrile TFA salt A mixture of 2-(4-(4-cyano-1-methyl-1H-imidazo[4,5-c]pyridin-6-yl)-2-(trifluoromethyl)phenoxy)ethyl methanesulfonate (20 mg), and 6,9-diaza-spiro-[4.5]decane (33 mg) in NMP (1 ml) was stirred at room temperature for 72 hours. The product was then purified by HPLC to give expected product, 6-{4-[2-(6,9-diaza-spiro-[4.5]dec-9-yl)-ethoxy]-3-(trifluoromethyl)-phenyl}-1-methyl-1H-imidazo[4,5-c]pyridine-4-carbonitrile as a TFA salt. $^1$H NMR (CD3OD) δ: 8.45 (s, 1H), 8.3-8.43 (m, 3H), 7.34 (d, 1H), 4.36 (t, 2H), 4.02 (s, 3H), 3.26 (t, 2H), 3.02 (t, 2H), 2.90 (br, 2H), 2.77 (s, 2H), 2.05 (m, 2H), 1.6-1.9 (m, 6H). MS m/z 485 (M+H).

The procedure described in Example 9a was further applied, using the appropriate amine derivatives, to prepare the following compounds as either TFA salt, free base or HCl salt.

9b: 6-{4-[2-(3,3-Dimethyl-piperazin-1-yl)-ethoxy]-3-(trifluoromethyl)-phenyl}-1-methyl-1H-imidazo[4,5-c]pyridine-4-carbonitrile TFA salt $^1$H NMR (CD3OD) δ: 8.45 (s, 1H), 8.3-8.43 (m, 3H), 7.34 (d, 1H), 4.36 (t, 2H), 4.02 (s, 3H), 3.28 (t, 2H), 3.02 (t, 2H), 2.92 (br, 2H), 2.75 (s, 2H), 1.42 (s, 6H). MS m/z 459 (M+H).

9c: 1-Methyl-6-{4-[2-(piprerazin-1-yl)-ethoxy]-3-(trifluoromethyl)-phenyl}-1H-imidazo[4,5-c]pyridine-4-carbonitrile TFA salt $^1$H NMR (CD3CN) δ: 8.60 (s, 1H), 8.56 (d, 1H), 8.48 (s, 1H), 8.45 (s, 1H), 7.51 (d, 1H), 4.72 (t, 2H), 4.14 (s, 3H), 3.58-3.73 (m, 10H). MS m/z 431 (M+H).

9d: 6-{4-[2-(cis-3,5-dimethyl-piperazin-1-yl)-ethoxy]3-(trifluoromethyl)-phenyl}-1-methyl-1H-imidazo[4,5-c]pyridine-4-carbonitrile $^1$H NMR (CDCl3) δ: 8.28 (d, 1H), 8.22 (s, 1H), 8.08 (s, 1H), 7.87 (s, 1H), 7.12 (d, 1H), 4.28 (t, 2H), 3.99 (s, 3H), 3.49 (s, 1H), 2.85-3.05 (m, 6H), 1.88 (t, 2H), 1.09 (d, 6H). MS m/z 459 (M+H).

9e: 6-{4-[2-(4-Isopropyl-piperazin-1-yl)-ethoxy]-3-(trifluoromethyl)-phenyl}-1-methyl-1H-imidazo[4,5-c]pyridine-4-carbonitrile $^1$H NMR (CDCl3) δ: 8.27 (d, 1H), 8.22 (s, 1H), 8.08 (s, 1H), 7.87 (s, 1H), 7.11 (d, 1H), 4.28 (t, 2H), 3.99 (s, 3H), 2.92 (t, 2H), 2.5-2.8 (br, 9H, piperazine Hs+isopropyl CH), 1.08 (d, 6H), MS m/z 473 (M+H).

EXAMPLE 10a

1-Methyl-6-{4-[2-(2-methyl-imidazol-1-yl)-ethoxy-3-(trifluoromethyl)-phenyl]}1H-imidazo[4,5-c]pyridine-4-carbonitrile TFA salt

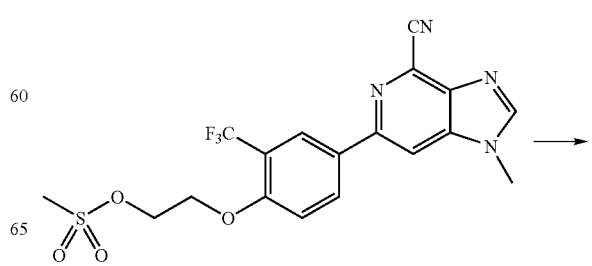

-continued

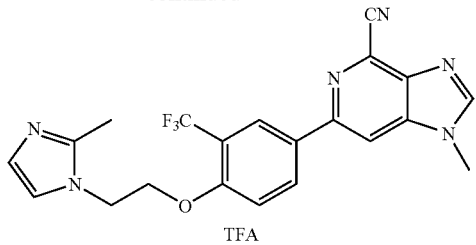

TFA

A mixture of 2-(4-(4-cyano-1-methyl-1H-imidazo[4,5-c]pyridin-6-yl)-2-(trifluoromethyl)phenoxy)ethyl methanesulfonate (20 mg), and 2-methylimidazole (20 mg) in NMP (1 ml) was heated using microwave at 120° C. for 40 minutes. The product was then purified by HPLC to give expected product, 1-methyl-6-{4-[2-(2-methyl-imidazol-1-yl)-ethoxy]-3-(trifluoromethyl)-phenyl}-1H-imidazo[4,5-c]pyridine-4-carbonitrile as a TFA salt.

$^1$H NMR (CD3OD) δ: 8.45 (s, 1H), 8.3-8.43 (m, 3H), 7.61 (d, 1H), 7.50 (d, 1H), 7.37 (d, 1H), 4.69 (t, 2H), 4.59 (t, 2H), 4.02 (s, 3H), 2.75 (s, 3H). MS m/z 427 (M+H).

The procedure described in Example 10a was further applied, using the appropriate amine/imidazole derivatives, to prepare the following compounds as either TFA salt, HCl salt or neutral compound:

10b: 1-Methyl-6-{4-[2-(4,5,6,7-tetrahydro-benzoimidazol-1-yl)-ethoxy]-3-(trifluoromethyl)-phenyl}-1H-imidazo[4,5-c]pyridine-4-carbonitrile TFA salt

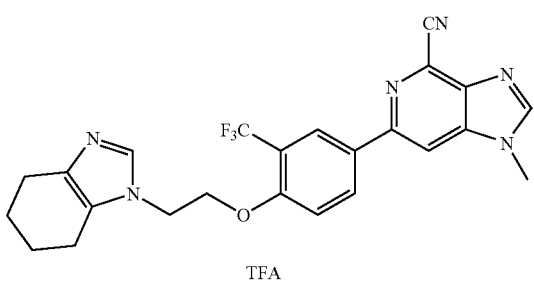

TFA $^1$H NMR (CD3OD) δ: 8.76 (s, 1H), 8.46 (s, 1H), 8.3-8.43 (m, 3H), 7.36 (d, 1H), 4.66 (t, 2H), 4.55 (t, 2H), 4.02 (s, 3H), 2.76 (m, 2H), 2.68 (m, 2H), 1.85-2.05 (m, 4H). MS m/z 467 (M+H).

10c: 1-Methyl-6-{4-[2-(4-(2-methoxyethyl)-piperazin-1-yl)-ethoxy]-3-(trifluoromethyl)-phenyl}-1H-imidazo[4,5-c]pyridine-4-carbonitrile $^1$H NMR (CDCl3) δ: 8.27 (d, 1H), 8.22 (s, 1H), 8.08 (s, 1H), 7.87 (s, 1H), 7.11 (d, 1H), 4.28 (t, 2H), 3.99 (s, 3H), 3.53 (t, 2H), 3.36 (s, 3H), 2.92 (t, 2H), 2.5-2.8 (br, 10H). MS m/z 489 (M+H).

10d: 6-(4-{2-[4-(2-hydroxyethyl)-piperazin-1-yl]-ethoxy}-3-(trifluoromethyl)-phenyl)-1-methyl-1H-imidazo[4,5-c]pyridine-4-carbonitrile $^1$H NMR (CDCl3) δ: 8.27 (d, 1H), 8.22 (s, 1H), 8.08 (s, 1H), 7.87 (s, 1H), 7.12 (d, 1H), 4.28 (t, 2H), 3.99 (s, 3H), 3.65 (t, 2H), 2.92 (t, 2H), 2.5-2.8 (br, 10H). MS m/z 475 (M+H).

10e: 1-Methyl-6-(4-{2-[4-(pyridin-4-yl)-piperazin-1-yl]-ethoxy}-3-(trifluoromethyl)-phenyl)-1H-imidazo[4,5-c]pyridine-4-carbonitrile $^1$H NMR (DMSO) δ: 8.72 (s, 1H), 8.64 (s, 1H), 8.44 (m, 1H), 8.42 (s, 1H), 8.15 (d, 2H), 7.49 (m, 1H), 6.83 (d, 2H), 4.37 (m, 2H), 3.99 (s, 3H), 3.30 (m, 4H), 2.84 (m, 2H), 2.66 (m, 4H). MS m/z 508 (M+1).

EXAMPLE 11

1-Methyl-6-{4-[2-(8-methyl-2,4-dioxo-1,3,8-triaza-spiro[4.5]dec-3-yl)-ethoxy]-3-(trifluoromethyl)-phenyl}-1H-imidazo[4,5-c]pyridine-4-carbonitrile

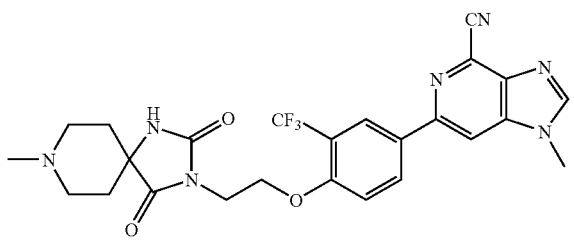

A solution of 8-methyl-1,3,8-triaza-spiro[4.5]decane-2,4-dione (40 mg) in DMF (0.6 mL) was added to a solution of 2-(4-(4-cyano-1-methyl-1H-imidazo[4,5-e]pyridin-6-yl)-2-(trifluoromethyl)phenoxy)ethyl methanesulfonate (50 mg) in DMF (0.4 mL), K$_2$CO$_3$ (41 mg) and tetrabutyl ammonium iodide (TBAI, 26 mg). The mixture was stirred at 90° C. for 14 hours. The crude mixture was directly purified by preparative HPLC (HPLC:column XBridge MS C18 30×100 mm, 5 μm, Eluent:A:NH$_4$HCO$_3$, 10 mmol, pH=9.5/B:Acetonitrile, Focused gradient/8 minutes/50 mL/min) to afford 1-methyl-6-{4-[2-(8-methyl-2,4-dioxo-1,3,8-triaza-spiro[4.5]dec-3-yl)-ethoxy]-3-(trifluoromethyl)-phenyl}-1H-imidazo[4,5-c]pyridine-4-carbonitrile (20 mg).

$^1$H NMR (DMSO) δ: 8.77 (br s, 1H), 8.72 (s, 1H), 8.64 (s, 1H), 8.43 (m, 1H), 8.39 (s, 1H), 8.16 (br s, 1H), 7.47 (m, 1H), 4.41 (m, 2H), 3.99 (s, 3H), 3.81 (m, 2H), 2.73 (m, 2H), 2.33 (m, 2H), 2.23 (s, 3H), 1.86 (m, 2H), 1.51 (m, 2H). MS m/z 528 (M+1).

EXAMPLE 12

6-(4-[2-(2,4-Dioxo-1,3,8-triaza-spiro[4.5]dec-3-yl)-ethoxy]-3-(trifluoromethyl)-phenyl)-1-methyl-1H-imidazo[4,5-c]pyridine-4-carbonitrile

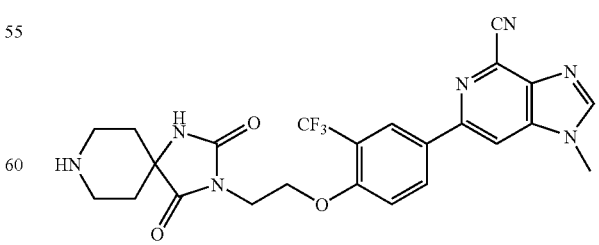

A solution of 8-tert-butoxycarbonyl-1,3,8-triaza-spiro [4.5]decane-2,4-dione (75 mg) in DMF (1 mL) was added to a solution of 2-(4-(4-cyano-1-methyl-1H-imidazo[4,5-c]pyridin-6-yl)-2-(trifluoromethyl)phenoxy)ethyl methanesulfonate (90 mg) in DMF (1 mL), K$_2$CO$_3$ (83 mg) and TBAI (48 mg). The mixture was stirred overnight at 90° C. The solvent was removed under reduced pressure. The residue was partitioned between ethyl acetate (50 ml) and a saturated solution of Na$_2$CO$_3$ (20 ml). The organic layer was dried over sodium sulphate, filtered and concentrated under reduced pressure to afford 3-(2-(4-(4-cyano-1-methyl-1H-imidazo[4,5-c]pyridin-6-yl)-2-trifluoromethyl-phenoxy)-ethyl)-2,4-dioxo-1,3,8-triaza-spiro[4.5]decane-8-carboxylic acid tert-butyl ester (70 mg). The crude product was dissolved in MeOH (2 mL) and a 5N solution of HCl in iPrOH (0.05 ml) was added. The mixture was stirred 2 hours at 60° C., then the solvent was evaporated under reduced pressure. The crude product was directly purified by preparative HPLC (HPLC: column XBridge MS C18 30×100 mm, 5 μm, Eluent:A: NH$_4$HCO$_3$, 10 mmol, pH=9.5/B:Acetonitrile, Focused gradient/8 minutes/50 mL/min) to afford 6-{4-[2-(2,4-dioxo-1,3,8-triaza-spiro[4.5]dec-3-yl)-ethoxy]-3-(trifluoromethyl)-phenyl}-1-methyl-1H-imidazo[4,5-c]pyridine-4-carbonitrile (23 mg).

$^1$H NMR (DMSO) δ: 8.82 (br s, 1H), 8.71 (s, 1H), 8.64 (s, 1H), 8.43 (m, 1H), 8.38 (s, 1H), 7.47 (m, 1H), 4.41 (m, 2H), 3.89 (s, 3H), 3.80 (m, 2H), 2.87 (m, 2H), 2.71 (m, 2H), 1.73 (m, 2H), 1.38 (m, 2H). MS m/z 514 (M+1).

EXAMPLE 13a

1-Methyl-6-{4-[2-(6-methyl-pyridin-2-yl)-ethoxy]-3-trifluoromethyl)-phenyl}-1H-imidazo[4,5-c]pyridine-4-carbonitrile Hydrochloride

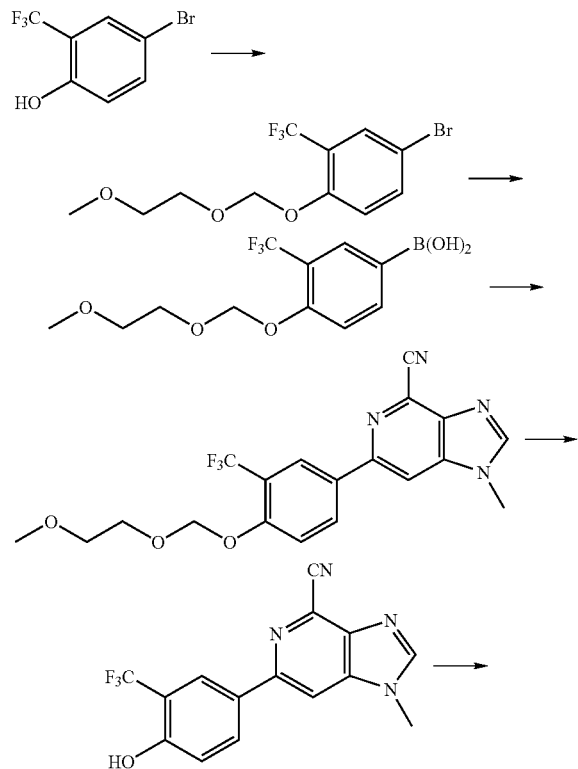

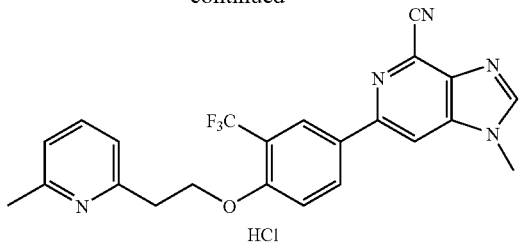

A: 4-Bromo-1-(2-methoxy-ethoxymethoxy)-2-trifluoromethyl-benzene

Sodium hydride (60% w/w dispersion in mineral oil, 0.96 g) was added to a solution of 4-bromo-2-trifluoromethyl-phenol (5.0 g) in dry THF (200 ml) and the mixture was stirred for 30 minutes. 1-Chloromethoxy-2-methoxy-ethane (2.85 ml) was then added and the mixture was stirred for 1 hour at room temperature. The solvent was removed under reduced pressure. The residue was taken into water and tert-butyl methyl ether, the organic layer was washed with brine, dried over sodium sulphate and concentrated under reduced pressure to afford 4-bromo-1-(2-methoxy-ethoxymethoxy)-2-trifluoromethyl-benzene (6.4 g) as an oil.

$^1$H NMR (CDCl3) δ: 7.69 (m, 1H), 7.53 (m, 1H), 7.19 (m, 1H), 5.33 (s, 2H), 3.83 (m, 2H), 3.55 (m, 2H), 3.37 (s, 3H).

B: 4-(2-Methoxy-ethoxymethoxy)-3-trifluoromethyl-phenyl-boronic Acid n-Butyl lithium (2.5M in hexane, 91.2 ml) was added dropwise to a solution of 4-bromo-1-(2-methoxy-ethoxymethoxy)-2-trifluoromethyl-benzene (30 g) in dry THF (335 ml) at −78° C. under nitrogen atmosphere. The mixture was then stirred at −78° C. for another 30 minutes. Triisopropyl borate (101 ml) was then added slowly at −78° C. under nitrogen, the mixture was then allowed to slowly warm up to room temperature and stirred at this temperature overnight. After adding water (300 ml), the mixture was extracted with ethyl acetate (300 ml×3). The combined organic layers were dried over sodium sulphate. After removal of solvent under reduced pressure, the residue was columned on silica gel using DCM-MeOH as eluant to give 4-(2-methoxy-ethoxymethoxy)-3-trifluoromethyl-phenyl-boronic acid (14.4 g).

$^1$H NMR (CDCl3) δ: 8.38 (m, 1H), 8.33 (m, 1H), 7.42 (m, 1H), 5.46 (s, 2H), 3.86 (m, 2H), 3.56 (m, 2H), 3.38 (s, 3H).

C: 6-(4-(2-Methoxy-ethoxymethoxy)-3-trifluoromethyl-phenyl)-1-methyl-1H-imidazo[4,5-c]pyridine-4-carbonitrile A mixture of 6-chloro-1-methyl-1H-imidazo[4,5-c]pyridine-4-carbonitrile is (5.9 g), 4-(2-methoxy-ethoxymethoxy)-3-trifluoromethyl-phenyl-boronic acid (9.92 g), potassium phosphate (11.1 g), tris(dibenzylideneacetone)dipalladium (1.4 g) and tricyclohexylphosphine (1.03 g) in dioxane (190 ml) and water (60 ml) was heated at 100° C. under nitrogen atmosphere for 2 hours. After cooling to room temperature, the mixture was then extracted with ethyl acetate (500 ml×2), the combined organic layers were dried over sodium sulphate and solvent was then removed under reduced pressure. To the residue was then added methanol (20 ml), and the solid product, 6-(4-(2-methoxyethoxymethoxy)-3-trifluoromethyl-phenyl)-1-methyl-1H-imidazo[4,5-c]pyridine-4-carbonitrile was collected by filtration (8.95 g).

$^1$H NMR (CDCl3) δ: 8.27 (m, 1H), 8.19 (m, 1H), 8.10 (s, 1H), 7.88 (s, 1H), 7.42 (m, 1H), 5.44 (s, 2H), 3.99 (s, 3H), 3.88 (m, 2H), 3.58 (m, 2H), 3.38 (s, 3H). MS m/z 407 (M+1).

D: 6-(4-Hydroxy-3-trifluoromethyl-phenyl)-1-methyl-1H-imidazo[4,5-c]pyridine-4-carbonitrile 6-(4-(2-Methoxy-ethoxymethoxy)-3-trifluoromethyl-phenyl)-1-methyl-1H-imidazo[4,5-c]pyridine-4-carbonitrile (7.5 g) was added to a mixed solvent of THF (300 ml) and 1M HCl (aq). The mixture was heated to 65° C. until the full disappearance of all starting material. After adding saturated sodium chloride solution (200 ml), the mixture was extracted with ethyl acetate (300 ml×3), and the combined organic layers were then dried over sodium sulphate, solvent was removed under reduces pressure, and the residue was triturated in ether. Product, 6-(4-hydroxy-3-trifluoromethyl-phenyl)-1-methyl-1H-imidazo[4,5-c]pyridine-4-carbonitrile (5.9 g) was collected by filtration.

$^1$H NMR (CD3OD) δ: 8.45 (s, 1H); 8.34 (s, 1H); 8.29 (s, 1H); 8.20 (m, 1H); 7.09 (m, 1H); 4.04 (s, 3H). MS m/z 319 (M+1).

E: 1-Methyl-6-{4-[2-(6-methyl-pyridin-2-yl)-ethoxy]-3-(trifluoromethyl)-phenyl}-1H-imidazo[4,5-c]pyridine-4-carbonitrile Hydrochloride Diisopropyl azodicarboxylate (80 mg) was added with stirring at room temperature under a nitrogen atmosphere to a mixture of 6-(4-hydroxy-3-trifluoromethyl-phenyl)-1-methyl-1H-imidazo[4,5-c]pyridine-4-carbonitrile (42 mg), resin bound triphenylphosphine (3 mmol/g, 130 mg) and 2-(6-methyl-pyridin-2-yl)ethanol (54 mg) in DCM (2 ml). The mixture was then shaken for 8 hours. After filtering off resin, the filtrate was concentrated under reduced pressure, and the residue was purified by HPLC to give 1-methyl-6-{4-[2-(6-methyl-pyridin-2-yl)-ethoxy]-3-(trifluoromethyl)-phenyl}-1H-imidazo[4,5-c]pyridine-4-carbonitrile as a TFA salt. This salt was then converted to free base and HCl salt using the procedure described in Example 2.

$^1$H NMR (CD3OD) δ: 8.52 (s, 1H), 8.35-8.5 (m, 4H), 7.92 (d, 1H), 7.82 (d, 1H), 7.39 (d, 1H), 4.63 (t, 2H), 4.03 (s, 3H), 3.61 (t, 2H), 2.83 (s, 3H). MS m/z 438 (M+1).

The procedure described in Example 13a was further applied, using the appropriate alcohol derivatives, to prepare the following compounds as either TFA salt, neutral compound or HCl salt:

13b: 1-Methyl-6-{4-[2-(5-methyl-pyridin-2-yl)-ethoxy]-3-(trifluoromethyl)-phenyl}-1H-imidazo[4,5-c]pyridine-4-carbonitrile Hydrochloride $^1$H NMR (CD3OD) δ: 8.68 (s, 1H), 8.59 (s, 1H), 8.35-8.5 (m, 4H), 8.03 (d, 1H), 7.38 (d, 1H), 4.64 (t, 2H), 4.04 (s, 3H), 3.60 (t, 2H), 2.57 (s, 3H). MS m/z 438 (M+1).

13c: 1-Methyl-6-[4-(pyridin-2-yl-methoxy)-3-(trifluoromethyl)-phenyl]-1H-imidazo[4,5-c]pyridine-4-carbonitrile Hydrochloride $^1$H NMR (DMSO) δ: 8.72 (s, 1H), 8.69 (d, 1H), 8.64 (s, 1H), 8.45-8.5 (m, 2H), 8.03 (t, 1H), 7.66 (d, 1H), 7.55 (d, 1H), 7.49 (t, 1H), 5.49 (s, 2H), 3.99 (s, 3H). MS m/z 410 (M+1).

13d: 1-Methyl-6-{4-[2-(pyridin-2-yl)-ethoxy]-3-(trifluoromethyl)-phenyl}-1H-imidazo[4,5-c]pyridine-4-carbonitrile Hydrochloride $^1$H NMR (DMSO) δ: 8.80 (d, 1H) δ: 8.70 (s, 1H), 8.63 (s, 1H), 8.45 (dd, 1H), 8.3-8.4 (m, 2H), 7.9 (d, 1H), 7.76 (t, 1H), 7.5 (d, 1H), 4.67 (t, 2H), 3.99 (s, 3H), 3.51 (t, 2H). MS m/z 424 (M+1).

13e: 1-Methyl-6-{4-[2-(4-methyl-thiazol-5-yl)-ethoxy]-3-(trifluoromethyl)-phenyl}-1H-imidazo[4,5-c]pyridine-4-carbonitrile $^1$H NMR (DMSO) δ: 8.86 (s, 1H), 8.72 (s, 1H), 8.64 (s, 1H), 8.44 (d, 1H), 8.40 (s, 1H), 7.44 (d, 1H), 4.38 (t, 2H), 3.99 (s, 3H), 3.29 (t, 2H), 2.37 (s, 3H). MS m/z 444 (M+1).

13f: 6-[4-(1,5-Dimethyl-1H-pyrazol-3-ylmethoxy)-3-(trifluoromethyl)-phenyl]-1-methyl-1H-imidazo[4,5-c]pyridine-4-carbonitrile $^1$H NMR (DMSO) δ: 8.72 (s, 1H), 8.64 (s, 1H), 8.43 (d, 1H), 8.40 (S, 1H), 7.59 (d, 1H), 6.11 (s, 1H), 5.19 (s, 2H), 3.99 (s, 3H), 3.72 (s, 3H), 2.24 (s, 3H). MS m/z 427 (M+1).

13g: 1-Methyl-6-{4-[(S)-5-oxo-2-pyrrolidin-2-yl-methoxy]-3-(trifluoromethyl)-phenyl}-1H-imidazo[4,5-c]pyridine-4-carbonitrile $^1$H NMR (DMSO) δ: 8.73 (s, 1H), 8.65 (s, 1H), 8.46 (d, 1H), 8.43 (s, 1H) 7.71 (s, 1H), 7.45 (d, 1H), 4.16 (s, 2H), 3.99 (s, 3H), 3.95 (br, 1H), 1.9-2.4 (m, 4H). MS m/z 416 (M+1).

13h: 1-Methyl-6-[4-(tetrahydro-furan-3-yl-methoxy)-3-(trifluoromethyl)-phenyl]-1H-imidazo[4,5-c]pyridine-4-carbonitrile $^1$H NMR (DMSO) δ: 8.72 (s, 1H), 8.65 (s, 1H), 8.44 (d, 1H), 8.41 (s, 1H), 7.45 (d, 1H), 4.21 (dd, 1H), 4.18 (dd 1H), 3.99 (s, 3H), 3.80 (m, 2H), 3.71 (dd, 1H), 3.67 (dd, 1H), 2.70 (m, 1H), 2.06 (m, 1H), 1.72 (m, 1H). MS m/z 403 (M+1).

13i: 6-[4-(3-Cyanopropoxy)-3-(trifluoromethyl)-phenyl]-1-methyl-1H-imidazo[4,5-c]pyridine-4-carbonitrile $^1$H NMR (DMSO) δ: 8.73 (s, 1H), 8.65 (s, 1H) 8.45 (d, 1H), 8.42 (s, 1H), 7.47 (d, 1H), 4.28 (t, 2H), 3.99 (s, 3H), 2.67 (t, 2H), 2.11 (m, 2H). MS m/z 386 (M+1).

13j: 1-Methyl-6-[4-(4-oxo-pentoxy)-3-(trifluoromethyl)-phenyl]-1H-imidazo[4,5-c]pyridine-4-carbonitrile $^1$H NMR (DMSO) δ: 8.72 (s, 1H), 8.64 (s, 1H), 8.45 (d, 1H), 8.41 (s, 1H), 7.42 (d, 1H), 4.18 (t, 2H), 3.99 (s, 3H), 2.64 (t, 2H), 2.12 (s, 3H), 1.95 (m, 2H). MS m/z 403 (M+A).

13k: 6-[4-(4-Cyanobenzoxy)-3-(trifluormethyl)-phenyl]-1-methyl-1H-imidazo[4,5-c]pyridine-4-carbonitrile $^1$H NMR (DMSO) δ: 8.73 (s, 1H), 8.65 (s, 1H), 8.46 (d, 1H), 8.45 (s, 1H), 7.95 (d, 2H), 7.67 (d, 2H), 7.52 (d, 1H), 5.50 (s, 2H), 3.99 (s, 3H). MS m/z 434 (M+1).

13l: 1-Methyl-6-{4-[3-(2-oxo-pyrrolidin-1-yl)-propoxy]-3-trifluoromethyl)-phenyl}-1H-imidazo[4,5-c]pyridine-4-carbonitrile $^1$H NMR (CD3OD) δ: 8.47 (s, 1H), 8.38 (s, 1H+1H), 8.35 (d, 1H), 7.30 (d, 1H), 4.23 (t, 2H), 4.05 (s, 3H), 3.5-3.6 (m, 4H), 2.41 (t, 2H), 2.05-2.2 (m, 4H). MS m/z 444 (M+1).

13m: 1-Methyl-6-{4-[2-(2-oxo-pyrrolidin-1-yl)-ethoxy]-3-(trifluoromethyl)-phenyl}-1H-imidazo[4, 5-c]pyridine-4-carbonitrile $^1$H NMR (CDCl3) δ: 8.23-8.31 (m, 2H), 8.08 (s, 1H), 7.87 (s, 1H), 7.11 (d, 1H), 4.29 (t, 2H), 3.98 (s, 3H), 3.75 (t, 2H), 3.64 (t, 2H), 2.40 (t, 2H), 2.06 (m, 2H). MS m/z 430 (M+1).

EXAMPLE 14a

1-Methyl-6-{4-[2-(piperidin-4-yl)-ethoxy]-3-(trifluoromethyl)-phenyl)-1H-imidazo[4,5-c]pyridine-4-carbonitrile Hydrochloride

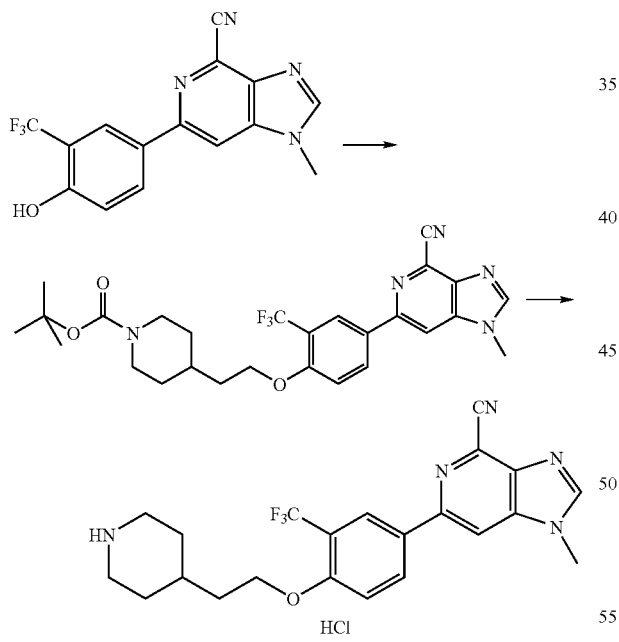

Diisopropyl azodicarboxylate (380 mg) was added with stirring at room temperature under nitrogen atmosphere to a mixture of 6-(4-hydroxy-3-trifluoromethyl-phenyl)-1-methyl-1H-imidazo[4,5-c]pyridine-4-carbonitrile (300 mg), resin bound triphenylphosphine (3 mmol/g 630 mg) and tert-butyl 4-(2-hydroxyethyl)piperidine-1-carboxylate (430 mg) in DCM (2 ml). The mixture was then shaken for 8 hours. After filtering off resin, the filtrate was concentrated under reduced pressure, residue was re-dissolved in DCM (5 ml) and to this solution was then added trifluoroactetic acid (3 ml). After stirring at room temperature for 10 minutes, all solvent and excess trifluoroacetic acid were removed under reduced pressure. The residue was dissolved in NMP (5 ml) and purified by HPLC to give 1-methyl-6-{4-[2-(piperidin-4-yl)-ethoxy]-3-(trifluoromethyl)-phenyl}-1H-imidazo[4,5-c]pyridine-4-carbonitrile as a TFA salt. This salt was then converted to free base and HCl salt (230 mg) using the procedure described in Example 2.

$^1$H NMR (CD3OD) δ: 8.73 (s, 1H), 8.47 (s, 1H), 8.40 (s, 1H), 8.39 (d, 1H), 7.35 (d, 1H), 4.29 (t, 2H), 4.07 (s, 3H), 3.42 (dm, 2H), 3.00 (t, 2H), 2.06 (d, 2H), 1.98 (m, 2H), 1.90 (t, 2H), 1.50 (m, 2H). MS m/z 430 (M+1).

The procedure described in Example 14a was further applied, using the appropriate alcohol derivatives, to prepare the following compound:

14b: 1-Methyl-6-{4-[(piperidin-4-yl)-methoxy)]-1-3-(trifluoromethyl)-phenyl}-1H-imidazo[4,5-c]pyridine-4-carbonitrile $^1$H NMR (DMSO) δ: 8.71 (s, 1H), 8.64 (s, 1H), 8.44 (d, 1H), 8.41 (s, 1H), 7.42 (d, 1H), 4.02 (d, 2H), 3.98 (s, 3H), 3.00 (d, 2H), 2.55 (m, 2H), 1.90 (m, 1H), 1.75 (d, 2H), 1.25 (m, 2H). MS m/z 416 (M+1).

EXAMPLE 15

6-[4-(3-Hydroxypropyl)-3-(trifluoromethyl)-phenyl]-1-methyl-1H-imidazo[4,5-c]pyridine-4-carbonitrile

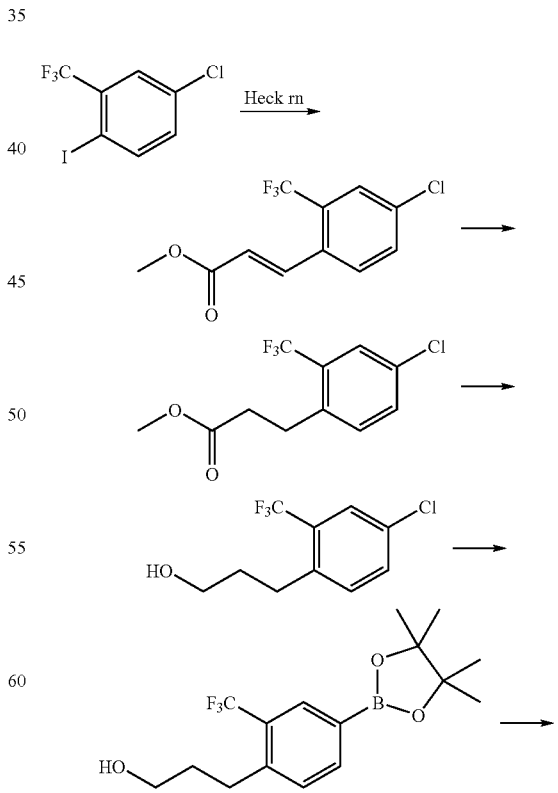

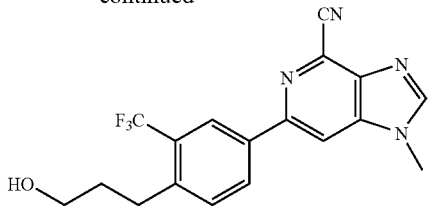

A: (E)-methyl 3-(4-chloro-2-(trifluoromethyl)-phenyl)-acrylate

The mixture of 4-chloro-1-iodo-2-(trifluoromethyl)-benzene (15 g), methyl acrylate (6.74 g), tetrabutylammonium chloride (14 g), palladium acetate (0.22 g) and potassium carbonate (13.6 g) in DMF (150 ml) was stirred at room temperature for 4 days. After diluting with ether (1 L), the mixture was washed with water (5×200 ml), then dried over sodium sulphate and solvent removed under reduced pressure. The residue was columned on silica gel using 5:1 heptane:EtOAc as eluant to give (E)-methyl 3-(4-chloro-2-(trifluoromethyl)-phenyl)-acrylate (13 g).
$^1$H NMR (CDCl3) δ: 7.99 (d, 1H), 7.70 (s, 1H), 7.65 (d, 1H), 7.56 (d, 1H), 6.4 (d, 1H), 3.83 (s, 3H)

B: Methyl 3-(4-chloro-2-(trifluoromethyl)-phenyl)-propanoate

A mixture of (E)-methyl 3-(4-chloro-2-(trifluoromethyl) phenyl)acrylate (5 g) and palladium on charcoal (10%, dry, 2 g) in ethyl acetate (50 ml) was stirred under balloon hydrogen pressure for 3 hours. After filtration, filtrate was concentrated to give methyl 3-(4-chloro-2-(trifluoromethyl)-phenyl)propanoate (5 g).
$^1$H NMR (CDCl3) δ: 7.62 (s, 1H), 7.45 (d, 1H), 7.30 (d, 1H), 3.69 (s, 3H), 3.10 (t, 2H), 2.61 (t, 2H).

C: 3-(4-Chloro-2-(trifluoromethyl)-phenyl)propan-1-ol

Diisobutylaluminum hydride (20% in toluene, 34 ml) was added dropwise to a solution of methyl 3-(4-chloro-2-(trifluoromethyl)phenyl)propanoate (5 g) in DCM (150 ml) at −78° C. under nitrogen during 10 minutes. The mixture was then stirred at −78° C. for 1 hour before warming up to room temperature. The mixture was then carefully poured to crushed ice (500 g). After adding 5M HCl to pH 2, the mixture was extracted with DCM (200 ml×3), combined DCM layer was then dried over sodium sulphate, solvent was then removed under reduced pressure. The residue was clean enough for next step (4.5 g).
$^1$H NMR (CDCl3) δ: 7.60 (s, 1H), 7.44 (d, 1H), 7.30 (d, 1H), 3.71 (t, 2H), 2.85 (t, 2H), 1.87 (m, 2H).

D: 3-(4-(4,4,5,5-tetramethyl-1,3,2-dioxaborolan-2-yl)-2-(trifluoromethyl)phenyl)propan-1-ol The mixture of 3-(4-chloro-2-(trifluoromethyl)phenyl) propan-1-ol (1 g), tris(dibenzylideneacetone)dipalladium (0.192 g), tricyclohexylphosphine (0.141 g), potassium acetate (0.62 g) and, bis(pinacolato)diboron (1.17 g) in dried dioxane (15 ml) was heated at 80° C. for 6 hours. After diluting with ethyl acetate (100 ml), washing with water (100 ml), brine (100 ml), then drying over sodium sulphate, solvent was removed under reduced pressure, and the residue was columned on silica gel using heptane:EtOAc (4:1) as eluant to give 3-(4-(4,4,5,5-tetramethyl-1,3,2-dioxaborolan-2-yl)-2-(trifluoromethyl)phenyl)propan-1-ol (1 g).
$^1$H NMR (CDCl3) δ: 8.06 (s, 1H), 7.9 (d, 1H), 7.37 (d, 1H), 3-72 (t, 2H), 2.9 (t, 2H), 1.9 (m, 2H), 1.35 (s, 12H).

E: 6-[4-(3-Hydroxy-propyl)-3-(trifluoromethyl)-phenyl]-1-methyl-1H-imidazo[4,5-c]pyridine-4-carbonitrile 6-Chloro-1-methyl-1H-imidazo[4,5-c]pyridine-4-carbonitrile (1.29 g), 3-(4-(4,4,5,5-tetramethyl-1,3,2-dioxaborolan-2-yl)-2-(trifluoromethyl)phenyl)propan-1-ol (2.432 g), tris(dibenzylideneacetone)dipalladium (0.307 g), tricyclohexylphosphine (0.225 g) and potassium phosphate (2.417 g) were suspended in dioxane (20 ml) and water (8 ml). The reaction mixture was placed under a nitrogen atmosphere and heated to reflux (110° C.) for 1.5 hours. The mixture was allowed to cool to room temperature then diluted with EtOAc (500 mL), filtered through celite and washed with water (200 mL). Organic layer was dried over sodium sulphate and solvent was evaporated under reduced pressure. The solid residue was washed with ether to afford 6-[4-(3-hydroxypropyl)-3-(trifluoromethyl)-phenyl]-1-methyl-1H-imidazo[4,5-c] pyridine-4-carbonitrile (1.5 g).
$^1$H NMR (CD3OD) δ: 8.46 (s, 1H), 8.45 (s, 1H), 8.44 (s, 1H), 8.31 (d, 1H), 7.60 (d, 1H), 4.04 (s, 3H), 3.66 (t, 2H), 2.94 (t, 2H), 1.90 (m, 2H).

EXAMPLE 16a

1-Methyl-6-{4-[3-(3-oxo-piperazin-1-yl)-propyl]-3-(trifluoromethyl)-phenyl}-1H-imidazo[4,5-c]pyridine-4-carbonitrile

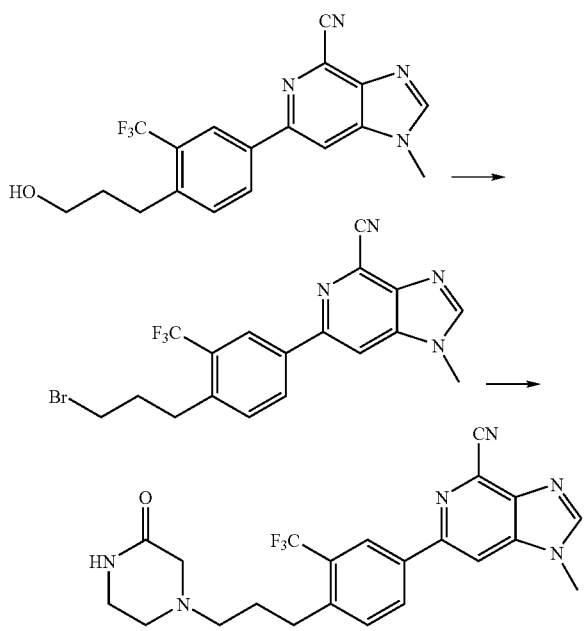

A: 6-(4-(3-Bromopropyl)-3-(trifluoromethyl)-phenyl-1-methyl-1H-imidazo[4,5-c]pyridine-4-carbonitrile 6-[4-(3-Hydroxypropyl)-3-(trifluoromethyl)-phenyl]-1-methyl-1H-imidazo[4,5-c]pyridine-4-carbonitrile (1.3 g)

was gently heated in THF (36 ml) until all dissolved and then cooled to 0° C. in an ice bath. Carbon tetrabromide (2.4 g) was added followed by triphenylphosphine (1.9 g). The mixture was stirred at 0° C. for 15 minutes and then at room temperature for 20 minutes until the cloudy suspension became a clear solution. The reaction mixture was diluted with DCM (100 ml) and washed with water (100 ml×2). Organic layer was dried over sodium sulphate and solvent was evaporated under reduced pressure. The residue was then columned (100 g SiO$_2$ column, 1:1 EtOAc/Heptane to EtOAc gradient) to afford 6-(4-(3-bromopropyl)-3-(trifluoromethyl)-phenyl)-1-methyl-1H-imidazo[4,5-c]pyridine-4-carbonitrile (1.2 g) as a white solid.

$^1$H NMR (DMSO) δ: 8.77 (s, 1H), 8.66 (s, 1H), 8.46 (s, 1H), 8.40 (d, 1H), 7.69 (d, 1H), 4.00 (s, 3H), 3.65 (t, 2H), 2.95 (t, 2H), 2.17 (m, 2H).

B: 1-Methyl-6-{4-[3-(3-oxo-piperazin-1-yl)-propyl]-3-trifluoromethyl-phenyl}-1H-imidazo[4,5-c]pyridine-4-carbonitrile 6-(4-(3-Bromopropyl)-3-(trifluoromethyl)-phenyl)-1-methyl-1H-imidazo[4,5-c]pyridine-4-carbonitrile (50 mg) and 2-oxopiperazine (103 mg) in DMF (750 µl) were heated at 100° C. in a microwave for 25 minutes. Purification by basic phase preparative LCMS afforded 1-methyl-6-{4-[3-(3-oxo-piperazin-1-yl)-propyl]-3-trifluoromethyl-phenyl}-1H-imidazo[4,5-c]pyridine-4-carbonitrile (15 mg).

$^1$H NMR (CD3OD) δ: 8.45 (s, 1H) 8.43 (s, 1H) 8.42 (s, 1H) 8.29 (d, 1H) 7.60 (d, 1H) 4.03 (s, 3H) 3.34 (t, 2H) 3.12 (s, 2H) 2.91 (t, 2H) 2.70 (t, 2H) 2.56 (t, 2H) 1.90 (m, 2H). MS m/z 443 (M+1).

The procedure described in Example 16a was further applied, using the appropriate amine derivatives, to prepare the following compounds as either TFA salt, free base or HCl salt using the method described in Example 2:

16b: 6-[4-(3-(Dimethylamino)-propyl)-3-(trifluoromethyl)-phenyl]-1-methyl-1H-imidazo[4,5-c]pyridine-4-carbonitrile $^1$H NMR (CD3OD) δ: 8.45 (s, 2H), 8.43 (s, 1H), 8.29 (d, 1H), 7.60 (d, 1H), 4.03 (s, 3H), 2.88 (t, 2H), 2.57 (t, 2H), 2.35 (s, 6H), 1.90 (m, 2H). MS m/z 388 (M+1).

16c: 1-Methyl-6-[4-(3-morpholin-4-yl-propyl)-3-(trifluoromethyl)-phenyl]-1H-imidazo[4,5-c]pyridine-4-carbonitrile $^1$H NMR (CD3OD) δ: 8.45 (s, 1H) 8.44 (s, 1H) 8.42 (s, 1H) 8.30 (d, 1H) 7.60 (d, 1H) 4.03 (s, 3H) 3.72 (t, 4H) 2.90 (t, 2H) 2.54 (m, 6H) 1.92 (m, 2H). MS m/z 430.6 (M+1).

16d: 1-Methyl-6-{4-[3-(4-methyl-piperazin-1-yl)-propyl]-3-(trifluoromethyl)-phenyl}-1H-imidazo[4,5-d]pyridine-4-carbonitrile $^1$H NMR (DMSO) δ: 8.76 (s, 1H), 8.65 (s, 1H), 8.43 (s, 1H), 8.39 (d, 1H), 7.68 (d, 1H), 4.00 (s, 3H), 2.83 (t, 2H), 2.36 (m, 10H), 2.16 (s, 3H), 1.77 (m, 2H). MS m/z 443 (M+1).

16e: 6-(4-{3-[4-(2-Methoxy-ethyl)-piperazin-1-yl]-propyl}-3-(trifluoromethyl)-phenyl)-1-methyl-1H-imidazo[4,5-c]pyridine-4-carbonitrile TFA salt $^1$H NMR (DMSO) δ: 8.78 (s, 1H), 8.67 (s, 1H), 8.48 (s, 1H), 8.45 (d, 1H), 7.71 (d, 1H), 4.01 (s, 3H), 3.63 (t, 2H), 3.30 (s, 3H), 3.28 (broad m, 8H), 3.21 (broad m, 2H), 3.09 (broad m, 2H), 2.86 (t, 2H), 1.99 (m, 2H). MS m/z 487.5 (M+1).

16f: 6-(4-{3-[N-(2-Dimethylamino-2-oxo-ethyl)-N-methylamino]-propyl}-3-(trifluoromethyl)-phenyl)-1-methyl-1H-imidazo[4,5-d]pyridine-4-carbonitrile $^1$H NMR (DMSO) δ: 8.75 (s, 1H), 8.65 (s, 1H), 8.43 (s, 1H), 8.39 (d, 1H), 7.67 (d, 1H), 4.00 (s, 3H), 3.23 (s, 2H), 3.03 (s, 3H), 2.82 (m, 5H), 2.51 (broad m, 2H), 2.25 (s, 3H), 1.78 (m, 2H). MS m/z 459 (M+1).

The following compound was purified using acidic HPLC as TFA salt:

16 g: 1-Methyl-6-[4-(3-piperazin-1-yl-propyl)-3-(trifluoromethyl)-phenyl]-1H-imidazo[4,5-c]pyridine-4-carbonitrile TFA salt $^1$H NMR (DMSO) δ: 8.79 (s, 1H), 8.67 (s, 1H), 8.48 (s, 1H), 8.44 (d, 1H), 7.71 (d, 1H), 4.01 (s, 3H), 3.35 (broad m, 8H), 3.19 (broad m, 2H), 2.87 (t, 2H), 2.01 (broad m, 2H). MS m/z 429.4 (M+1).

EXAMPLE 17

1-Methyl-6-{4-[2-(2-oxooxazolidin-3-yl)-ethoxy]-3-(trifluoromethyl)-phenyl}-1H-imidazo[4,5-c]pyridine-4-carbonitrile

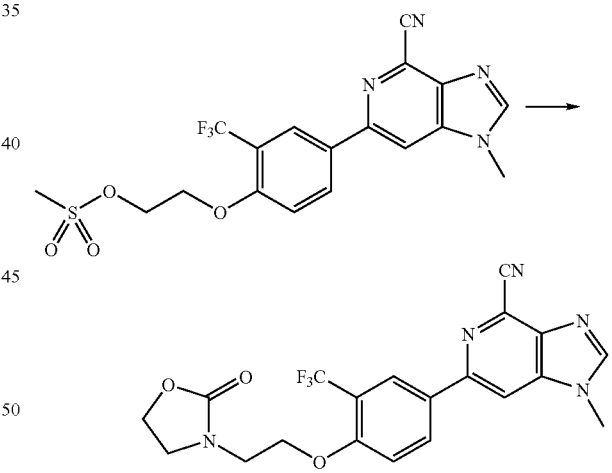

To oxazolidin-2-one (29.7 mg) in NMP (1 ml) was added sodium hydride is (60% in parafin oil, 13.6 mg). After stirring at room temperature for 10 minutes, 2-(4-(4-cyano-1-methyl-1H-imidazo[4,5-c]pyridin-6-yl)-2-(trifluoromethyl)phenoxy)ethyl methanesulfonate (100 mg) was then added and the mixture was stirred at room temperature for 14 hours. The mixture was purified directly using HPLC to give 1-methyl-6-{4-[2-(2-oxooxazolidin-3-yl)-ethoxy]-3-(trifluoromethyl)-phenyl}-1H-imidazo[4,5-c]pyridine-4-carbonitrile (10 mg).

$^1$H NMR (DMSO) δ: 8.70 (s, 1H), 8.63 (s, 1H), 8.45 (d 1H), 8.41 (s, 1H), 7.47 (d, 1H), 4.37 (t, 2H), 4.27 (t, 2H), 3.99 (s, 3H), 3.67 (t, 2H), 3.61 (t, 2H). MS m/z 432 (M+1).

EXAMPLE 18a

1-Methyl-6-{4-[3-(2-oxopiperazin-1-yl)-propoxy]-3-(trifluoromethyl)-phenyl}-1H-imidazo[4,5-c]pyridine-4-carbonitrile Hydrochloride

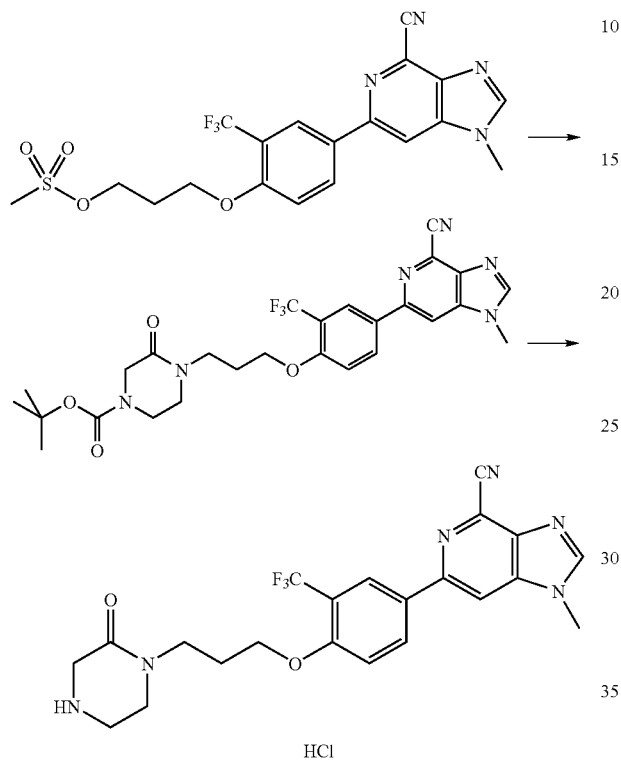

HCl

To tert-butyl 3-oxopiperazine-1-carboxylate (106 mg) in NMP (2 ml) was added sodium hydride (60% in parafin oil, 22 mg). After stirring at room temperature for 10 minutes, 3-(4-(4-cyano-1-methyl-1H-imidazo[4,5-c]pyridin-6-yl)-2-(trifluoromethyl)phenoxy)propyl methanesulfonate (200 mg) was then added and the mixture was stirred at room temperature for 14 hours. After diluting with ethyl acetate (50 ml), the mixture was washed with water (20 ml). Organic layer was then separated, solvent removed under vacuum, to the residue was then added 1:1 mixture of DCM:TFA (4 ml). After stirring at room temperature for 5 minutes, all solvent was removed under reduced pressure, residue was taken into MeOH (2 ml) and purified to HPLC to give 1-methyl-6-{4-[3-(2-oxopiperazin-1-yl)-propoxy]-3-(trifluoromethyl)-phenyl}-1H-imidazo[4,5-c]pyridine-4-carbonitrile as TFA salt. This TFA salt was converted to HCl salt using the method described above (Example 2).

$^1$H NMR (MeOD) δ: 8.53 (s, 1H), 8.42 (s, 1H), 8.40 (s, 1H), 8.37 (d, 1H), 7.35 (d, 1H), 4.26 (t, 2H), 4.04 (s, 3H), 3.83 (s, 2H), 3.65-3.8 (m, 4H), 3.56 (t, 2H), 2.18 (m, 2H). MS m/z 459 (M+1).

The procedure described in Example 18a was further applied, using 2-(4-(4-cyano-1-methyl-1H-imidazo[4,5-c]pyridin-6-yl)-2-(trifluoromethyl)phenoxy)ethyl methanesulfonate, to prepare the following compound as either TFA salt:

18b: 1-Methyl-6-{4-[2-(2-oxopiperazin-1-yl)-ethoxy]-3-(trifluoromethyl)-phenyl}-1H-imidazo[4,5-c]pyridine-4-carbonitrile TFA salt $^1$H NMR (DMSO) δ: 8.71 (s, 1H), 8.64 (s, 1H), 8.46 (d, 1H), 8.44 (s, 1H), 7.45 (d, 1H), 4.36 (t, 2H), 3.99 (s, 3H), 3.80 (t, 2H), 3.77 (s, 1H), 3.70 (d, 2H), 3.41 (t, 2H). MS m/z 445 (M+1).

EXAMPLE 19

6-{4-[3-(3,3-Dimethyl-2-oxopiperazin-1-yl)-propoxy]-3-(trifluoromethyl)-phenyl}-1-methyl-1H-imidazo[4,5-c]pyridine-4-carbonitrile TFA salt

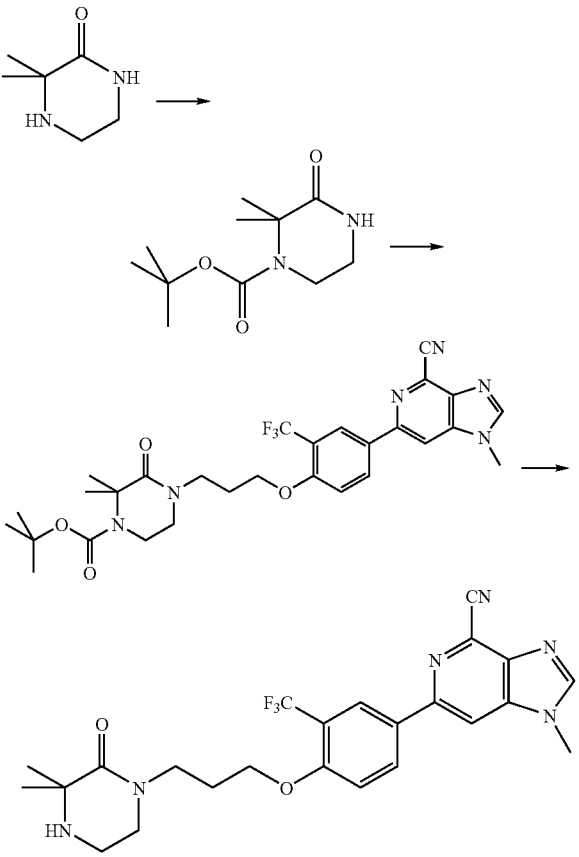

A: tert-Butyl 2,2-dimethyl-3-oxopiperazine-1-carboxylate

Di-tert-butyl dicarbonate (4 g) was added to a solution of 3,3-dimethylpiperazin-2-one hydrochloride (3 g) and DIPEA (3 ml) in DCM-MeOH (100 ml-30 ml). The mixture was stirred at room temperature for 2 days, then washed with water (100 ml×2), organic layer was dried over sodium sulphate, solvent was removed, and the residue was then columned on silica gel using 9:1 DCM:MeOH as eluant to give tert-butyl 2,2-dimethyl-3-oxopiperazine-1-carboxylate (3.6 g)

$^1$H NMR (CDCl3) δ: 3.2-3.35 (br, 2H), 3.35-3.4 (br, 2H), 1.50 (s), 1.47 (s), 1.44 (s).

B: 6-{4-[3-(3,3-Dimethyl-2-oxopiperazin-1-yl)-propoxy]-3-(trifluoromethyl-phenyl}-1-methyl-1H-imidazo[4,5,5-c]pyridine-4-carbonitrile TFA salt The procedure described in Example 18a was then applied, using tert-butyl 2,2-dimethyl-3-oxopiperazine-1-carboxylate to prepare 6-{4-[3-(3,3-dimethyl-2-oxopiperazin-1-yl)-propoxy]-3-(trifluoromethyl)-phenyl}-1-methyl-1H-imidazo[4,5-c]pyridine-4-carbonitrile as TFA salt.

¹H NMR (CD3OD) δ: 8.45 (s, 1H), 8.35-8.43 (m, 3H), 7.32 (d, 1H), 4.26 (t, 2H), 4.02 (s, 3H), 3.6-3.75 (m, 6H), 2.17 (m, 2H), 1.62 (s, 6H). MS m/z 487 (M+1).

EXAMPLE 20a

6-[4-(3-Morpholin-4-yl-propoxy)-3-(trifluoromethyl)-phenyl]-1H-imidazo[4,5-d]pyridine-4-carbonitrile

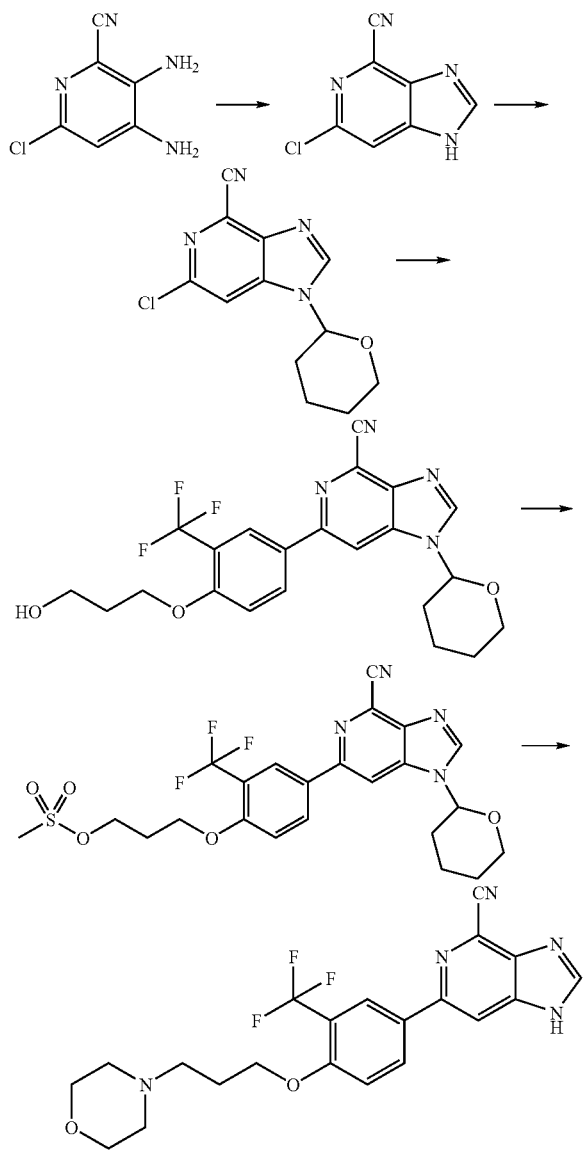

A: 6-chloro-1H-imidazo[4,5-c]pyridine-4-carbonitrile

A mixture of 3,4-diamino-6-chloropicolinonitrile (3.2 g), triethylorthoformate (16 ml) and AcOH (5.4 ml) was heated to 150° C. in DCM (16 ml) in a microwave for 15 minutes. Solvent was evaporated, residue was dissolved in EtOAc (250 mL) and washed with water (150 mL). Organic layer was dried over sodium sulphate. Solvent was evaporated under reduced pressure to yield 6-chloro-1H-imidazo[4,5-c]pyridine-4-carbonitrile (2.2 g).

¹H NMR (DMSO) δ: 8.72 (s, 1H), 8.06 (s, 1H).

B: 6-Chloro-1-(tetrahydro-2H-pyran-2-yl)-1H-imidazo[4,5-c]pyridine-4-carbonitrile 6-Chloro-1H-imidazo[4,5-c]pyridine-4-carbonitrile (620 mg) and p-toluenesulfonic acid monohydrate (10 mg) were suspended in ethyl acetate (10 ml) and heated to 60° C. 3,4-Dihydro-2H-pyran (0.48 ml) was added dropwise and the reaction stirred at 60° C. overnight. The reaction was quenched with 5 mL ammonium hydroxide before addition of water (100 mL) and ethyl acetate (200 mL). Organic layer was separated, dried over sodium sulphate and solvent was evaporated under reduced pressure. The crude product was dissolved in a minimum volume of EtOAc and heptane added. The resulting brown solid was collected by filtration to yield 6-chloro-1-(tetrahydro-2H-pyran-2-yl)-1H-imidazo[4,5-c]pyridine-4-carbonitrile (630 mg). ¹H NMR (DMSO) δ: 8.92 (s, 1H), 8.30 (s, 1H), 5.80 (d, 1H), 4.05 (m, 1H), 3.75 (m, 1H), 2.19 (m, 1H), 2.11 (m, 1H), 1.62 (m, 4H).

C: 6-[4-(3-hydroxypropoxy)-3-(trifluormethyl)-phenyl]-1-(tetrahydro-2H-pyran-2-yl)-1H-imidazo[4,5-c]pyridine-4-carbonitrile 6-Chloro-1-(tetrahydro-2H-pyran-2-yl)-1H-imidazo[4,5-c]pyridine-4-carbonitrile (1.4 g), 4-(3-hydroxypropoxy)-3-(trifluoromethyl)phenylboronic acid (2.2 g), tris(dibenzylideneacetone)dipalladium (0.25 g), tricyclohexylphosphine (0.18 g) and potassium phosphate (2 g) were added to dioxane (20 ml) and water (6 ml) and the mixture was heated to reflux under nitrogen for two hours. The reaction mixture was diluted with EtOAc (200 mL), filtered through celite, and washed with water (150 mL). Organic layer was dried over sodium sulphate and solvent was evaporated under reduced pressure. The crude product was purified by flash chromatography using EtOAc:Heptane as eluant to yield 6-[4-(3-hydroxypropoxy)-3-(trifluoromethyl)-phenyl]-1-(tetrahydro-2H-pyran-2-yl)-1H-imidazo[4,5-c]pyridine-4-carbonitrile (1.5 g).

MS m/z 447 (M+1).

D: 3-(4-(4-Cyano-1-(tetrahydro-2H-pyran-2-yl)-1H-imidazo[4,5-c]pyridin-6-yl)-2-(trifluoromethyl)phenoxy)propyl Methanesulfonate To a solution of 6-(4-(3-hydroxypropoxy)-3-(trifluoromethyl)phenyl)-1-(tetrahydro-2H-pyran-2-yl)-1H-imidazo[4,5-c]pyridine-4-carbonitrile (670 mg) and DIPEA (1.4 ml) in NMP (7.5 ml) at 0° C. was added methanesulphonyl chloride (0.2 ml). The mixture was allowed to stir for 45 minutes at room temperature, then diluted with EtOAc (75 ml) and washed with saturated sodium bicarbonate (70 ml), followed by water (2×40 ml). Organic layer was dried over sodium sulphate and solvent was evaporated under reduced pressure to yield 3-(4-(4-cyano-1-(tetrahydro-2H-pyran-2-yl)-1H- imidazo[4,5-c]pyridin-6-yl)-2-(trifluoromethyl)phenoxy) propyl methanesulfonate (720 mg).

MS m/z 525 (M+1).

E: 6-{4-[3-(3,3-Dimethyl-2-oxopiperazin-1-yl)-propoxy]-3-(trifluoromethyl)-phenyl}-1-methyl-1H-imidazo[4,5-c]pyridine-4-carbonitrile TFA salt A mixture of 3-(4-(4-cyano-1-(tetrahydro-2H-pyran-2-yl)-1H-imidazo[4,5-c]pyridin-6-yl)-2-(trifluoromethyl)phenoxy)propyl methanesulfonate (23 mg) and morpholine (20 ul) in NMP (500 µl) was heated at 120° C. in a microwave for 20 minutes. Aqueous HCl (2M, 50 µl) were then added and the mixture was stirred for 2 hours at 50° C. The mixture was then purified using preparative HPLC to generate product, 6-[4-(3-morpholin-4-yl-propoxy)-3-(trifluoromethyl)-phenyl]-1H-imidazo[4,5-c]pyridine-4-carbonitrile as a TFA salt, which was then converted to free base by using the method described in Example 2.

$^1$H NMR (DMSO) δ: 8.66 (s, 1H), 8.47 (s, 1H), 8.38 (d, 1H), 8.34 (s, 1H), 7.40 (d, 1H), 4.24 (t, 2H), 3.57 (broad m, 4H), 2.45 (t, 2H), 2.37 (broad m, 4H), 1.92 (m, 2H). MS m/z 432 (M+1).

The procedure described in Example 20a was further applied, by using appropriate amines to prepare the following compound as either TFA salt, free base or HCl salt:

20b: 6-[4-(3-Ethylamino-propoxy)-3-(trifluoromethyl)-phenyl]-1H-imidazo[4,5-c]pyridine-4-carbonitrile TFA salt $^1$H NMR (CD3OD) δ: 8.53 (s, 1H), 8.36 (m, 2H), 8.30 (s, 1H), 7.35 (d, 1H), 4.33 (t, 2H), 3.26 (t, 2H), 3.12 (q, 2H), 2.28 (m, 2H), 1.34 (t, 3H). MS ml 390 (M+1).

20c: 6-{4-[3-((R)-2-Hydroxymethyl-pyrrolidin-1-yl)-propoxy]-3-(trifluoromethyl)-phenyl}-1H-imidazo[4,5-c]pyridine-4-carbonitrile $^1$H NMR (DMSO) δ: 8.66 (s, 1H), 8.47 (s, 1H), 8.38 (d, 1H), 8.34 (s, 1H), 7.41 (d, 1H) 4.25 (m, 2H), 3.40 (m, 1H), 3.25 (m, 1H), 3.15 (m, 1H), 3.05 (m, 1H), 2.60 (m, 1H), 2.49 (m, 1H), 2.31 (m, 1H), 1.95 (m, 2H), 1.85 (m, 1H), 1.70 (m, 1H), 1.60 (m, 2H). MS m/z 446 (M+1).

20d: 6-[4-(3-Perhydro-1,4-oxazepin-4-yl-propoxy)-3-trifluoromethyl)-phenyl]-1H-imidazo[4,5-c]pyridine-4-carbonitrile TFA salt $^1$H NMR (CD3OD) δ: 8.53 (s, 1H), 8.36 (s, 1H), 8.33 (d, 1H), 8.31 (s, 1H), 7.35 (d, 1H), 4.33 (t, 2H), 3.94 (broad m, 4H), 3.63 (broad m, 2H), 3.48 (t, 2H), 3.36 (broad m, 2H), 2.35 (broad m, 2H), 2.19 (broad m, 2H). MS m/z 446 (M+1).

20e: 6-{4-[3-(3,3-Difluoro-pyrrolidin-1-yl)-propoxy]-3-(trifluoromethyl)-phenyl}-1H-imidazo[4,5-c]pyridine-4-carbonitrile TFA salt $^1$H NMR (CD3OD) δ: 8.53 (s, 1H), 8.36 (s, 1H), 8.34 (d, 1H), 8.31 (s, 1H), 7.35 (d, 1H), 4.33 (t, 2H), 3.95 (broad m, 2H), 3.75 (broad m, 2H), 3.49 (t, 2H), 2.69 (m, 2H), 2.32 (m, 2H) MS m/z 452.5 (M+1).

20f: 6-{4-[3-Ethyl-piperazin-1-yl)-propoxy]-3-(trifluoromethyl)-phenyl}-1H-imidazo[4,5-c]pyridine-4-carbonitrile $^1$H NMR (DMSO) δ: 8.64 (s, 1H), 8.45 (s, 1H), 8.38 (d, 1H), 8.34 (s, 1H), 7.39 (d, 1H), 4.22 (t, 2H), 2.45 (t, 2H), 2.39 (broad m, 8H), 2.31 (m, 2H), 1.91 (m, 2H), 0.98 (t, 3H). MS m/z 459 (M+1).

20g: 6-(4-{3-[4-(2-Methoxy-ethyl)-piperazin-1-yl]-propoxy}-3-(trifluoromethyl)-phenyl)-1H-imidazo[4,5-c]pyridine-4-carbonitrile $^1$H NMR (DMSO) δ: 8.66 (s, 1H), 8.46 (s, 1H), 8.35 (d, 1H), 8.33 (s, 1H), 7.39 (d, 1H), 4.22 (t, 2H), 3.41 (t, 2H), 3.22 (s, 3H), 2.46 (broad m, 12H), 1.91 (m, 2H). MS m/z 489 (M+1).

20h: 6-(4-{3-[4-(2-Oxo-2-pyrrolidin-1-yl-ethyl)-piperazin-1-yl]-propoxy}-3-(trifluoromethyl)-phenyl)-1H-imidazo[4,5-c]pyridine-4-carbonitrile $^1$H NMR (DMSO) δ: 8.66 (s, 1H), 8.46 (s, 1H), 8.35 (d, 1H), 8.33 (s, 1H), 7.40 (d, 1H), 4.23 (t, 2H), 3.46 (t, 2H), 3.25 (m, 2H), 3.06 (s, 2H), 2.47 (m, 2H), 2.40 (broad m, 8H), 1.91 (m, 2H), 1.84 (m, 2H), 1.74 (m, 2H). MS m/z 542 (M+1).

20i: 6-{4-[3-(4-Hydroxy-piperidin-1-yl)-propoxy]-3-(trifluoromethyl)-phenyl}-1H-imidazo[4,5-c]pyridine-4-carbonitrile TFA salt $^1$H NMR (CD3OD) δ: 8.52 (s, 1H), 8.31 (s, 1H), 8.28 (d, 1H), 8.26 (s, 1H), 7.30 (d, 1H), 4.31 (t, 2H), 4.12 (broad s, 0.5H), 3.88 (broad m, 0.5H), 3.62 (broad d, 1H), 3.45 (broad d, 1H), 3.35 (broad m, 3H), 3.11 (broad t, 1H), 2.32 (broad m, 2H), 2.18 (broad d, 1H), 1.98 (broad m, 2H), 1.71 (broad m, 1H). MS m/z 446 (M+1).

20j: 6-{4-[3-((S)-3-Dimethylamino-pyrrolidin-1-yl)-propoxy]-3-(trifluoromethyl)-phenyl}-H-imidazo[4,5-c]pyridine-4-carbonitrile $^1$H NMR (DMSO) δ: 8.65 (s, 1H), 8.46 (s, 1H), 8.38 (d, 1H), 8.34 (s, 1H), 7.39 (d, 1H), 4.23 (t, 2H), 2.80 (m, 1H), 2.70 (t, 1H), 2.61 (m, 3H), 2.47 (m, 1H), 2.38 (m, 1H), 2.16 (s, 6H), 1.92 (m, 3H), 1.60 (m, 1H). MS m/z 459 (M+1).

EXAMPLE 21

6-{3-Chloro-4-[3-(piperazin-1-yl)-propoxy]-5-(trifluoromethyl)-phenyl}-1-methyl-1H-imidazo[4,5-c]pyridine-4-carbonitrile

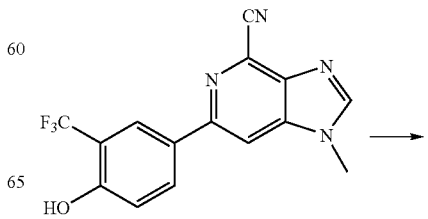

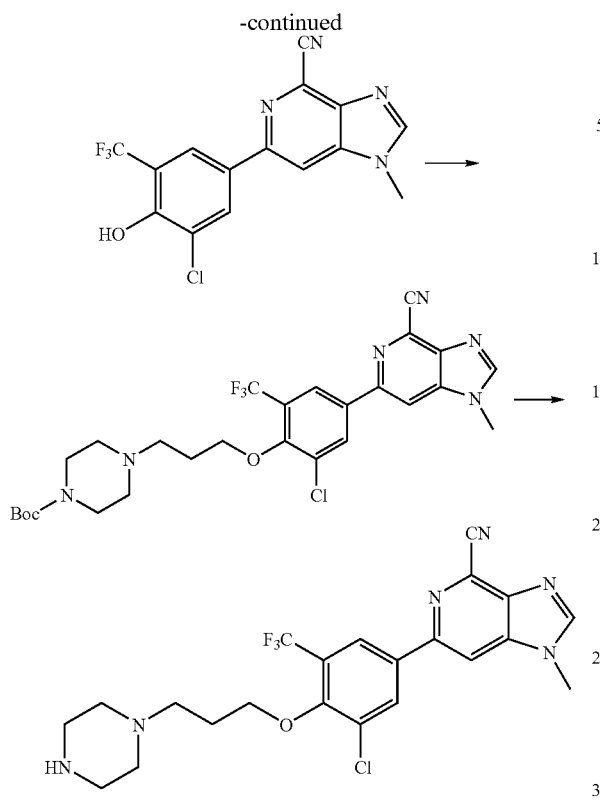

A: 6-(3-Chloro-4-hydroxy-5-trifluoromethyl-phenyl)-1-methyl-1H-imidazo[4,5-c]pyridine-4-carbonitrile N-Chlorosuccinimide (84 mg) was added to a solution of 6-(4-hydroxy-3-trifluoromethyl-phenyl)-1-methyl-1H-imidazo[4,5-c]pyridine-4-carbonitrile (200 mg) in DMF (4 ml). The mixture was stirred at room temperature for 24 hours, then ethyl acetate (50 ml) and water (20 ml) were added and the organic layer was washed twice with water (2×20 ml) and brine (20 ml), then dried over sodium sulfate, filtered and concentrated under reduced pressure to afford a crude (165 mg) with 6-(3-chloro-4-hydroxy-5-trifluoromethyl-phenyl)-1-methyl-1H-imidazo[4,5-c]pyridine-4-carbonitrile which is contaminated starting material. This material was used for next step without further purification.

MS m/z 353 (M+1).

B: 4-(3-Hydroxy-propyl)-piperazine-1-carboxylic acid tert-butyl Ester

Di-tert-butyldicarbonate (1.50 g) was added to a solution of 3-(1-piperazine)-propanol (1.00 g) in THF (50 ml) at 0° C. The mixture was stirred overnight at room temperature, then the solvent was removed under reduced pressure to afford 4-(3-hydroxy-propyl)-piperazine-1-carboxylic acid ter-butyl ester (1.66 g).

$^1$H NMR (CD3CN) δ: 3.81 (m, 2H); 3.43 (m, 4H); 2.62 (m, 2H); 2.47 (m, 4H); 1.73 (m, 2H); 1.45 (s, 9H).

C: 4-(3-Bromo-propyl)-piperazine-1-carboxylic acid tert-butyl Ester

Under nitrogen atmosphere, a solution of triphenylphosphine (0.94 g) in THF (4 ml) was added slowly to a mixture of 4-(3-hydroxy-propyl)-piperazine-1-carboxylic acid tert-butyl ester (0.80 g) and tetrabromomethane (1.19 g) in THF (15 ml). The mixture was stirred at room temperature for 16 hours, then ethyl acetate (100 ml) and a saturated solution of sodium carbonate (30 ml) were added and the organic layer was washed with brine, then dried over sodium sulfate, filtered and concentrated under reduced pressure. The residue was chromatographed over silica gel (eluent: Cyclohexane/Ethyl acetate 8/2) to afford 4-(3-bromo-propyl)-piperazine-1-carboxylic acid tert-butyl ester (0.66 g).

$^1$H NMR (CD$_3$CN) δ: 3.47 (m, 2H); 3.42 (m, 4H); 2.48 (m, 2H); 2.38 (m, 4H); 2.02 (m, 2H); 1.46 (s, 9H).

D: 4-{3-[2-Chloro-4-(4-cyano-1-methyl-1H-imidazo[4,5-c]pyridin-6-yl)-6-trifluoromethyl-phenoxy]-propyl}-piperazine-1-carboxylic acid tert-butyl Ester 4-(3-Bromo-propyl)-piperazine-1-carboxylic acid tert-butyl ester (172 mg) was added to a mixture of 6-(3-chloro-4-hydroxy-5-trifluoromethyl-phenyl)-1-methyl-1H-imidazo[4,5-c]pyridine-4-carbonitrile (165 mg) and potassium carbonate (130 mg) in acetonitrile (15 ml). The mixture was refluxed for 4 hours, then ethyl acetate (50 ml) and water (30 ml) were added and the organic layer was washed with brine, then dried over sodium sulfate, filtered and concentrated under reduced pressure to afford a crude product, 4-{3-[2-chloro-4-(4-cyano-1-methyl-1H-imidazo[4,5-c]pyridin-6-yl)-6-trifluoromethyl-phenoxy]-propyl}-piperazine-1-carboxylic acid tert-butyl ester.

MS m/z 579 (M+1).

E: 6-{3-Chloro-4-[3-(piperazin-1-yl)-propoxy]-5-trifluoromethyl)-phenyl}-1-methyl-1H-imidazo[4,5-c]pyridine-4-carbonitrile The crude product of 4-{3-[2-chloro-4-(4-cyano-1-methyl-1H-imidazo[4,5-c]pyridin-6-yl)-6-trifluoromethyl-phenoxy]-propyl}-piperazine-1-carboxylic acid tert-butyl from was dissolved in MeOH (7 ml) and a 5N solution of HCl in iPrOH (7.6 ml) was added. The mixture was stirred 3 hours at room temperature, then the solvent was evaporated under reduced pressure. The crude product was directly purified by preparative HPLC (HPLC:column XBridge MS C18 30×100 mm, 5 μm, Eluent:A:NH$_4$HCO$_3$, 10 mmol, pH=9.5/B:Acetonitrile, Focused gradient/8 minutes/50 mL/min) to afford 6-{3-chloro-4-[3-(piperazin-1-yl)-propoxy]-5-(trifluoromethyl)-phenyl}-1-methyl-1H-imidazo[4,5-c]pyridine-4-carbonitrile.

$^1$H NMR (CDCl3) δ: 8.34 (s, 1H), 8.16 (s, 1H), 8.13 (s, 1H), 7.91 (s, 1H), 4.20 (t, 2H), 4.01 (s, 3H), 2.93 (t, 4H), 2.60 (t, 2H), 2.49 (br, 4H), 2.09 (t, 2H). MS m/z 479 (M+H). MS m/z 479 (M+1).

The procedure described in Example 7a was further applied, using the appropriate starting materials, to prepare the following compound:

EXAMPLE 22

6-(4-(3-(3,5-Dimethyl-1H-pyrazol-1-yl)propoxy)-3-trifluoromethyl)phenyl)-1-methyl-1H-imidazo[4,5-c]pyridine-4-carbonitrile

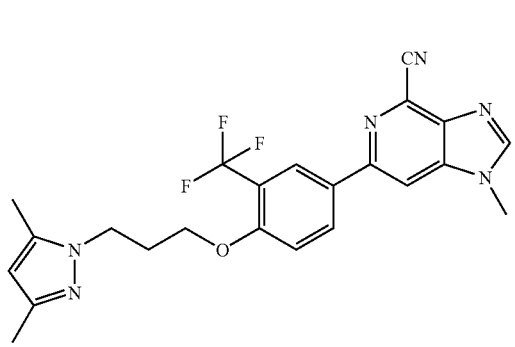

$^1$H NMR (DMSO$_{d6}$) δ: 8.72 (s, 1H), 8.64 (s, 1H) 8.44 (d, 1H), 8.43 (s, 1H), 7.41 (d, 1H), 5.79 (s, 1H), 4.17 (t, 2H), 4.10 (t, 2H), 3.99 (s, 3H) 2.19 (m, 2H), 2.15 (s, 3H), 2.09 (s, 3H). MS m/z 455.2 (M+1).

The procedure described in Example 4a was further applied, using the appropriate piperazine derivatives, to prepare the following compounds as either TFA salt, free base or HCl salt:

EXAMPLE 23

1-Methyl-6-{3-(trifluoromethyl)-4-[(3-(S)-isopropylpiperazin-1-yl)-propoxy]-phenyl}-1H-imidazo[4,5-c]pyridine-4-carbonitrile Hydrochloride

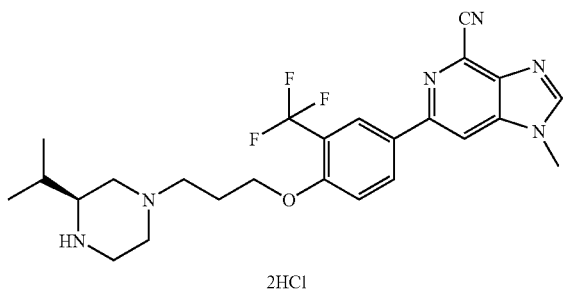

$^1$H NMR (MeOD) δ: 8.83 (s, 1H), 8.52 (s, 1H), 8.41 (s, 1H), 8.40 (d, 1H), 7.40 (d, 1H), 4.37 (m, 2H), 4.09 (s, 3H), 3.93 (m, 2H), 3.76 (m, 1H), 3.67 (m, 2H), 3.45-3.6 (m, 3H), 3.37 (t, 1H), 2.45 (m, 2H), 2.10 (m, 1H), 1.16 (d, 3H), 1.14 (d, 3H) MS m/z 487 (M+1).

EXAMPLE 24

6-(4-(2-(1-ethylpiperidin-4-yl)ethoxy)-3-(trifluoromethyl)phenyl)-1-methyl-1H-imidazo[4,5-c]pyridine-4-carbonitrile 2,2,2-trifluoroacetate

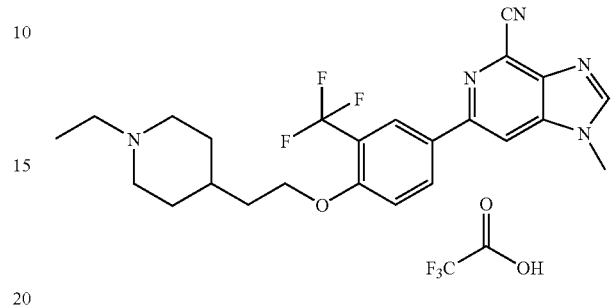

1-Methyl-6-{4-[2-(piperidin-4-yl)-ethoxy]-3-(trifluoromethyl)-phenyl}-1H-imidazo[4,5-c]pyridine-4-carbonitrile hydrochloride (20 mg), ethyl iodide (10 mg) and potassium carbonate (20 mg) in acetonitrile (1 ml) was stirred at room temperature for 20 hours. After removal of solid by filtration, filtrate was purified by HPLC to give 6-{4-[2-(1-ethylpiperidin-4-yl)ethoxy]-3-(trifluoromethyl)phenyl}-1-methyl-1H-imidazo[4,5-c]pyridine-4-carbonitrile as TFA salt.

$^1$H NMR (CD3OD) δ: 8.45 (s, 1H), 8.38 (s, 2H), 8.37 (d, 1H), 7.33 (d, 1H), 4.28 (t, 2H), 4.02 (s, 3H), 3.62 (m, 2H), 3.18 (q, 2H), 2.95 (m, 2H), 2.14 (m, 2H), 2.0 (m, 1H), 1.9 (m, 2H), 1.55 (m, 2H), 1.35 (t, 3H) MS m/z 458 (M+1).

The procedure described in Example 13a was further applied, using the appropriate alcohol derivatives, to prepare the following compounds as either TFA salt, neutral compound or HCl salt:

EXAMPLE 25a

1-Methyl-6-[4-(6-methyl-pyridin-2-ylmethoxy)-3-trifluoromethyl-phenyl]-1H-imidazo[4,5-c]pyridine-4-carbonitrile

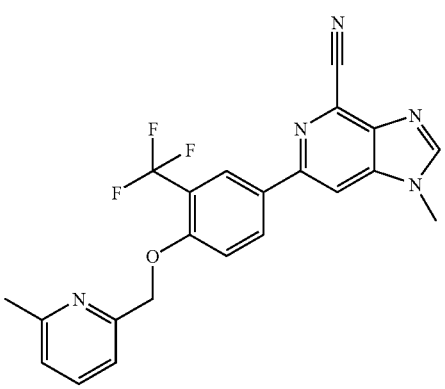

$^1$H NMR (DMSO) δ: 8.74 (s, 1H), 8.65 (s, 1H), 8.44 (d, 2H), 7.78 (t, 1H), 7.52 (d, 1H), 7.31 (d, 1H), 7.23 (d, 1H), 5.40 (s, 2H), 3.99 (s, 3H), 2.50 (s, 3H). MS m/z 424.0 (M+1).

EXAMPLE 25b

1-Methyl-6-[4-(pyrimidin-2-ylmethoxy)-3-trifluoromethyl-phenyl]-1H-imidazo[4,5-c]pyridine-4-carbonitrile

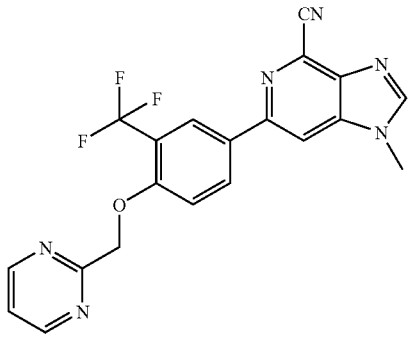

$^1$H NMR (DMSO) δ: 8.86 (d, 2H), 8.70 (s, 1H), 8.64 (s, 1H), 8.42 (s, 1H), 8.35 (d, 1H), 7.49 (t, 1H), 7.38 (d, 1H), 5.56 (s, 2H), 3.98 (s, 3H). MS m/z 411.0 (M+1).

EXAMPLE 25c 6-(4-((5-isopropylisoxazol-3-yl)methoxy)-3-(trifluoromethyl)phenyl)-1-methyl-1H-imidazo[4,5-c]pyridine-4-carbonitrile

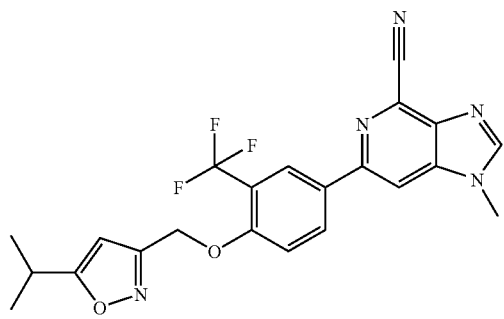

$^1$H NMR (CDCl3) δ: 8.28 (1H, s); 8.23 (1H, d); 8.10 (1H, s); 7.88 (1H, s); 7.24 (1H, d); 6.12 (1H, s); 5.31 (2H, s); 3.99 (3H, s); 3.08 (1H, m); 1.32 (6H, d). MS ml 442 (M+1).

EXAMPLE 25d 6-(4-((3-isopropylisoxazol-5-yl)methoxy)-3-(trifluoromethyl)phenyl-1-methyl-1H-imidazo[4,5-c]pyridine-4-carbonitrile

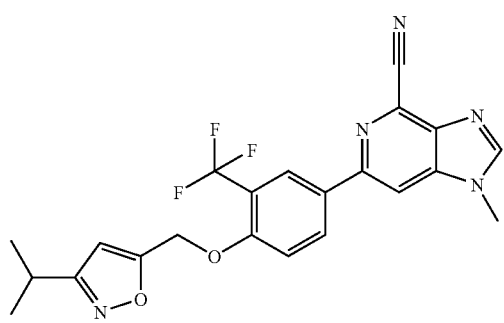

$^1$H NMR (CDCl3) δ: 8.27 (1H, s); 8.26 (1H, d); 8.09 (1H, s); 7.89 (1H, s); 7.18 (1H, d); 6.27 (1H, s); 5.30 (2H, s); 4.00 (3H, s); 3.08 (1H, m); 1.30 (6H, d). MS m/z 442 (M+1).

EXAMPLE 25e 6-(4-((3-isopropyl-1,2,4-oxadiazol-5-yl)methoxy)-3-(trifluoromethyl)phenyl)-1-methyl-1H-imidazo[4,5-c]pyridine-4-carbonitrile

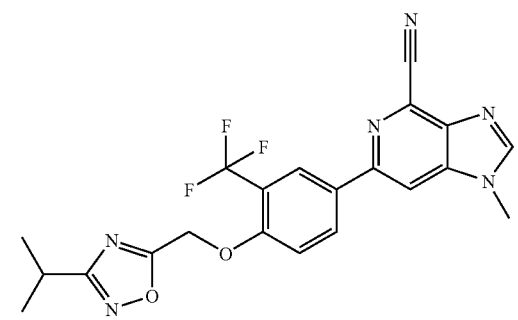

$^1$H NMR (CDCl3) δ: 8.29 (1H, d); 8.26 (1H, s); 8.10 (1H, d); 7.89 (1H, s); 7.23 (1H, d); 5.44 (2H, s); 4.00 (3H, s); 3.15 (1H, m); 1.35 (6H, d). MS m/z 443 (M+1).

EXAMPLE 26

Cathepsin S Assay Procedure

The inhibitory activity of the compounds of the invention was demonstrated in vitro by measuring the inhibition of recombinant human Cathepsin S as follows:

To a 384 well microtitre plate is added 10 µl of a 100 µM solution of test compound in assay buffer (110 mM sodium acetate pH5.5, 5 mM EDTA, 5 mM dithiothreitol) with 10% dimethylsulfoxide (DMSO), plus 20 µl of 250 µM solution of the substrate Z-Val-Val-Arg-AMC (7-amido-coumarine derivative of the tripeptide N-benzyloxycarbonyl-Val-Val-Arg-OH) in assay buffer and 45 µl of assay buffer. 25 µl of a 2 mg/l solution of activated recombinant human cathepsin S, in assay buffer, is then added to the well, yielding a final inhibitor concentration of 10 µM. Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity).

Compounds of the invention typically have a $pIC_{50}$ (negative logarithm of the $IC_{50}$ concentration) for inhibition of human cathepsin S of more than 6. Most compounds of the invention have a $pIC_{50}$ of more than 7, such as exemplified by the compounds of examples 1, 2a, 2c, 2u, 4a, 4b, 4c, 4e, 4f, 5a, 7b, 9d, 11, 12, 13c, 20f.

EXAMPLE 27

Cathepsin K Assay Procedure

The inhibitory activity of the compounds of the invention was demonstrated in vitro by measuring the inhibition of recombinant human Cathepsin K as follows:

To a 384 well microtitre plate is added 5 µl of a 100 µM solution of test compound in assay buffer (100 mM sodium acetate pH5.5, 5 mM EDTA, 5 mM dithiothreitol) with 10% dimethylsulfoxide (DMSO), plus 10 µl of 100 µM solution of the substrate Z-Phe-Arg-AMC (7-amido-coumarine derivative of the dipeptide N-benzyloxycarbonyl-Phe-Arg-OH) in assay buffer and 25 µl of assay buffer. 10 µl of a 1 mg/l solution of activated recombinant human cathepsin K, in assay buffer, is then added to the well, yielding a final inhibitor concentration of 10 µM.

Enzyme activity is determined by measuring the fluorescence of the liberated aminomethylcoumarin at 440 nM using 390 nM excitation, at 10 minutes Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity).

Compounds of the invention have a $pIC_{50}$ (negative logarithm of the $IC_{50}$ concentration) for inhibition of human cathepsin K of less than 7.

The invention claimed is:
1. A 6-phenyl-1H-imidazo[4,5-c]pyridine-4-carbonitrile derivative having the general Formula I

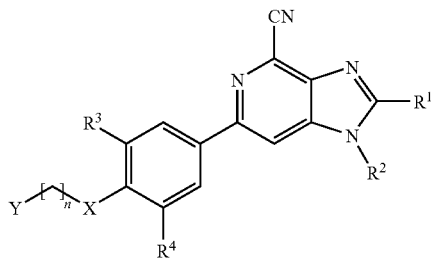

Formula I wherein
R1 is H or (C1-3)alkyl;
R2 is H or (C1-3)alkyl;
R3 is halogen or (C1-4)alkyl, optionally substituted with one or more halogens;
R4 is H, halogen or CN;
X is CH2, O or S;
n is 1-5;
Y is selected from OH, CN, (C1-3)alkylcarbonyl, NR5R6 and Z, wherein
Z is a saturated 5-or-6-membered heterocyclic ring containing 1-3 heteroatoms selected from O, S and NR7, which ring may be substituted by OH, oxo, (C1-3)alkyl, hydroxy(C1-3)alkyl or (C1-3)alkoxy(C1-3)alkyl; or wherein
Z is an aromatic 5- or 6-membered heterocyclic ring containing 1-3 heteroatoms selected from O, S and N, which ring may be substituted by OH, (C1-3)alkyl or hydroxy (C1-3)alkyl;
R5 and R6 are independently H, (C3-8)cycloalkyl or (C1-6)alkyl, optionally substituted with halogen, OH, CF3, (C3-8)cycloalkyl, (C1-6)alkyloxy, CONR14R15, NR14R15, SO2R16, a 5- or 6-membered heteroaryl group containing 1-3 heteroatoms selected from O, S and N, or a 5-or-6-membered saturated heterocyclic group containing a heteroatom selected from O, S or NR8; or
R5 and R6 together with the nitrogen to which they are bound form a 4-10 membered saturated heterocyclic ring, optionally further comprising 1-3 heteroatoms selected from O, S and NR9, the ring being optionally substituted with OH, oxo, (C1-4)alkyl, hydroxy(C1-3) alkyl, (C3-8) cycloalkyl, CONR10R11 or NR10R11;
R7 is H, (C1-3)alkyl or hydroxy(C1-3)alkyl;
R8 is H, (C1-3)alkyl or hydroxy(C1-3)alkyl;
R9 is H, (C1-3)alkyl, (C3-7)cycloalkyl, hydroxy(C1-3) alkyl, (C1-3)alkoxy(C1-3)alkyl, (C1-6)alkylcarbonyl, (C1-6)alkyloxycarbonyl, CONR12R13, CH2CONR12R13 or a 5-or 6-membered heteroaryl group containing 1-3 heteroatoms selected from O, S and N;
R10 and R11, are independently H or (C1-3)alkyl;
R12 and R13 are independently H or (C1-3)alkyl; or
R12 and R13 together with the nitrogen to which they are bound form a 4-8 membered saturated heterocyclic ring, optionally further comprising a heteroatom selected from O and S;
R14 and R15 are independently H or (C1-3)alkyl; or
R14 and R15 together with the nitrogen to which they are bound form a 4-8 membered saturated heterocyclic ring, optionally further comprising a heteroatom selected from O and S;
R16 is (C1-3)alkyl; or a pharmaceutically acceptable salt thereof.

2. The 6-phenyl-1H-imidazo[4,5-c]pyridine-4-carbonitrile derivative of claim 1 wherein R1 is H.

3. The 6-phenyl-1H-imidazo[4,5-c]pyridine-4carbonitrile derivative of claim 2, wherein R3 is CF3 and R4 is H.

4. The 6-phenyl-1H-imidazo[4,5-c]pyridine-4-carbonitrile derivative of claim 3, wherein X is O and n is 1 or 2 or 3.

5. The 6-phenyl-1H-imidazo[4,5-c]pyridine-4-carbonitrile derivative of claim 4, wherein Y is NR5R6.

6. The 6-phenyl-1H-imidazo[4,5-c]pyridine-4-carbonitrile derivative of claim 4, wherein Y is Z and wherein Z is pyridyl.

7. The 6-phenyl-1H-imidazo[4,5-c]pyridine-4-carbonitrile derivative of claim 1 which is selected from
6-[4-(3-dimethylaminopropoxy)-3-(trifluoromethyl)-phenyl]-1-methyl-1H-imidazo[4,5-c]pyridine-4-carbonitrile;
1-methyl-6-[4-(3-pyrrolidin-1-ylpropoxy)-3-(trifluoromethyl)-phenyl]-1H-imidazo[4,5-c]pyridine-4-carbonitrile;
6-[4-(3-N,N-diethylamino-propoxy)-3-(trifluoromethyl)-phenyl]-1-methyl-1H-imidazo[4,5-c]pyridine-4-carbonitrile;
1-methyl-6-[3-(trifluoromethyl)-4-(3-(3,3,4-trimethylpiperazin-1-yl)-propoxy)-phenyl]-1H-imidazo[4,5-c]pyridine-4-carbonitrile;
6-{4-[3-(3,3-dimethylpiperazin-1-yl)-propoxy]-3-(trifluoromethyl)-phenyl}-1-methyl-1H-imidazo[4,5-c]pyridine-4-carbonitrile;
6-{4-[3-(cis-3,5-dimethylpiperazin-1-yl)-propoxy]-3-(trifluoromethyl)-phenyl}-1-methyl-1H-imidazo[4,5-c] pyridine-4-carbonitrile;
1-methyl-6-{4-[3-(4-methylpiperazin-1-yl)-propoxy]-3-(trifluoromethyl)-phenyl}-1H-imidazo[4,5-c]pyridine-4-carbonitrile;

6-{4-[3-(4-ethylpiperazin-1-yl)-propoxy]-3-(trifluoromethyl)-phenyl}-1-methyl-1H-imidazo[4,5-c]pyridine-4-carbonitrile;

1-methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile;

6-{4-[3-(2-ethyl-imidazol-1-yl)-propoxy]-3-(trifluoromethyl)-phenyl}-[1-methyl-1H-imidazo[4,5-c]pyridine-4-carbonitrile;

6-{4-[2-(cis-3,5-dimethyl-piperazin-1-yl)-ethoxy]-3-(trifluoromethyl)-phenyl}-1-methyl-1H-imidazo[4,5-c]pyridine-4-carbonitrile;

1-methyl-6-{4-[2-(8-methyl-2,4-dioxo-1,3,8-triaza-spiro[4.5]dec-3-yl)-ethoxy]-3-(trifluoromethyl)-phenyl}-1H-imidazo[4,5-c]pyridine-4-carbonitrile;

1-methyl-6-[4-(pyridin-2-yl-methoxy)-3-(trifluoromethyl)-phenyl]-1H-imidazo[4,5-c]pyridine-4-carbonitrile;

6-{4-[3-(4-ethyl-piperazin-1-yl)-propoxy]-3-(trifluoromethyl)-phenyl}-1H-imidazo[4,5-c]pyridine-4-carbonitrile;

1-methyl-6-{3-(trifluoromethyl)-4-[(3-(S)-isopropylpiperazin-1-yl)-propoxy]-phenyl}-1H-imidazo[4,5-c]pyridine-4-carbonitrile hydrochloride;

6-(4-(2-(1-ethylpiperidin-4-yl)ethoxy)-3-(trifluoromethyl)phenyl)-1-methyl-1H-imidazo[4,5-c]pyridine-4-carbonitrile 2,2,2-trifluoroacetate; and 1-methyl-6-[4-(6-methyl-pyridin-2-ylmethoxy)-3-trifluoromethyl-phenyl]-1H-imidazo[4,5-c]pyridine-4-carbonitrile; or a pharmaceutically acceptable salt thereof.

8. A pharmaceutical composition comprising a 6-phenyl-1H-imidazo[4,5-c]-pyridine-4-carbonitrile derivative of claim 1, or a pharmaceutically acceptable salt thereof in admixture with pharmaceutically acceptable auxilliaries.

9. The pharmaceutical composition of claim 8, wherein the 6phenyl-1H-imidazo[4,5-c]pyridine-4-carbonitrile derivative is selected from the group consisting of 6-[4-(3-dimethylaminopropoxy)-3-(trifluoromethyl)-phenyl]-1-methyl-1H-imidazo[4,5-c]pyridine-4-carbonitrile;

1-methyl-6-[4-(3-pyrrolidin-1-ylpropoxy)-3-(trifluoromethyl)-phenyl]-1H-imidazo[4,5-c]pyridine-4-carbonitrile;

6-[4-(3-N,N-diethylamino-propoxy)-3-(trifluoromethyl)-phenyl]-1-methyl-1H-imidazo[4,5-c]pyridine-4-carbonitrile;

1-methyl-6-[3-(trifluoromethyl)-4-(3-(3,3,4-trimethylpiperazin-1-yl)-propoxy)-phenyl]-1H-imidazo[4,5-c]pyridine-4-carbonitrile;

6-{4-[3-(3,3-dimethylpiperazin-1-yl)-propoxy]-3-(trifluoromethyl)-phenyl}-1-methyl-1H-imidazo[4,5-c]pyridine-4-carbonitrile;

6-{4-[3-(cis-3,5-dimethylpiperazin-1-yl)-propoxy]-3-(trifluoromethyl)-phenyl}-1-methyl-1H-imidazo[4,5-c]pyridine-4-carbonitrile;

1-methyl-6-{4-[3-(4-methylpiperazin-1-yl)-propoxy]-3-(trifluoromethyl)-phenyl}-1H-imidazo[4,5-c]pyridine-4-carbonitrile;

6-{4-[3-(4-ethylpiperazin-1-yl)-propoxy]-3-(trifluoromethyl)-phenyl}-1-methyl-1H-imidazo[4,5-c]pyridine-4-carbonitrile;

1-methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile;

6-{4-[3-(2-ethyl-imidazol-1-yl)-propoxy]-3-(trifluoromethyl)-phenyl}-1-methyl-1H-imidazo[4,5-c]pyridine-4-carbonitrile;

6-{4-[2-(cis-3,5-dimethyl-piperazin-1-yl)-ethoxy]-3-(trifluoromethyl)-phenyl}-1-methyl-1H-imidazo[4,5-c]pyridine-4-carbonitrile;

1-methyl-6-{4-[2-(8-methyl-2,4-dioxo-1,3,8-triaza-spiro[4.5]dec-3-yl)-ethoxy]-3-(trifluoromethyl)-phenyl}-1H-imidazo[4,5-c]pyridine-4-carbonitrile;

1-methyl-6-[4-(pyridin-2-yl-methoxy)-3-(trifluoromethyl)-phenyl]-1H-imidazo[4,5-c]pyridine-4-carbonitrile;

6-{4-[3-(4-ethyl-piperazin-1-yl)-propoxy]-3-(trifluoromethyl)-phenyl}-1H-imidazo[4,5-c]pyridine-4-carbonitrile;

1-methyl-6-{3-(trifluoromethyl)-4-[(3-(S)-isopropylpiperazin-1-yl)-propoxy]-phenyl}-1H-imidazo[4,5-c]pyridine-4-carbonitrile hydrochloride;

6-(4-(2-(1-ethylpiperidin-4-yl)ethoxy)-3-(trifluoromethyl)phenyl)-1-methyl-1H-imidazo[4,5-c]pyridine-4-carbonitrile 2,2,2-trifluoroacetate; and 1-methyl-6-[4-(6-methyl-pyridin-2-ylmethoxy)-3-trifluoromethyl-phenyl]-1H-imidazo[4,5-c]pyridine-4-carbonitrile; or a pharmaceutically acceptable salt thereof.

10. A method for the treatment of a disorder selected from the group consisting of atherosclerosis, rheumatoid arthritis and chronic pain, the method comprising administering to a human in need thereof an effective amount of a 6-phenyl-1H-imidazo[4,5-c]pyridine-4-carbonitrile derivative of claim 1 or a pharmaceutically acceptable salt thereof.

11. The method of claim 10, wherein the disorder is rheumatoid arthritis.

12. The method of claim 10, wherein the chronic pain is neuropathic pain.

13. The method of claim 10, wherein the 6-phenyl-1H-imidazo[4,5-c]pyridine-4-carbonitrile derivative is selected from the group consisting of 6-[4-(3-dimethylaminopropoxy)-3-(trifluoromethyl)-phenyl]-1-methyl-1H-imidazo[4,5-c]pyridine-4-carbonitrile;

1-methyl-6-[4-(3-pyrrolidin-1-ylpropoxy)-3-(trifluoromethyl)-phenyl]-1H-imidazo[4,5-c]pyridine-4-carbonitrile;

6-[4-(3-N,N-diethylamino-propoxy)-3-(trifluoromethyl)-phenyl]-1-methyl-1H-imidazo[4,5-c]pyridine-4-carbonitrile;

1-methyl-6-[3-(trifluoromethyl)-4-(3-(3,3,4-trimethylpiperazin-1-yl)-propoxy)-phenyl]-1H-imidazo[4,5-c]pyridine-4-carbonitrile;

6-{4-[3-(3,3-dimethylpiperazin-1-yl)-propoxy]-3-(trifluoromethyl)-phenyl}-1-methyl-1H-imidazo[4,5-c]pyridine-4-carbonitrile;

6-{4-[3-(cis-3,5-dimethylpiperazin-1-yl)-propoxy]-3-(trifluoromethyl)-phenyl}-1-methyl-1H-imidazo[4,5-c]pyridine-4-carbonitrile;

1-methyl-6-{4-[3-(4-methylpiperazin-1-yl)-propoxy]-3-(trifluoromethyl)-phenyl}-1H-imidazo[4,5-c]pyridine-4-carbonitrile;

6-{4-[3-(4-ethylpiperazin-1-yl)-propoxy]-3-(trifluoromethyl)-phenyl}-1-methyl-1H-imidazo[4,5-c]pyridine-4-carbonitrile;

1-methyl-6-(4-{3-[4-(N-methylaminocarbonyl)-piperidin-1-yl]-propoxy}-3-(trifluoromethyl)-phenyl)-1H-imidazo[4,5-c]pyridine-4-carbonitrile;

6-{4-[3-(2-ethyl-imidazol-1-yl)-propoxy]-3-(trifluoromethyl)-phenyl}-1-methyl-1H-imidazo[4,5-c]pyridine-4-carbonitrile;

6-{4-[2-(cis-3,5-dimethyl-piperazin-1-yl)-ethoxy]-3-(trifluoromethyl)-phenyl}-1-methyl-1H-imidazo[4,5-c]pyridine-4-carbonitrile;

1-methyl-6-{4-[2-(8-methyl-2,4-dioxo-1,3,8-triaza-spiro[4.5]dec-3-yl)-ethoxy]-3-(trifluoromethyl)-phenyl}-1H-imidazo[4,5-c]pyridine-4-carbonitrile;

1-methyl-6-[4-pyridin-2-yl-methoxy)-3-(trifluoromethyl)-phenyl]-1H-imidazo[4,5-c]pyridine-4-carbonitrile;

6-{4-[3-(4-ethyl-piperazin-1-yl)-propoxy]-3-(trifluoromethyl)-phenyl}-1H-imidazo[4,5-c]pyridine-4-carbonitrile;

1-methyl-6-{3-(trifluoromethyl)-4-[(3-(S)-isopropylpiperazin-1-yl)-propoxy]-phenyl}-1H-imidazo[4,5-c]pyridine-4-carbonitrile hydrochloride;

6-(4-(2-(1-ethylpiperidin-4-yl)ethoxy)-3-(trifluoromethyl)phenyl)-1-methyl-1H-imidazo[4,5-c]pyridine-4-carbonitrile 2,2,2-trifluoroacetate; and 1-methyl-6-[4-(6-methyl-pyridin-2-ylmethoxy)-3-trifluoromethyl-phenyl]-1H-imidazo[4,5-c]pyridine-4-carbonitrile; or a pharmaceutically acceptable salt thereof.

14. The method of claim 10, wherein the disorder is atherosclerosis.

* * * * *

UNITED STATES PATENT AND TRADEMARK OFFICE
CERTIFICATE OF CORRECTION

| | | |
|---|---|---|
| PATENT NO. | : 7,932,251 B2 | Page 1 of 1 |
| APPLICATION NO. | : 12/173623 | |
| DATED | : April 26, 2011 | |
| INVENTOR(S) | : Cai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fourth Day of October, 2011

David J. Kappos
*Director of the United States Patent and Trademark Office*